(12) United States Patent
Kovacs et al.

(10) Patent No.: US 12,421,541 B2
(45) Date of Patent: Sep. 23, 2025

(54) MULTIOMIC ANALYSIS DEVICE AND METHODS OF USE THEREOF

(71) Applicant: Singular Genomics Systems, Inc., San Diego, CA (US)

(72) Inventors: Sandor Kovacs, Encinitas, CA (US); Eli N. Glezer, Del Mar, CA (US); Christopher Frye, San Diego, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 0 days.

(21) Appl. No.: 19/048,060

(22) Filed: Feb. 7, 2025

(65) Prior Publication Data

US 2025/0179566 A1    Jun. 5, 2025

Related U.S. Application Data

(63) Continuation of application No. 18/352,957, filed on Jul. 14, 2023, now Pat. No. 12,252,740, which is a continuation of application No. PCT/US2022/027630, filed on May 4, 2022.

(60) Provisional application No. 63/184,684, filed on May 5, 2021.

(51) Int. Cl.
    C12Q 1/6841    (2018.01)
    C12Q 1/6869    (2018.01)
    G01N 21/64     (2006.01)

(52) U.S. Cl.
    CPC ......... *C12Q 1/6841* (2013.01); *C12Q 1/6869* (2013.01); *G01N 21/6428* (2013.01); *G01N 21/6452* (2013.01); *G01N 21/6458* (2013.01); *G01N 2021/6439* (2013.01)

(58) Field of Classification Search
    CPC ............... C12Q 1/6841; C12Q 1/6869; G01N 21/6428; G01N 21/6452; G01N 21/6458; G01N 2021/6439
    See application file for complete search history.

(56) References Cited

U.S. PATENT DOCUMENTS

| | | |
|---|---|---|
| 4,318,846 A | 3/1982 | Khanna et al. |
| 4,792,520 A | 12/1988 | Stambrook et al. |
| 5,034,506 A | 7/1991 | Summerton et al. |
| 5,066,580 A | 11/1991 | Lee |
| 5,188,934 A | 2/1993 | Menchen et al. |
| 5,235,033 A | 8/1993 | Summerton et al. |
| 5,366,860 A | 11/1994 | Bergot et al. |
| 5,538,724 A | 7/1996 | Butcher et al. |
| 5,599,675 A | 2/1997 | Brenner et al. |
| 5,688,648 A | 11/1997 | Mathies et al. |
| 5,750,341 A | 5/1998 | Macevicz |
| 5,763,594 A | 6/1998 | Hiatt et al. |
| 5,800,996 A | 9/1998 | Lee et al. |
| 5,808,045 A | 9/1998 | Hiatt et al. |
| 5,847,162 A | 12/1998 | Lee et al. |
| 5,872,244 A | 2/1999 | Hiatt et al. |
| 6,210,891 B1 | 4/2001 | Nyren et al. |
| 6,218,122 B1 | 4/2001 | Friend et al. |
| 6,232,465 B1 | 5/2001 | Hiatt et al. |
| 6,258,568 B1 | 7/2001 | Nyren |
| 6,271,022 B1 | 8/2001 | Bochner |
| 6,274,320 B1 | 8/2001 | Rothberg et al. |
| 6,365,367 B1 | 4/2002 | Friedman et al. |
| 6,664,079 B2 | 12/2003 | Ju et al. |
| 7,057,026 B2 | 6/2006 | Barnes et al. |
| 7,264,929 B2 | 9/2007 | Rothberg et al. |
| 7,271,952 B2 | 9/2007 | Suzuki et al. |
| 7,390,463 B2 | 6/2008 | He et al. |
| 7,541,444 B2 | 6/2009 | Milton et al. |
| 8,003,354 B2 | 8/2011 | Shen et al. |
| 8,039,817 B2 | 10/2011 | Feng et al. |
| 8,178,360 B2 | 5/2012 | Barnes et al. |
| 8,241,573 B2 | 8/2012 | Banerjee et al. |
| 8,551,710 B2 | 10/2013 | Bernitz et al. |
| 9,371,598 B2 | 6/2016 | Chee |
| 9,556,473 B2 | 1/2017 | Bernitz et al. |
| 9,593,365 B2 | 3/2017 | Frisen et al. |
| 9,598,723 B2 | 3/2017 | Ammann et al. |
| 10,059,990 B2 | 8/2018 | Boyden et al. |
| 10,114,015 B2 | 10/2018 | Glezer et al. |
| 10,138,509 B2 | 11/2018 | Church et al. |
| 10,266,888 B2 | 4/2019 | Daugharthy et al. |
| 10,323,272 B1 | 6/2019 | Rabbani et al. |
| 10,495,554 B2 | 12/2019 | Deisseroth et al. |
| 10,738,072 B1 | 8/2020 | Graham et al. |
| 10,774,374 B2 | 9/2020 | Frisén et al. |
| 10,841,507 B2 | 11/2020 | Schürf et al. |
| 11,155,858 B2 | 10/2021 | Glezer et al. |
| 11,434,525 B2 | 9/2022 | Glezer |
| 11,486,004 B2 | 11/2022 | Witters et al. |
| 11,492,662 B2 | 11/2022 | Glezer et al. |
| 11,643,679 B2 | 5/2023 | Glezer et al. |
| 11,680,288 B2 | 6/2023 | Glezer |
| 11,714,271 B2 | 8/2023 | Cang et al. |
| 11,753,678 B2 | 9/2023 | Glezer |
| 11,891,656 B2 | 2/2024 | Glezer et al. |
| 12,252,740 B2 | 3/2025 | Kovacs et al. |
| 12,258,623 B2 | 3/2025 | Kovacs et al. |
| 2001/0054691 A1 | 12/2001 | Park et al. |
| 2002/0064779 A1 | 5/2002 | Landegren et al. |
| 2002/0159919 A1 | 10/2002 | Churchill et al. |

(Continued)

FOREIGN PATENT DOCUMENTS

| | | |
|---|---|---|
| JP | 2005265627 A | 9/2005 |
| JP | 5970959 B2 | 7/2016 |

(Continued)

OTHER PUBLICATIONS

International Search Report and Written Opinion issued in International Application No. PCT/US2021/045104, Nov. 23, 2021, 15 pages.

(Continued)

*Primary Examiner* — Narayan K Bhat
(74) *Attorney, Agent, or Firm* — Mintz, Levin, Cohn, Ferris, Glovsky and Popeo, P.C.; Zachary L. Terranova

(57) ABSTRACT

Disclosed herein, inter alia, are devices, compositions, kits, and methods for interrogating biological samples.

20 Claims, 14 Drawing Sheets

(56) References Cited

U.S. PATENT DOCUMENTS

| | | |
|---|---|---|
| 2003/0032024 A1 | 2/2003 | Lizardi |
| 2003/0049862 A1 | 3/2003 | He et al. |
| 2003/0082556 A1 | 5/2003 | Kaufman et al. |
| 2003/0143536 A1 | 7/2003 | Lizardi |
| 2004/0137484 A1 | 7/2004 | Zhang et al. |
| 2004/0248318 A1 | 12/2004 | Weinberger et al. |
| 2005/0089860 A1 | 4/2005 | Arita |
| 2005/0208644 A1 | 9/2005 | Takiguchi et al. |
| 2005/0287526 A1 | 12/2005 | Landegren et al. |
| 2006/0050376 A1 | 3/2006 | Houston et al. |
| 2006/0292559 A1 | 12/2006 | Reddy et al. |
| 2007/0020152 A1 | 1/2007 | Costello et al. |
| 2007/0077580 A1 | 4/2007 | Ikeda et al. |
| 2007/0077646 A1 | 4/2007 | Okamoto |
| 2009/0298718 A1 | 12/2009 | Denman et al. |
| 2010/0055733 A1 | 3/2010 | Lutolf et al. |
| 2011/0059865 A1 | 3/2011 | Smith et al. |
| 2011/0223585 A1 | 9/2011 | Gullberg et al. |
| 2011/0273706 A1 | 11/2011 | Noblett et al. |
| 2012/0270305 A1 | 10/2012 | Reed et al. |
| 2012/0301886 A1 | 11/2012 | Farrell et al. |
| 2013/0012399 A1 | 1/2013 | Myers et al. |
| 2013/0296535 A1 | 11/2013 | Church et al. |
| 2014/0056811 A1 | 2/2014 | Jacob et al. |
| 2014/0057799 A1 | 2/2014 | Johnson et al. |
| 2014/0120534 A1 | 5/2014 | Bernitz et al. |
| 2014/0170654 A1 | 6/2014 | Landegren et al. |
| 2014/0191109 A1 | 7/2014 | Chamberlin et al. |
| 2014/0256588 A1 | 9/2014 | Glezer et al. |
| 2015/0167092 A1 | 6/2015 | Kartalov et al. |
| 2015/0225778 A1 | 8/2015 | Hindson et al. |
| 2015/0238920 A1 | 8/2015 | Curran et al. |
| 2016/0017392 A1* | 1/2016 | Arnold .................. C12Q 1/6853 435/91.2 |
| 2016/0108392 A1 | 4/2016 | Stelling |
| 2016/0116384 A1 | 4/2016 | Chen et al. |
| 2016/0145677 A1 | 5/2016 | Chee et al. |
| 2016/0145696 A1 | 5/2016 | Brandon et al. |
| 2016/0257993 A1 | 9/2016 | Fu et al. |
| 2016/0304952 A1 | 10/2016 | Boyden et al. |
| 2016/0369329 A1 | 12/2016 | Cai et al. |
| 2017/0067096 A1 | 3/2017 | Wassie et al. |
| 2017/0067925 A1 | 3/2017 | Spence et al. |
| 2017/0107563 A1 | 4/2017 | Samusik et al. |
| 2017/0343539 A1 | 11/2017 | Epstein et al. |
| 2018/0246076 A1 | 8/2018 | Qian et al. |
| 2019/0017106 A1 | 1/2019 | Frisen et al. |
| 2019/0032121 A1 | 1/2019 | Daugharthy et al. |
| 2019/0055594 A1 | 2/2019 | Samusik et al. |
| 2019/0064109 A1 | 2/2019 | Brown et al. |
| 2019/0071668 A1 | 3/2019 | Schmidt et al. |
| 2019/0113423 A1 | 4/2019 | Goodman et al. |
| 2019/0119735 A1 | 4/2019 | Deisseroth et al. |
| 2019/0145982 A1 | 5/2019 | Chee et al. |
| 2019/0155835 A1 | 5/2019 | Daugharthy et al. |
| 2019/0161796 A1 | 5/2019 | Hauling et al. |
| 2019/0177718 A1 | 6/2019 | Church et al. |
| 2019/0194709 A1 | 6/2019 | Church et al. |
| 2019/0241950 A1 | 8/2019 | Daugharthy et al. |
| 2019/0258777 A1 | 8/2019 | Bo et al. |
| 2019/0264279 A1 | 8/2019 | Kain et al. |
| 2019/0376123 A1 | 12/2019 | Bobrow et al. |
| 2019/0391140 A1 | 12/2019 | Aghvanyan et al. |
| 2020/0071751 A1 | 3/2020 | Daugharthy et al. |
| 2020/0087707 A1 | 3/2020 | Engreitz |
| 2020/0103639 A1 | 4/2020 | Skinner et al. |
| 2020/0124601 A1 | 4/2020 | Fan et al. |
| 2020/0140944 A1 | 5/2020 | Belgrader et al. |
| 2020/0224244 A1 | 7/2020 | Nilsson et al. |
| 2020/0271556 A1 | 8/2020 | Sarkar et al. |
| 2020/0277663 A1 | 9/2020 | Iyer et al. |
| 2020/0277664 A1 | 9/2020 | Frenz |
| 2020/0290043 A1 | 9/2020 | Williamson et al. |
| 2020/0294439 A1 | 9/2020 | Mandle et al. |
| 2020/0362334 A1 | 11/2020 | Regev et al. |
| 2020/0393477 A1 | 12/2020 | Davey et al. |
| 2021/0017579 A1 | 1/2021 | Buse et al. |
| 2021/0018503 A1 | 1/2021 | Varadarajan et al. |
| 2021/0039062 A1 | 2/2021 | Mirkin et al. |
| 2021/0108195 A1 | 4/2021 | Bernate et al. |
| 2021/0164029 A1 | 6/2021 | Sekedat et al. |
| 2021/0164039 A1 | 6/2021 | Wang et al. |
| 2021/0189481 A1 | 6/2021 | Glezer et al. |
| 2021/0198727 A1 | 7/2021 | Kühnemund et al. |
| 2021/0222262 A1 | 7/2021 | Bakaher |
| 2021/0238662 A1 | 8/2021 | Bava et al. |
| 2021/0262018 A1 | 8/2021 | Bava et al. |
| 2021/0318530 A1 | 10/2021 | Deissler |
| 2021/0333211 A1 | 10/2021 | Chen et al. |
| 2021/0363579 A1 | 11/2021 | Daugharthy et al. |
| 2021/0382033 A1 | 12/2021 | Mir |
| 2021/0388424 A1 | 12/2021 | Bava |
| 2022/0112486 A1 | 4/2022 | Lyer et al. |
| 2022/0197002 A1 | 6/2022 | Cang et al. |
| 2022/0229044 A1 | 7/2022 | Feldman et al. |
| 2022/0333174 A1 | 10/2022 | Glezer et al. |
| 2022/0403457 A1 | 12/2022 | Glezer et al. |
| 2023/0088043 A1 | 3/2023 | Kovacs et al. |
| 2023/0100215 A1 | 3/2023 | Glezer et al. |
| 2023/0203570 A1 | 6/2023 | Kovacs et al. |
| 2023/0357828 A1 | 11/2023 | Glezer |
| 2023/0366013 A1 | 11/2023 | Glezer |
| 2023/0374572 A1 | 11/2023 | Kovacs et al. |

FOREIGN PATENT DOCUMENTS

| | | |
|---|---|---|
| WO | 8910977 A1 | 11/1989 |
| WO | 9607669 A1 | 3/1996 |
| WO | 2004018497 A2 | 3/2004 |
| WO | 2004018497 A3 | 6/2004 |
| WO | 2005039389 A2 | 5/2005 |
| WO | 2008042067 A2 | 4/2008 |
| WO | 2012106385 A2 | 8/2012 |
| WO | 2013090360 A2 | 6/2013 |
| WO | 2013090360 A3 | 8/2013 |
| WO | 2014030066 A2 | 2/2014 |
| WO | 2014030066 A3 | 5/2014 |
| WO | 2017079382 A1 | 5/2017 |
| WO | 2018091676 A1 | 5/2018 |
| WO | 2018148723 A1 | 8/2018 |
| WO | 2019068880 A1 | 4/2019 |
| WO | 2019084062 A1 | 5/2019 |
| WO | 2019199579 A1 | 10/2019 |
| WO | 2019222284 A1 | 11/2019 |
| WO | 2020028194 A1 | 2/2020 |
| WO | 2020056044 A1 | 3/2020 |
| WO | 2020076976 A1 | 4/2020 |
| WO | 2020076979 A1 | 4/2020 |
| WO | 2020096687 A1 | 5/2020 |
| WO | 2020099640 A1 | 5/2020 |
| WO | 2020123309 A1 | 6/2020 |
| WO | 2020160044 A1 | 8/2020 |
| WO | 2022056385 A1 | 3/2022 |
| WO | 2022235764 A1 | 11/2022 |

OTHER PUBLICATIONS

International Search Report and Written Opinion issued in International Application No. PCT/US2021/045105, Jan. 31, 2022, 18 pages.
International Search Report and Written Opinion issued in International Application No. PCT/US2022/027630, Sep. 19, 2022, 14 pages.
(2023) Researchers Fully Sequence the Y Chromosome for the First Time, National Institute of Standards and Technology, pp. 1-4.
(2006) The Cancer Genome Atlas Program (TCGA), National Cancer Institute Center for Cancer Genomics, www.cancer.gov/tcga, 2 pages.
(1988) The Stratagene Catalog, pp. 39.
Agrawal et al., (Nov. 15, 2016) "Nivolumab dose selection: challenges, opportunities, and lessons learned for cancer immunotherapy", Journal of Immunotherapy Cancer, 4:72 (11 pages).

(56) References Cited

OTHER PUBLICATIONS

Ahern H, (1995) "Biochemical, reagent kits offer scientists good return on investment", The Scientist, 9(15):20.
Alon et al., (2021) "Expansion Sequencing: Spatially Precise In Situ Transcriptomics in Intact Biological Systems", Science, 371(6528): eaax2656.
ANSI, (Jan. 9, 2004) "ANSI SLAS Jan. 2004 (R2012): for Microplates—Footprint Dimensions", Secretariat Society for Laboratory Automation and Screening, 8 pages.
ANSI, (Jan. 9, 2004) "ANSI SLAS Feb. 2004 (R2012): for Microplates—Height Dimensions", Secretariat Society for Laboratory Automation and Screening, 9 pages.
ANSI, (Jan. 9, 2004) "ANSI SLAS Mar. 2004 (R2012): for Microplates—Bottom Outside Flange Dimensions", Secretariat Society for Laboratory Automation and Screening, 10 pages.
ANSI, (Jan. 9, 2004) "ANSI SLAS Apr. 2004 (R2012): for Microplates—Well Positions", Secretariat Society for Laboratory Automation and Screening, 13 pages.
ANSI, (Apr. 9, 2009) "ANSI SLAS Jun. 2012: for Microplates—Well Bottom Elevation", Secretariat Society for Laboratory Automation and Screening, 9 pages.
Arce et al., (Jul. 24, 2013) "Fast and Accurate Automated Cell Boundary Determination for Fluorescence Microscopy", Scientific Reports, 3(1):2266 (1-6).
Auld et al., (Jun. 1, 2020) "Microplate Selection and Recommended Practices in High-throughput Screening and Quantitative Biology", Assay Guidance Manual [Internet], 50 pages.
Bains et al., (Dec. 7, 1988) "A Novel Method For Nucleic Acid Sequence Determination", Journal of Theoretical Biology, 135(3):303-307.
Bains et al., (May 28, 2009) "Quantifying The Development of the Peripheral Naive CD4+ T-cell Pool in Humans", Blood, 113(22):5480-5487.
Bullinger et al., (2004) "Use Of Gene-Expression Profiling To Identify Prognostic Subclasses In Adult Acute Myeloid Leukemia", New England Journal of Medicine, 350(16):1605-1616.
Cai Matthew, (2019) "Spatial Mapping of Single Cells in Human Cerebral Cortex Using Dartfish: a Highly Multiplexed Method for in Situ Quantification of Targeted RNA Transcripts", University of California, San Diego, 107 pages.
Carow et al., (2019) "Spatial And Temporal Localization Of Immune Transcripts Defines Hallmarks and Diversity in the Tuberculosis Granuloma", Nature Communications, 10(1):1823 (15 pages).
Carpenter et al., (Oct. 31, 2006) "Cellprofiler: Image Analysis Software for Identifying and Quantifying Cell Phenotypes", Genome Biology, 7(10):R100 (11 pages).
Catuogno et al., (2011) "Recent Advance in Biosensors for MicroRNAs Detection in Cancer", Cancers, 3(2):1877-1898.
Chen et al., (2018) "Efficient in Situ Barcode Sequencing Using Padlock Probe-based BaristaSeq", Nucleic Acids Research, 46(4):Article e22 (pp. 1-10).
Chen et al., (Jan. 30, 2015) "Optical imaging. Expansion Microscopy", Science, 347(6221):543-548 (13 pages).
Chen et al., (2015) "RNA Imaging. Spatially Resolved, Highly Multiplexed RNA Profiling in Single Cells", Science, 348(6233) :aaa6090.
Christian et al., (Dec. 4, 2001) "Detection of DNA Point Mutations and mRNA Expression Levels By Rolling Circle Amplification in Individual Cells", PNAS USA, 98(25):14238-14243.
Daigeler et al., (2006) "Clinicopathological Findings In A Case Series Of Extrathoracic Solitary Fibrous Tumors of Soft Tissues", BMC surgery, 6:1-8.
Basiji David, (Apr. 1, 2007) "Multispectral Imaging Flow Cytometry", Biomedical Imaging: From Nano To Macro, 1100-1103.
Denkert et al., (2015) "Strategies For Developing Ki67 As A Useful Biomarker In Breast Cancer", The Breast, 24:S67-S72.
Dirks et al., (2004) "Triggered Amplification By Hybridization Chain Reaction", Proceedings of the National Academy of Sciences of the United States of America, 101(43):15275-15278.
Drmanac et al., (Jan. 1998) "Accurate Sequencing by Hybridization For DNA Diagnostics and Individual Genomics", Nature Biotechnology, 16(1):54-58.
Edelman et al., (1997) "The Utility of Follow-up Testing After Curative Cancer Therapy: A Critical Review and Economic Analysis", JGIM, 12(5):318-331.
El-Sagheer et al., (Mar. 22, 2012) "Click Nucleic Acid Ligation: Applications in Biology and Nanotechnology", Accounts of Chemical Research, 45(8):1258-1267.
Fan et al., (2018) "Branched Rolling Circle Amplification Method for Measuring Serum Circulating MicroRNA Levels for Early Breast Cancer Detection", Cancer Science, 109(9):2897-2906.
Feeney et al., (Apr. 1, 1982) "Chemical Modification of Proteins: An Overview", Advances in Chemistry Series, 198:3-55.
Fijnvandraat et al., (2002) "Non-Radioactive In Situ Detection of mRNA in ES CellDerived Cardiomyocytes and in the Developing Heart", Microscopy Research and Techniques, 58:387-394.
Fodor et al., (Feb. 15, 1991) "Light-Directed, Spatially Addressable Parallel Chemical Synthesis", Science, 251(4995):767-773.
Fredriksson et al., (2007) "Multiplexed protein detection by proximity ligation for cancer biomarker validation", Nature methods, 4(4):327-329.
Fredriksson et al., (2002) "Protein Detection Using Proximity-Dependent DNA Ligation Assays", Nature biotechnology, 20(5):473-477.
Ganusov et al., (Dec. 2007) "Do Most Lymphocytes in Humans Really Reside in the Gut?", Trends Immunology, 28(12):514-518.
Gao et al., (Dec. 2019) "Rolling circle Amplification for Single Cell Analysis and in situ Sequencing", Trends in Analytical Chemistry, vol. 121:115700 (7 pages).
Gelali et al., (Apr. 9, 2019) "iFISH is a Publically Available Resource Enabling Versatile Dna Fish to Study Genome Architecture", Nature communications, 10(1):1636 (15 pages).
Gore et al., (Mar. 3, 2011) "Somatic Coding Mutations in Human Induced Pluripotent Stem Cells", Nature, 471(7336):63-67 (14 pages).
Gullberg et al., (Jun. 1, 2004) "Cytokine Detection By Antibody-Based Proximity Ligation", PNAS, 101 (22): 8420-8424.
Guo et al., (Jul. 8, 2008) "Four-Color DNA Sequencing With 3'—O—Modified Nucleotide Reversible Terminators and Chemically Cleavable Fluorescent Dideoxynucleotides", Proceedings of the National Academy of Sciences of the United States of America, 105(27):9145-9150.
Gyllborg et al., (2020) "Hybridization-based in situ sequencing (HybISS) for spatially resolved transcriptomics in human and mouse brain tissue", Nucleic Acids Research, 48(19):e112.
Hagai et al., (Oct. 24, 2018) "Gene Expression Variability Across Cells and Species Shapes Innate Immunity", Nature, 563(7730):197-202.
Hamady et al., (Mar. 2008) "Error-Correcting Barcoded Primers for Pyrosequencing Hundreds of Samples in Multiplex", Nature Methods, 5(3):235-237.
Hamilton Nicholas, (Aug. 2009) "Quantification and its Applications in Fluorescent Microscopy Imaging", Traffic, 10(8):951-961.
Hardenbol et al., (2003) "Multiplexed Genotyping with Sequence-Tagged Molecular Inversion Probes", Nature Biotechnology, 21(6):673-678.
Heintzmann et al., (2017) "Super-Resolution Structured Illumination Microscopy", Chemical Reviews, 117(23):13890-13908.
Hu et al., (2014) "Sensitive Quantification of Messenger RNA with a Real-Time Ligase Chain Reaction by Using a Ribonucleotide-Modified DNA Probe", Chemical Communications, 50(86):13093-13095.
Jeong et al., (2020) "Current Immunoassay Methods and Their Applications to Clinically Used Biomarkers of Breast Cancer", Clinical Biochemistry, 78:43-57.
Kappler et al., (Aug. 2020) "Emergence and Significance of Carbohydrate-specific Antibodies", Genes & Immunity, 21(4):224-239.
Kato et al., (Feb. 1, 1995) "Polymerization of Methyl Methacrylate with the Carbon Tetrachloride/Dichlorotris (triphenylphosphine)ruthenium(II)/Methylaluminum Bis(2,6-di-tert-butylphenoxide) Initiating System: Possibility of Living Radical Polymerization", Macromolecules, 28(5):1721-1723.

(56) References Cited

OTHER PUBLICATIONS

Ke et al., (2013) "In Situ Sequencing for RNA Analysis in Preserved Tissue and Cells", Nature methods, 10(9):857-860.
Klein et al., (Jul. 25, 2017) "InDrops and Drop-seq Technologies for Single-cell Sequencing", Lab on a Chip, 17(15):2540-2541.
Kobori et al., (2014) "Expanding possibilities of rolling circle amplification as a biosensing platform", Analytical Sciences, 30(1):59-64.
Krzywkowski et al., (2019) "Chimeric Padlock and llock Probes for Increased Efficiency of Targeted RNA Detection", RNA, 25(1):82-89.
Lage et al., (Feb. 2003) "Whole Genome Analysis Of Genetic Alterations In Small DNA Samples Using Hyperbranched Strand Displacement Amplification And Array-CGH", Genome Research, 13(2):294-307.
Lareau et al., (Feb. 13, 2020) "Inference and Effects of Barcode Multiplets in Droplet-based Single-cell Assays", Nature Communications, 11(1):866 (1-9).
Larsson et al., (Apr. 11, 2010) "In Situ Detection and Genotyping of Individual mRNA Molecules", Nature methods, 7(5):395-397.
Lee et al., (Mar. 2015) "Fluorescent in situ sequencing (FISSEQ) of RNA for gene expression profiling in intact cells and tissues", Nature Protocols, 10(3):442-458.
Lee et al., (2014) "Highly multiplexed subcellular RNA sequencing in situ", Science, 343(6177):1360-1363.
Li et al., (May 29, 2009) "Genome-Wide Identification of Human RNA Editing Sites by Parallel DNA Capturing and Sequencing", Science, 324(5931): 1210-1213 (5 pages).
Li et al., (Jun. 12, 2009) "Multiplex Padlock Targeted Sequencing Reveals Human Hypermutable CpG Variations", Genome research, 19(9):1606-1615.
Li et al., (2009) "Stand-Alone Rolling Circle Amplification Combined with Capillary Electrophoresis for Specific Detection of Small RNA", Analytical Chemistry, 81:4906-4913.
Lizardi et al., (Jul. 1998) "Mutation Detection and Single-Molecule Counting Using Isothermal Rolling-Circle Amplification", Nature Genetics, 19(3):225-232.
Lohmann et al., (2007) "Detection of short repeated genomic sequences on metaphase chromosomes using padlock probes and target primed rolling circle DNA synthesis", BMC molecular biology, 8:103 (8 pages).
Lubeck et al., (2014) "Single-cell in Situ RNA Profiling by Sequential Hybridization", Nature Methods, 11(4):360-361.
Lubeck et al., (2012) "Single-cell Systems Biology by Super-resolution Imaging and Combinatorial Labeling", Nature Methods, 9(7):743-748.
Lugagne et al., (Jul. 30, 2018) "Identification of Individual Cells from z-stacks of Bright-field Microscopy Images", Scientific Reports, 8:11455 (5 pages).
Lundin et al., (2020) "Spatiotemporal Mapping of RNA Editing in the Developing Mouse Brain Using in Situ Sequencing Reveals Regional and Cell-type-specific Regulation", BMC Biology, 18(6):1-15.
Mag et al., (Nov. 24, 1992) "Synthesis and Selective Cleavage of an Oligodeoxynucleotide Containing a Bridged Non-chiral Internucleotide 3'-phosphoramidate Linkage", Tetrahedron Letters, 33(48):7319-7322.
Magaki et al., (2019) "An Introduction To The Performance Of Immunohistochemistry", Methods in Molecular Biology, 1897:289-298.
Manoharan Vinothan N., (2010) "Digital Holographic Microscopy for 3D Imaging of Complex Fluids and Biological Systems National Academies of Sciences", Engineering, and Medicine. 2010. Frontiers of Engineering: Reports on Leading-Edge Engineering from the 2009 Symposium. Washington, DC: T, National Academies of Sciences, Engineering, and Medicine, 8 pages.
Manuguerra et al., (May 1, 2018) "Gene Assembly via One-pot Chemical Ligation of DNA Promoted by DNA Nanostructures", Chemical Communications, 54(36):4529-4532.

Mignardi et al., (Apr. 2, 2014) "Fourth-Generation Sequencing in the Cell and the Clinic", Genome Medicine, 6(31):1-4.
Mirza et al., (Mar. 14, 2008) "Methods and Approaches for the Comprehensive Characterization and Quantification of Cellular Proteomes Using Mass Spectrometry", Physiological Genomics, 33(1):3-11.
Mitra et al., (2003) "Fluorescent In Situ Sequencing on Polymerase Colonies", Analytical Biochemistry, 320:55-65.
Moad et al., (Jun. 14, 2005) "Living Radical Polymerization by the RAFT Process", Australian Journal of Chemistry, 58(6):379-410.
Mohammadi-Kambs et al., (2017) "Hamming Distance as a Concept in DNA Molecular Recognition", ACS Omega, 2(4):1302-1308.
Nilsson et al., (Sep. 30, 1994) "Padlock Probes: Circularizing Oligonucleotides For Localized DNA Detection", Science, 265(5181):2085-2088 (5 pages).
Nitta et al., (2013) "New Methods for ALK Status Diagnosis in Non-Small-Cell Lung Cancer", Journal of Thoracic Oncology, 8(8):1019-1031 (13 pages).
Noggle et al., (Oct. 5, 2011) "Human Oocytes Reprogram Somatic Cells to a Pluripotent State", Nature, 478(7367):70-75.
Odeh et al., (Dec. 18, 2019) "Aptamers Chemistry: Chemical Modifications and Conjugation Strategies", Molecules, 25(1):3 (51 pages).
Otsu et al., (Feb. 16, 1982) "Role of initiator-transfer agent-terminator (iniferter) in radical polymerizations: Polymer design by organic disulfides as iniferters", Macromolecular Rapid Communications, 3:127-132.
Ouladan et al., (2015) "Differential diagnosis of solitary fibrous tumors: A study of 454 soft tissue tumors indicating the diagnostic value of nuclear State relocation and ALDH1 expression combined with in situ proximity ligation assay", International journal of oncology, 46(6):2595-2605.
Park et al., (2013) "The role of chemotherapy in advanced solitary fibrous tumors: a retrospective analysis", Clinical sarcoma research, 3(1):1-7.
Patel et al., (Jun. 12, 2014) "Single-cell RNA-seq Highlights Intratumoral Heterogeneity in Primary Glioblastoma", Science, 344(6190):1396-1401.
Pattarone et al., (2021) "Learning Deep Features for Dead and Living Breast Cancer cell Classification without Staining", Scientific Reports, 11:10304 (10 pages).
Pearson et al., (May 13, 2016) "High-Level Clonal FGFR Amplification and Response to FGFR Inhibition in a Translational Clinical Trial", Cancer Discovery, 6(8):838-851.
Peerzade et al., (May 8, 2020) "Ultrabright Fluorescent Silica Nanoparticles for Multiplexed Detection", Nanomaterials, 10(5):905 (14 pages).
Peters et al., (Jan. 2011) "Multiparameter Flow Cytometry in the Diagnosis and Management of Acute Leukemia", Archives of Pathology & Laboratory Medicine, 135(1):44-54.
Porreca et al., (Nov. 2007) "Multiplex Amplification of Large Sets of Human Exons", Nature Methods, 4(11):931-936.
Ronaghi et al., (Jul. 17, 1998) "A Sequencing Method Based on Real-Time Pyrophosphate", Science, 281(5375):363-365.
Ronaghi et al., (Nov. 1, 1996) "Real-Time DNA Sequencing Using Detection of Pyrophosphate Release", Analytical Biochemistry, 242(1):84-89.
Ronaghi Mostafa, (2001) "Pyrosequencing Sheds Light on DNA Sequencing", Genome Research, 11(1):3-11.
Rouhanifard, (2018) "Exponential Fluorescent Amplification of Individual RNAs Using ClampFISH probes", bioRxiv Preprint, Article 222794.
Sansone et al., (Jun. 2019) "Spatial Transcriptomics Levels Up", Nature Methods, 16(6):458 (1 page).
Sapoznik et al., (2020) "A Versatile Oblique Plane Microscope for Large-scale and High-resolution Imaging of Subcellular Dynamics", Cell Biology, 9:e57681 (39 pages).
Schallmeiner et al., (2007) "Sensitive protein detection via triple-binder proximity ligation assays", Nature methods, 4(2):135-137.
Schlachter et al., (2009) "A Method to Unmix Multiple Fluorophores in Microscopy Images with Minimal a Priori Information", Optics Express, 17(25):22747-22760.

(56) References Cited

OTHER PUBLICATIONS

Shendure et al., (2005) "Accurate Multiplex Polony Sequencing of an Evolved Bacterial Genome", Science, 309(5741):1728-1732.
Shirawaka et al., (2004) "Blind Spectral Decomposition of Single-Cell Fluorescence by Parallel Factor Analysis", Biophysical Journal, 86(3):1739-1752.
Strell et al., (2019) "Placing RNA in Context and Space—Methods for Spatially Resolved Transcriptomics", The FEBS Journal, 286(8):1468-1481.
Suzuki et al., (Dec. 20, 2019) "Characterization Of Cancer Omics And Drug Perturbations In Panels Of Lung Cancer Cells", Sci. Rep, 9(1):19529 (15 pages).
Takahashi et al., (2018) "RNase H-assisted RNA-Primed Rolling Circle Amplification for Targeted RNA Sequence Detection", Scientific Reports, 8:7770 (11 pages).
Tang et al., (2016) "Suppression of Rolling Circle Amplification by Nucleotide Analogs in Circular Template for Three DNA Polymerases", Bioscience, biotechnology, and biochemistry, 80(8):1555-1561.
Turczyk et al., (2020) "Spatial Sequencing: A Perspective", Journal of biomolecular techniques: JBT, 31(2):44-46.
Van Der Velden et al., (Jun. 2003) "Detection of minimal residual disease in hematologic malignancies by real-time quantitative PCR: principles, approaches, and laboratory aspects", Leukemia, 17(6):1013-1034.
Veregin et al., (Sep. 1, 1993) "Free radical polymerizations for narrow polydispersity resins: electron spin resonance studies of the kinetics and mechanism", Macromolecules, 26(20):5316-5320.
Vickovic et al., (Oct. 2019) "High-definition Spatial Transcriptomics for in Situ Tissue Profiling", Nature Methods, 16(10):987-990 (14 pages).
Walker et al., (Oct. 1, 1988) "Photolabile 1-(2-Nitrophenyl) Ethyl Phosphate Esters of Adenine Nucleotide Analogs. Synthesis and Mechanism of Photolysis", Journal of the American Chemical Society, 110(21):7170-7177.
Wang et al., (May 1, 1995) "Controlled/living radical polymerization. atom transfer radical polymerization in the presence of transition-metal complexes", Macromolecules, 117(20):5614-5615.
Wang et al., (Mar. 19, 2018) "Multiplexed Imaging of High-density Libraries of RNAs with Merfish and Expansion Microscopy", Scientific Reports, 8(1):4847 (1-13).
Wang et al., (Jul. 27, 2018) "Three-dimensional Intact-tissue Sequencing of Single-cell Transcriptional States", Science, 361(6400):5691 (11 pages).
Wassie et al., (2019) "Expansion Microscopy: Principles and Uses in Biological Research", Nature methods, 16(1):33-41.
Weibrecht et al., (2013) "In Situ Detection of Individual mRNA Molecules and Protein Complexes or Post-Translational Modifications Using Padlock Probes Combined with the In Situ Proximity Ligation Assay.", Nature Protocols, 8(2):355-372.
Wilson et al., (Jul. 15, 2006) "Gene Expression Profiling of Adult Acute Myeloid Leukemia Identifies Novel Biologic Clusters for Risk Classification and Outcome Prediction", Blood, 108(2):685-696.
Xu et al., (2009) "Design of 240,000 Orthogonal 25mer DNA Barcode Probes", PNAS, 106(7):2289-2294.
Yaari et al., (Nov. 20, 2015) "Practical Guidelines For B-cell Receptor Repertoire Sequencing Analysis", Genome Medicine, 7:121(14 pages).
Yeole N., (May 25, 2010) "Thiocarbonylthio Compounds", Synlett, 10:1572-1573.
York et al., (Nov. 2013) "Instant super- Resolution Imaging in Live Cells and Embryos via Analog Image Processing", Nature Methods, 10(11):1122-1126 (19 pages).
Zhang et al., (Aug. 2009) "Digital RNA Allelotyping Reveals Tissue-specific and Allele- specific Gene Expression in Human", Nature Methods, 6(8):613-618 (14 pages).
Zheng et al., (Jan. 2017) "Massively Parallel Digital Transcriptional Profiling of Single Cells", Nature Communications, 8:14049 (12 pages).

\* cited by examiner

Universal readout

Complete profile of every individual cell

Spatial data
- ☐ Cell morphology
- ☐ Target localization
- ☐ Intracellular
- ☐ Cell surface
- ☐ Secreted proteins

------

Targeted panels
- ☐ RNA transcription
- ☐ Protein expression
- ☐ RNA gene sequence

FIG. 1B

| | |
|---|---|
| Integrated detection | In-situ sequencing of individual cells |
| Cell capture efficiency | 100%: No loss of cells because cell capture methods not used |
| Gene transcription assays | Targeted panels |
| Protein expression | 10-100s of proteins |
| # of cells/sample | 10-100 thousand cells per well |
| Throughput | 96 samples at a time |
| Total cells per run | 1-10 million cells |
| Cell visualization | Visual data on individual cell morphology |
| Cost | Significantly lower cost per cell including NGS |

FIG. 2

MULTIOMIC ANALYSIS DEVICE AND METHODS OF USE THEREOF

CROSS-REFERENCES TO RELATED APPLICATIONS

This application is a continuation of U.S. application Ser. No. 18/352,957, filed Jul. 14, 2023, which is a continuation of PCT Application PCT/US2022/027630, filed May 4, 2022, which claims the benefit of U.S. Provisional Application No. 63/184,684, filed May 5, 2021, each of which is incorporated herein by reference in their entirety and for all purposes.

BACKGROUND

The genomic tools and technologies developed over the last two decades since the first sequencing of the human genome have greatly improved our understanding of biology, empowered the development of novel therapies, and advanced clinical diagnostics. Current sequencing technologies and products have made a significant impact, but real limitations remain to incorporate these tools into routine clinical practice. Advanced molecular technologies are required to enable a high-resolution view of DNA, RNA, and proteins in individual cells, along with their spatial arrangement, shedding greater insight into the function of both cells and tissues. Multiomics is a biological analysis approach that unifies the study of traditionally separate and distinct data sets derived from different "omes" (e.g., genomes, proteomes, transcriptomes, epigenomes, metabolomes, and microbiomes). By combining these "omes" it is possible to analyze complex biological processes to find novel associations between biological entities, identify relevant biomarkers, and build revelatory signatures of disease and physiology.

Single-cell technologies have emerged to enable profiling the composition of the genome, epigenome, transcriptome, or proteome of a single cell. Uncovering the distribution, heterogeneity, spatial gene and protein co-expression patterns within cells and tissues is vital for understanding how cell co-localization influences tissue development and the spread of diseases such as cancer, which could lead to important new discoveries and therapeutics. Quantifying gene and protein expression and obtaining precise sequencing information enables precise identification, monitoring, and possible treatment at the molecular level. Disclosed herein, inter alia, are solutions to these and other problems in the art.

BRIEF SUMMARY

In an aspect is provided a device, compositions, and kits for performing single cell analysis, spatial analysis, genomic analysis, and proteomics. In embodiments, the device, compositions, and kits provide a high-resolution view of biology at the single cell and tissue level. In embodiments, the device, compositions, and kits provide a versatile platform capable of measuring levels of RNA transcription, protein expression and sequence specific information directly in cells and tissues.

BRIEF DESCRIPTION OF THE DRAWINGS

FIGS. 1A and 1B provide a schematic overview of a multiomic analysis provided by the devices, compositions, kits, and methods described herein. FIG. 1A illustrates a 96-well plate including 100,000 cells per well, wherein parallel in situ detection of RNA and protein is performing using the devices, compositions, kits, and methods described herein. FIG. 1B shows an overview of the information that may be obtained in every individual cell via multiomic analyses as described herein.

FIG. 2 shows a summary table of some example performance metrics of the device described herein.

FIG. 8A shows a healthy human kidney section with multiplexed detection of 28 transcriptional targets (i.e., 28 different mRNA genes of interest). Each dot identifies one detected transcript (e.g., dots of the same color/shade are the same gene). The transcripts detected in this experiment include the ALDOB, GATM, LRP2, UMOD, CUBN, SPP1, MIOX, CALB1, PODXL, ATP6VOD2, SLC12A1, AQP3, NPHS2, AQP2, VCAM1, TAGLN, ACTA2, PDGFRB, FLT1, SLC4A1, SLC26A4, PECAM1, EMCN, SLC12AM, CLIC5, SLC4A9, SLC13A1, and TRPV5 genes. Identified transcripts are overlaid on an eosin-stained tissue sample to orient the user. Eosin is a stain which identifies cytoplasm of cells. The two insets are magnified (i.e., zoomed in) of two sub regions show that tissue specific transcripts are localized with contiguous and discrete and eosin regions. The obtained image on the left indicates a Field of View (FoV) of about 360 μm×about 360 μm. FIG. 8B shows a healthy human kidney section with both transcript (i.e., RNA) and protein detection multiplexed in the same experiment, all detected via in situ sequencing using the device as described herein. The detected genes were found to colocalize with two proteins of interest (proteins PODXL and PVALB). The transcripts detected include the following genes: UMOD, CALB1, PODXL, ALC12A1, AQP3, NPHS2, AQP2, and SLC4A1. The two proteins are expected to be associated with spatially distinct structures and clearly colocalize with expected transcripts. The obtained images indicate a Field of View (FoV) of about 360 µm×about 360 µm. FIG. 8C shows a healthy human kidney section with cell segmentation (i.e., cell outlines drawn in the image). Using the collective information and data from the detected genes and proteins, a resulting image is compiled providing information on the structure, location, and types of cells present within the tissue. The resulting image of cell outlines provides information on the cell type and tissue location, indicating cells within the intermediate tubules, distal tubules, collecting duct, glomerulus, and proximal tubules overlaid on the image of the tissue sample.

FIG. 9B shows the four insets from FIG. 9A (bottom) and the mRNA transcript detection of the human kidney tumor section. A total of 105 transcriptional targets were targeted and identified in this experiment. Each dot identifies one detected transcript, and each transcript is assigned to a particular structure and/or location within the kidney. Going from left to right, a change in morphology is clearly observed, transitioning from relatively healthy and structured on the left to diseased and unstructured on the right; this corresponds with the change in spatial transcriptional profile from structured to unstructured. Different structures visible in the image correspond to different transcriptional profiles. The gene targets identified in this experiment outline the proximal tubule, renal corpuscle/glomerulus, vessels, interstitium, collecting tubules, intermediate tubules, and distal tubules. The tubule regions with denser nuclei in the leftmost bottom image correspond to collecting tubules, whereas tubules with lower nuclei density correspond to proximal tubules. In the center (leftmost images) is a round shape of clearly different morphology than the tubules corresponding to a glomerulus, which is filled with podocytes and vessels. These structures are confirmed in the transcriptional analysis (top images) by detecting the genes only found in those structures. Each Field of View (FoV) is about 360 µm×about 360 µm.

DETAILED DESCRIPTION

Figure 1A:
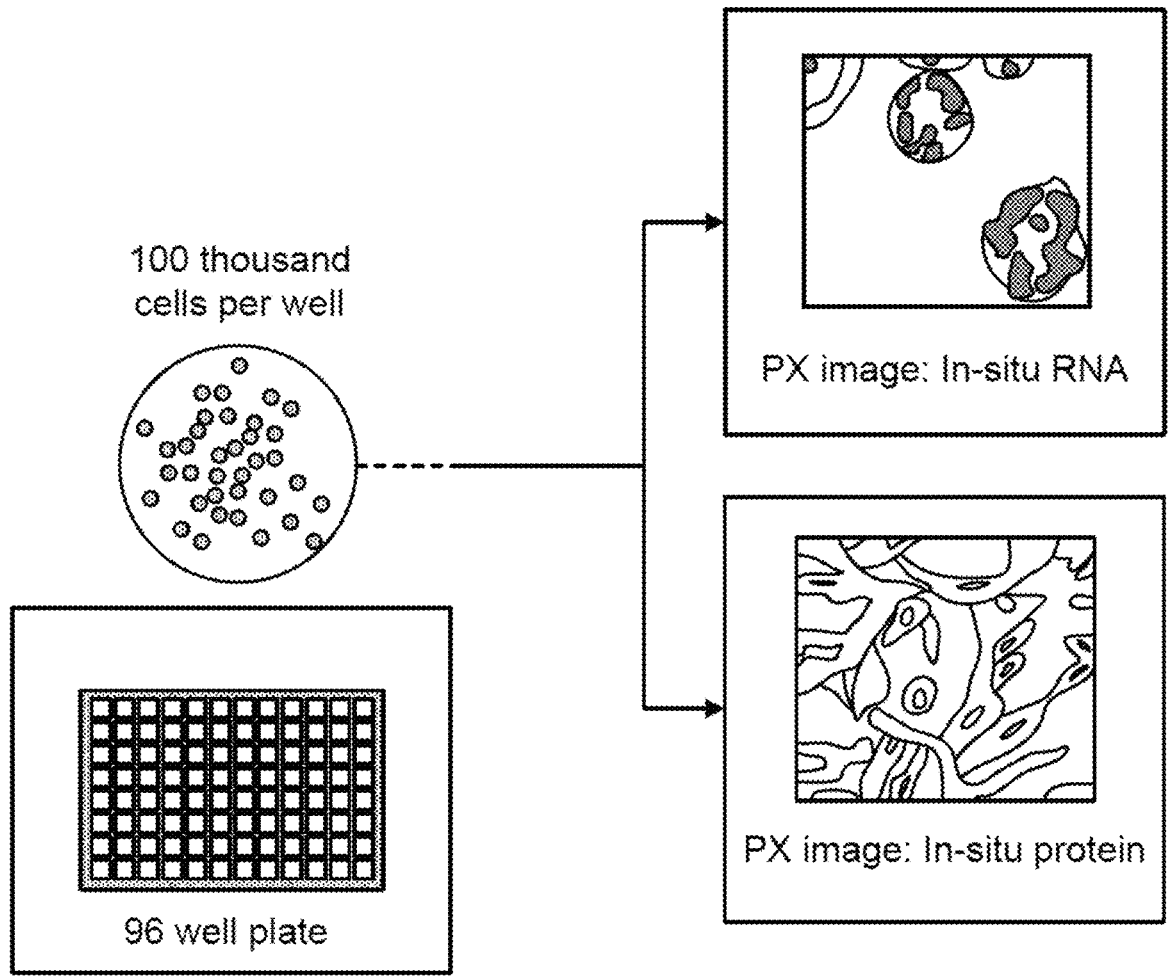

The aspects and embodiments described herein relate to an integrated solution providing a panoply of information about a sample (e.g., a cell or tissue sample). For example, the device described herein is capable of i) in situ single cell analysis; ii) in situ tissue analysis; and iii) sequencing (e.g., RNA-seq or immune repertoire sequencing). In embodiments, the device is configured to provide RNA transcription analysis (e.g., counting RNA) for targeted panels; serological analyses, protein expression analysis (e.g., counting of proteins) for targeted panels; and/or sequencing variable regions in immune cells (e.g., B-cells or T-cells) or cancer cells. Utilizing the device and methods described herein, that is, combining cell morphology information with standard marker-based assessment provides improved specificity of detection, thereby enabling a lower limit of detection and improved diagnoses of diseases.

I. Definitions

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms "a", "an", and "the" include the plural reference unless the context clearly indicates otherwise. Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure, or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

The terms "attached," "bind," and "bound" as used herein are used in accordance with their plain and ordinary meanings and refer to an association between atoms or molecules. The association can be direct or indirect. For example, attached molecules may be directly bound to one another, e.g., by a covalent bond or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). As a further example, two molecules may be bound indirectly to one another by way of direct binding to one or more intermediate molecules, thereby forming a complex.

"Specific binding" is where the binding is selective between two molecules. A particular example of specific binding is that which occurs between an antibody and an antigen. Typically, specific binding can be distinguished from non-specific when the dissociation constant (KD) is less than about $1 \times 10^{-5}$ M or less than about $1 \times 10^{-6}$ M or $1 \times 10^{-7}$ M. Specific binding can be detected, for example, by ELISA, immunoprecipitation, coprecipitation, with or without chemical crosslinking, two-hybrid assays and the like. In embodiments, the $K_D$ (dissociation constant) o between two specific binding molecules is less than $10^{-6}$ M, less than $10^{-7}$ M, less than $10^{-8}$M, less than $10^{-9}$M, less than $10^{-9}$M, less than $10^{-11}$ M, or less than about $10^{-12}$ M or less.

As used herein, the term "complement," as used herein, refers to a nucleotide (e.g., RNA or DNA) or a sequence of nucleotides capable of base pairing with a complementary nucleotide or sequence of nucleotides. For example, complementarity exists between the two strands of a double stranded DNA molecule or between an oligonucleotide primer and a primer binding site on a single stranded nucleic acid when a nucleotide (e.g., RNA or DNA) or a sequence of nucleotides is capable of base pairing with a respective cognate nucleotide or cognate sequence of nucleotides. As described herein and commonly known in the art the complementary (matching) nucleotide of adenosine is thymidine and the complementary (matching) nucleotide of guanosine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence, only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and anti-sense sequences, wherein the sense sequence contains complementary nucleotides to the antisense sequence and thus forms the complement of the antisense sequence. Another example of complementary sequences are a template sequence and an amplicon sequence polymerized by a polymerase along the template sequence. "Duplex" means at least two oligonucleotides and/or polynucleotides that are fully or partially complementary undergo Watson-Crick type base pairing among all or most of their nucleotides so that a stable complex is formed.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, one or both sequences in a pair of complementary sequences form portions of longer polynucleotides, which may or may not include additional regions of complementarity.

As used herein, the term "hybridize" or "specifically hybridize" refers to a process where two complementary nucleic acid strands anneal to each other under appropriately stringent conditions. Hybridizations are typically and preferably conducted with oligonucleotides. Non-limiting examples of nucleic acid hybridization techniques are described in, for example, Sambrook, et al., Molecular Cloning: A Laboratory Manual (2nd Edition, 1989). Those skilled in the art understand how to estimate and adjust the stringency of hybridization conditions such that sequences having at least a desired level of complementarity will stably hybridize, while those having lower complementarity will not. Hybridization reactions can be performed under conditions of different "stringency". For example, a low stringency hybridization reaction is carried out at about 40° C. in 10×SSC. A moderate stringency hybridization may be performed at about 50° C. in 6×SSC. A high stringency hybridization reaction is generally performed at about 60° C. in 1×SSC. Hybridization reactions can also be performed under "physiological conditions" which is known to one skilled in the art (e.g., a physiological condition is the temperature, ionic strength, pH and concentration of $Mg^{2+}$ normally found in vivo).

As used herein, the term "nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA with linear or circular framework. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

As used herein, the term "polynucleotide template" refers to any polynucleotide molecule that may be bound by a polymerase and utilized as a template for nucleic acid synthesis. As used herein, the term "polynucleotide primer" refers to any polynucleotide molecule that may hybridize to a polynucleotide template, be bound by a polymerase, and be extended in a template-directed process for nucleic acid synthesis, such as in a PCR or sequencing reaction. Polynucleotide primers attached to a core polymer within a core are referred to as "core polynucleotide primers." A primer can be of any length depending on the particular technique it will be used for. For example, amplification primers are generally between 10 and 40 nucleotides in length. The length and complexity of the nucleic acid fixed onto the nucleic acid template may vary. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer. In embodiments, a primer is hybridized to a target polynucleotide.

As used herein, the term "template polynucleotide" refers to any polynucleotide molecule that may be bound by a polymerase and utilized as a template for nucleic acid synthesis. In general, the terms "target polynucleotide" and "target nucleic acid" are used interchangeably herein refer to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction. A target polynucleotide is not necessarily any single molecule or sequence. For example, a target polynucleotide may be any one of a plurality of target polynucleotides in a reaction, or all polynucleotides in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. As yet another example, all or a subset of polynucleotides in a sample may be modified by the addition of a primer-binding sequence (such as by the ligation of adapters containing the primer binding sequence), rendering each modified polynucleotide a target polynucleotide in a reaction with the corresponding primer polynucleotide(s). In embodiments, the template polynucleotide includes a target nucleic acid sequence and one or more barcode sequences. In embodiments, the template polynucleotide is a barcode sequence.

The term "adapter" as used herein refers to any linear oligonucleotide that can be ligated to a nucleic acid molecule, thereby generating nucleic acid products that can be sequenced on a sequencing platform (e.g., an Illumina™ or Singular Genomics™ sequencing platform). In embodiments, adapters include two reverse complementary oligonucleotides forming a double-stranded structure. In embodiments, an adapter includes two oligonucleotides that are complementary at one portion and mismatched at another portion, forming a Y-shaped or fork-shaped adapter that is double stranded at the complementary portion and has two overhangs at the mismatched portion. Since Y-shaped adapters have a complementary, double-stranded region, they can be considered a special form of double-stranded adapters. When this disclosure contrasts Y-shaped adapters and double stranded adapters, the term "double-stranded adapter" or "blunt-ended" is used to refer to an adapter having two strands that are fully complementary, substantially (e.g., more than 90% or 95%) complementary, or partially complementary. In embodiments, adapters include sequences that bind to sequencing primers. In embodiments, adapters include sequences that bind to immobilized oligonucleotides (e.g., primer sequences) or reverse complements thereof. In embodiments, the adapter is substantially non-complementary to the 3' end or the 5' end of any target polynucleotide present in the sample. In embodiments, the adapter can include a sequence that is substantially identical, or substantially complementary, to at least a portion of a primer, for example a universal primer. In embodiments, the adapter can include an index sequence (also referred to as barcode or tag) to assist with downstream error correction, identification or sequencing. Illumina is a registered trademark of Illumina, Inc Singular Genomics is a trademark of Singular Genomics Systems, Inc.

As used herein, the terms "oligonucleotide primer" and "polynucleotide primer" and "primer" refer to any polynucleotide molecule that may hybridize to a polynucleotide template, be bound by a polymerase, and be extended in a template-directed process for nucleic acid synthesis. The primer may be a separate polynucleotide from the polynucleotide template, or both may be portions of the same polynucleotide (e.g., as in a hairpin structure having a 3' end that is extended along another portion of the polynucleotide to extend a double-stranded portion of the hairpin. A primer can be of any length depending on the particular technique it will be used for. For example, amplification primers are generally between 10 and 40 nucleotides in length. The length and complexity of the primer onto the nucleic acid template may vary. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment the primer is a DNA primer, i.e., a primer consisting of, or largely consisting of, deoxyribonucleotide residues. The primers are designed to have a sequence that is the complement of a region of template polynucleotide (e.g., a padlock probe) to which the primer hybridizes. The addition of a nucleotide residue to the 3' end of a primer by formation of a phosphodiester bond results in an extension product. The addition of a nucleotide residue to the 3' end of the extension product by formation of a phosphodiester bond results in a further extension product. In another embodiment the primer is an RNA primer. In embodiments, a primer is hybridized to a target polynucleotide. A "primer" is complementary to a polynucleotide template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis. A primer typically has a length of 10 to 50 nucleotides. For example, a primer may have a length of 10 to 40, 10 to 30, 10 to 20, 25 to 50, 15 to 40, 15 to 30, 20 to 50, 20 to 40, or 20 to 30 nucleotides. In some embodiments, a primer has a length of 18 to 24 nucleotides. Examples of primers include, but are not limited to, P5 primer, P7 primer, PE1 primer, PE2 primer, A19 primer, or others known in the art.

The term "messenger RNA" or "mRNA" refers to an RNA that is without introns and is capable of being translated into a polypeptide. The term "RNA" refers to any ribonucleic acid, including but not limited to mRNA, tRNA (transfer RNA), rRNA (ribosomal RNA), and/or noncoding RNA (such as lncRNA (long noncoding RNA)). The term "cDNA" refers to a DNA that is complementary or identical to an RNA, in either single stranded or double stranded form.

As used herein, the term "DNA polymerase" and "nucleic acid polymerase" are used in accordance with their plain ordinary meanings and refer to enzymes capable of synthesizing nucleic acid molecules from nucleotides (e.g., deoxyribonucleotides). Exemplary types of polymerases that may be used in the compositions and methods of the present disclosure include the nucleic acid polymerases such as DNA polymerase, DNA- or RNA-dependent RNA polymerase, and reverse transcriptase. In some cases, the DNA polymerase is 9° N polymerase or a variant thereof, E. Coli DNA polymerase I, Bacteriophage T4 DNA polymerase, Sequenase™, Taq DNA polymerase, DNA polymerase from Bacillus stearothermophilus, Bst 2.0 DNA polymerase, 9° N polymerase (exo–)A485L/Y409V, Phi29 DNA Polymerase (φ29 DNA Polymerase), T7 DNA polymerase, DNA polymerase II, DNA polymerase III holoenzyme, DNA polymerase IV, DNA polymerase V, VentR DNA polymerase, Therminator™ II DNA Polymerase, Therminator™ III DNA Polymerase, or or Therminator™ IX DNA Polymerase. In embodiments, the polymerase is a protein polymerase. Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g. Therminator™ γ, 9° N polymerase (exo–), Therminator™ II, Therminator™ III, or Therminator™ IX).

In embodiments, the DNA polymerase is a modified archaeal DNA polymerase. In embodiments, the polymerase is a reverse transcriptase. In embodiments, the polymerase is a mutant P. abyssi polymerase (e.g., such as a mutant P. abyssi polymerase described in WO 2018/148723 or WO 2020/056044).

A nucleic acid can be amplified by a suitable method. The term "amplified" as used herein refers to subjecting a target nucleic acid in a sample to a process that linearly or exponentially generates amplicon nucleic acids having the same or substantially the same (e.g., substantially identical) nucleotide sequence as the target nucleic acid, or segment thereof, and/or a complement thereof. In some embodiments an amplification reaction comprises a suitable thermal stable polymerase. Thermal stable polymerases are known in the art and are stable for prolonged periods of time, at temperature greater than 80° C. when compared to common polymerases found in most mammals. In certain embodiments the term "amplified" refers to a method that comprises a polymerase chain reaction (PCR). Conditions conducive to amplification (i.e., amplification conditions) are known and often comprise at least a suitable polymerase, a suitable template, a suitable primer or set of primers, suitable nucleotides (e.g., dNTPs), a suitable buffer, and application of suitable annealing, hybridization and/or extension times and temperatures. In certain embodiments an amplified product (e.g., an amplicon) can contain one or more additional and/or different nucleotides than the template sequence, or portion thereof, from which the amplicon was generated (e.g., a primer can contain "extra" nucleotides (such as a 5' portion that does not hybridize to the template), or one or more mismatched bases within a hybridizing portion of the primer).

As used herein, the term "rolling circle amplification (RCA)" refers to a nucleic acid amplification reaction that amplifies a circular nucleic acid template (e.g., single-stranded DNA circles) via a rolling circle mechanism. Rolling circle amplification reaction is initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). The rolling circle amplification typically produces concatemers comprising tandem repeat units of the circular nucleic acid template sequence. The rolling circle amplification may be a linear RCA (LRCA), exhibiting linear amplification kinetics (e.g., RCA using a single specific primer), or may be an exponential RCA (ERCA) exhibiting exponential amplification kinetics. Rolling circle amplification may also be performed using multiple primers (multiply primed rolling circle amplification or MPRCA) leading to hyper-branched concatemers. For example, in a double-primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a ramifying cascade of multiple-hybridization, primer-extension, and strand-displacement events involving both the primers. This often generates a discrete set of concatemeric, double-stranded nucleic acid amplification products. The rolling circle amplification may be performed in-vitro under isothermal conditions using a suitable nucleic acid polymerase such as Phi29 DNA polymerase. RCA may be performed by using any of the DNA polymerases that are known in the art (e.g., a Phi29 DNA polymerase, a Bst DNA polymerase, or SD polymerase).

A nucleic acid can be amplified by a thermocycling method or by an isothermal amplification method. In some embodiments a rolling circle amplification method is used. In some embodiments amplification takes place on a solid support (e.g., within a well of a microplate) where a nucleic acid, nucleic acid library or portion thereof is immobilized. In certain sequencing methods, a nucleic acid library is added to a microplate and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support.

In some embodiments solid phase amplification comprises a nucleic acid amplification reaction comprising only one species of oligonucleotide primer immobilized to a surface or substrate. In certain embodiments solid phase amplification comprises a plurality of different immobilized oligonucleotide primer species. In some embodiments solid phase amplification may comprise a nucleic acid amplification reaction comprising one species of oligonucleotide primer immobilized on a solid surface and a second different oligonucleotide primer species in solution. Multiple different species of immobilized or solution based primers can be used. Non-limiting examples of solid phase nucleic acid amplification reactions include interfacial amplification, bridge PCR amplification, emulsion PCR, WildFire amplification (e.g., US patent publication US20130012399), the like or combinations thereof.

"Analog," "analogue" or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound. As used herein, the term "analogue", in reference to a chemical compound, refers to a compound having a structure similar to that of another one, but differing from it in respect of one or more different atoms, functional groups, or substructures that are replaced with one or more other atoms, functional groups, or substructures. In the context of a nucleotide useful in practicing the invention, a nucleotide analog refers to a compound that, like the nucleotide of which it is an analog, can be incorporated into a nucleic acid molecule (e.g., an extension product) by a suitable polymerase, for example, a DNA polymerase in the context of a dNTP analogue. The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, e.g., see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as primers attached to a polymer. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

As used herein, the term "selective" or "selectivity" or the like of a compound refers to the substance's ability to discriminate between molecular targets. As used herein, the terms "specific", "specifically", "specificity", or the like of a compound refers to the substance's ability to cause a particular action, such as binding, to a particular molecular target with minimal or no action to other substances (e.g., an antibody and antigen).

As used herein, the term "barcode" refers to a known nucleic acid sequence that allows some feature with which the barcode is associated to be identified. Typically, a barcode is unique to a particular feature in a pool of barcodes that differ from one another in sequence, and each of which is associated with a different feature. In embodiments, barcodes are about or at least about 5, 6, 7, 8, 9, 10, 15, 20, 25, 30, 40, 50, 75 or more nucleotides in length. In embodiments, barcodes are shorter than 20, 15, 10, 9, 8, 7, 6, or 5 nucleotides in length. In embodiments, barcodes are 10-50 nucleotides in length, such as 15-40 or 20-30 nucleotides in length. In a pool of different barcodes, barcodes may have the same or different lengths. In general, barcodes are of sufficient length and comprise sequences that are sufficiently different to allow the identification of associated features (e.g., a binding moiety or analyte) based on barcodes with which they are associated. In embodiments, a barcode can be identified accurately after the mutation, insertion, or deletion of one or more nucleotides in the barcode sequence, such as the mutation, insertion, or deletion of 1, 2, 3, 4, 5, or more nucleotides. In embodiments, the barcodes are selected to form a known set of barcodes, e.g., the set of barcodes may be distinguished by a particular Hamming distance.

As used herein, the term "modified nucleotide" refers to nucleotide modified in some manner. Typically, a nucleotide contains a single 5-carbon sugar moiety, a single nitrogenous base moiety and 1 to three phosphate moieties. In embodiments, a nucleotide can include a blocking moiety (alternatively referred to herein as a reversible terminator moiety) and/or a label moiety. A blocking moiety (e.g., a reversible terminator) on a nucleotide prevents formation of a covalent bond between the 3' hydroxyl moiety of the nucleotide and the 5' phosphate of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. In embodiments, the blocking moiety is attached to the 3' oxygen of the nucleotide and is independently —NH$_2$, —CN, —CH$_3$, C$_2$-C$_6$ allyl (e.g., —CH$_2$—CH=CH$_2$), methoxyalkyl (e.g., —CH$_2$—O—CH$_3$), or —CH$_2$N$_3$. In embodiments, the blocking moiety is attached to the 3' oxygen of the nucleotide and is independently

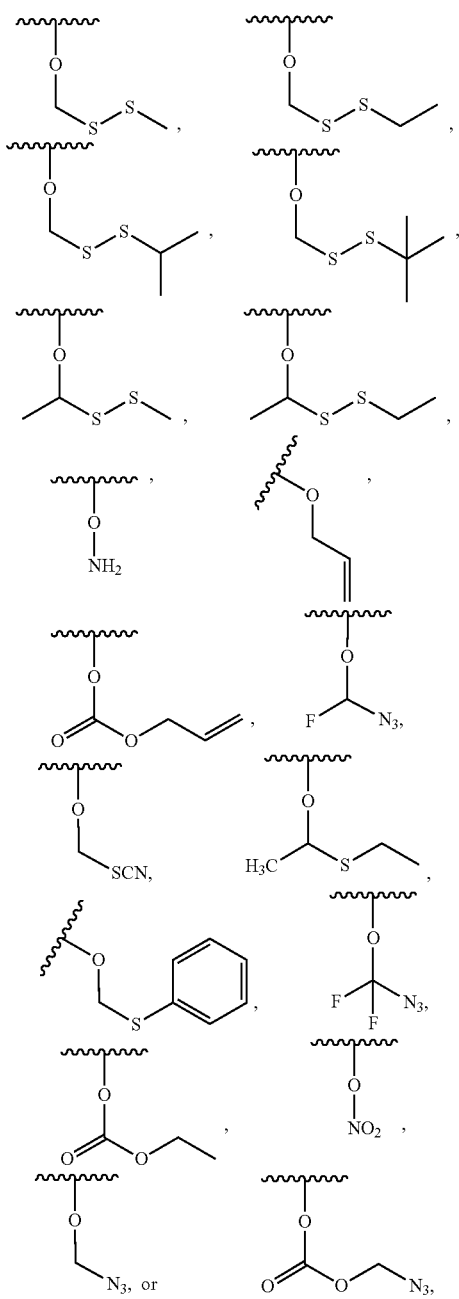

wherein the 3' oxygen of the nucleotide is explicitly shown in the formulae above. A label moiety of a nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both. Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the OH group at the 3'-position of deoxyribose. Nucleotide analogues and DNA polymerase-based DNA sequencing are also described in U.S. Pat. No. 6,664,079, which is incorporated herein by reference in its entirety for all purposes.

The term "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite (Na$_2$S$_2$O$_4$), or hydrazine (N$_2$H$_4$)). A chemically cleavable linker is non-enzymatically cleavable. In embodiments, the cleavable linker is cleaved by contacting the cleavable linker with a cleaving agent. In embodiments, the cleaving agent is a phosphine containing reagent (e.g., TCEP or THPP), sodium dithionite (Na$_2$S$_2$O$_4$), weak acid, hydrazine (N$_2$H$_4$), Pd(0), or light-irradiation (e.g., ultraviolet radiation). In embodiments, cleaving includes removing. A "cleavable site" or "scissile linkage" in the context of a polynucleotide is a site which allows controlled cleavage of the polynucleotide strand (e.g., the linker, the primer, or the polynucleotide) by chemical, enzymatic, or photochemical means known in the art and described herein. A scissile site may refer to the linkage of a nucleotide between two other nucleotides in a nucleotide strand (i.e., an internucleosidic linkage). In embodiments, the scissile linkage can be located at any position within the one or more nucleic acid molecules, including at or near a terminal end (e.g., the 3' end of an oligonucleotide) or in an interior portion of the one or more nucleic acid molecules. In embodiments, conditions suitable for separating a scissile linkage include a modulating the pH and/or the temperature. In embodiments, a scissile site can include at least one acid-labile linkage. For example, an acid-labile linkage may include a phosphoramidate linkage. In embodiments, a phosphoramidate linkage can be hydrolysable under acidic conditions, including mild acidic conditions such as trifluoroacetic acid and a suitable temperature (e.g., 30° C.), or other conditions known in the art, for example Matthias Mag, et al Tetrahedron Letters, Volume 33, Issue 48, 1992, 7319-7322. In embodiments, the scissile site can include at least one photolabile internucleosidic linkage (e.g., o-nitrobenzyl linkages, as described in Walker et al, J. Am. Chem. Soc. 1988, 110, 21, 7170-7177), such as o-nitrobenzyloxymethyl or p-nitrobenzyloxymethyl group(s). In embodiments, the scissile site includes at least one uracil nucleobase. In embodiments, a uracil nucleobase can be cleaved with a uracil DNA glycosylase (UDG) or Formamidopyrimidine DNA Glycosylase Fpg. In embodiments, the scissile linkage site includes a sequence-specific nicking site having a nucleotide sequence that is recognized and nicked by a nicking endonuclease enzyme or a uracil DNA glycosylase.

As used herein, the terms "reversible blocking groups" and "reversible terminators" are used in accordance with their plain and ordinary meanings and refer to a blocking moiety located, for example, at the 3' position of the nucleotide and may be a chemically cleavable moiety such as an allyl group, an azidomethyl group or a methoxymethyl group, or may be an enzymatically cleavable group such as a phosphate ester. Non-limiting examples of nucleotide blocking moieties are described in applications WO 2004/018497, U.S. Pat. Nos. 7,057,026, 7,541,444, WO 96/07669, U.S. Pat. Nos. 5,763,594, 5,808,045, 5,872,244 and 6,232,465 the contents of which are incorporated herein by reference in their entirety. The nucleotides may be labelled or unlabeled. They may be modified with reversible terminators useful in methods provided herein and may be 3'-O-blocked reversible or 3'-unblocked reversible terminators. In nucleotides with 3'-O-blocked reversible terminators, the blocking group —OR [reversible terminating (capping) group] is linked to the oxygen atom of the 3'-OH of the pentose, while the label is linked to the base, which acts as a reporter and can be cleaved. The 3'-O-blocked reversible terminators are known in the art, and may be, for instance, a 3'-ONH$_2$ reversible terminator, a 3'-O-allyl reversible terminator, or a 3'-O-azidomethyl reversible terminator. In embodiments, the reversible terminator moiety is attached to the 3'-oxygen of the nucleotide, having the formula:

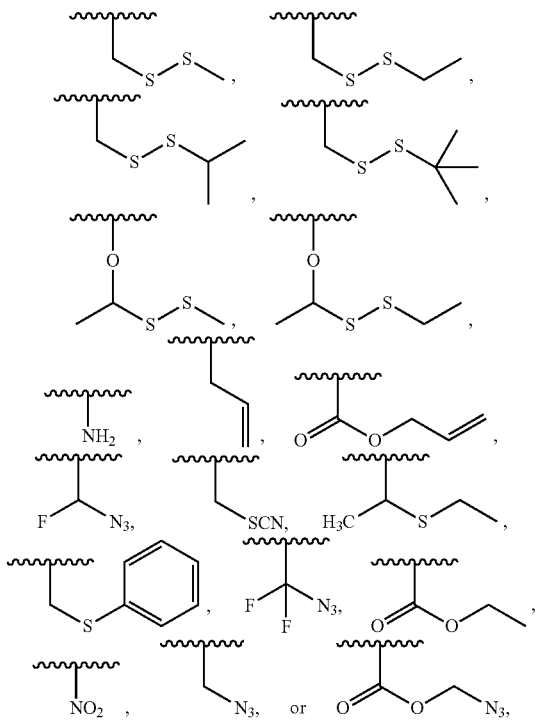

wherein the 3' oxygen of the nucleotide is not shown in the formulae above. The term "allyl" as described herein refers to an unsubstituted methylene attached to a vinyl group (i.e., —CH=CH$_2$). In embodiments, the reversible terminator moiety is

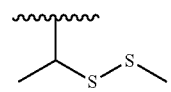 [SMILES: *C(C)SSC]

as described in U.S. Pat. No. 10,738,072, which is incorporated herein by reference for all purposes. For example, a nucleotide including a reversible terminator moiety may be represented by the formula:

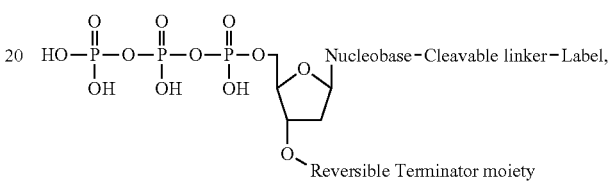

where the nucleobase is adenine or adenine analogue, thymine or thymine analogue, guanine or guanine analogue, or cytosine or cytosine analogue.

A label moiety of a nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both. As used herein, the term "label" or "labels" generally refer to molecules that can directly or indirectly produce or result in a detectable signal either by themselves or upon interaction with another molecule. Non-limiting examples of detectable labels include labels comprising fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the dye is a fluorescent dye. Non-limiting examples of dyes, some of which are commercially available, include CF® dyes (Biotium, Inc.), Alexa Fluor® dyes (Thermo Fisher), DyLight® dyes (Thermo Fisher), Cy® dyes (GE Healthscience), IRDye® dyes (Li-Cor Biosciences, Inc.), and HiLyte™ dyes (Anaspec, Inc.). In embodiments, the label is a fluorophore.

Examples of detectable agents (i.e., labels) include imaging agents, including fluorescent and luminescent substances, molecules, or compositions, including, but not limited to, a variety of organic or inorganic small molecules commonly referred to as "dyes," "labels," or "indicators." Examples include fluorescein, rhodamine, acridine dyes, Alexa Fluor® dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). The term "cyanine" or "cyanine moiety" as described herein refers to a detectable moiety containing two nitrogen groups separated by a polymethine chain. In embodiments, the cyanine moiety has 3 methine structures (i.e. cyanine 3 or Cy3®). In embodiments, the cyanine moiety has 5 methine structures (i.e. cyanine 5 or Cy5®). In embodiments, the cyanine moiety has 7 methine structures (i.e., cyanine 7 or Cy7®).

As used herein, the term "polymer" refers to macromolecules having one or more structurally unique repeating units. The repeating units are referred to as "monomers," which are polymerized for the polymer. Typically, a polymer is formed by monomers linked in a chain-like structure. A polymer formed entirely from a single type of monomer is referred to as a "homopolymer." A polymer formed from two or more unique repeating structural units may be referred to as a "copolymer." A polymer may be linear or branched, and may be random, block, polymer brush, hyperbranched polymer, bottlebrush polymer, dendritic polymer, or polymer micelles. The term "polymer" includes homopolymers, copolymers, tripolymers, tetra polymers and other polymeric molecules made from monomeric subunits. Copolymers include alternating copolymers, periodic copolymers, statistical copolymers, random copolymers, block copolymers, linear copolymers and branched copolymers. The term "polymerizable monomer" is used in accordance with its meaning in the art of polymer chemistry and refers to a compound that may covalently bind chemically to other monomer molecules (such as other polymerizable monomers that are the same or different) to form a polymer. Polymers can be hydrophilic, hydrophobic or amphiphilic, as known in the art. Thus, "hydrophilic polymers" are substantially miscible with water and include, but are not limited to, polyethylene glycol and the like. "Hydrophobic polymers" are substantially immiscible with water and include, but are not limited to, polyethylene, polypropylene, polybutadiene, polystyrene, polymers disclosed herein, and the like. "Amphiphilic polymers" have both hydrophilic and hydrophobic properties and are typically copolymers having hydrophilic segment(s) and hydrophobic segment(s). Polymers include homopolymers, random copolymers, and block copolymers, as known in the art. The term "homopolymer" refers, in the usual and customary sense, to a polymer having a single monomeric unit. The term "copolymer" refers to a polymer derived from two or more monomeric species. The term "random copolymer" refers to a polymer derived from two or more monomeric species with no preferred ordering of the monomeric species. The term "block copolymer" refers to polymers having two or homopolymer subunits linked by covalent bond. Thus, the term "hydrophobic homopolymer" refers to a homopolymer which is hydrophobic. The term "hydrophobic block copolymer" refers to two or more homopolymer subunits linked by covalent bonds and which is hydrophobic.

As used herein, the term "hydrogel" refers to a three-dimensional polymeric structure that is substantially insoluble in water, but which is capable of absorbing and retaining large quantities of water to form a substantially stable, often soft and pliable, structure. In embodiments, water can penetrate in between polymer chains of a polymer network, subsequently causing swelling and the formation of a hydrogel. In embodiments, hydrogels are super-absorbent (e.g., containing more than about 90% water) and can be comprised of natural or synthetic polymers. Hydrogels can contain over 99% water and may comprise natural or synthetic polymers, or a combination thereof. Hydrogels also possess a degree of flexibility very similar to natural tissue, due to their significant water content. A detailed description of suitable hydrogels may be found in published U.S. patent application 20100055733, herein specifically incorporated by reference. By "hydrogel subunits" or "hydrogel precursors" is meant hydrophilic monomers, prepolymers, or polymers that can be crosslinked, or "polymerized", to form a three-dimensional (3D) hydrogel network.

Hydrogels may be prepared by cross-linking hydrophilic biopolymers or synthetic polymers. Thus, in some embodiments, the hydrogel may include a crosslinker. As used herein, the term "crosslinker" refers to a molecule that can form a three-dimensional network when reacted with the appropriate base monomers. Examples of the hydrogel polymers, which may include one or more crosslinkers, include but are not limited to, hyaluronans, chitosans, agar, heparin, sulfate, cellulose, alginates (including alginate sulfate), collagen, dextrans (including dextran sulfate), pectin, carrageenan, polylysine, gelatins (including gelatin type A), agarose, (meth)acrylate-oligolactide-PEO-oligolactide-(meth)acrylate, PEO-PPO-PEO copolymers (Pluronics), poly(phosphazene), poly(methacrylates), poly(N-vinylpyrrolidone), PL(G)A-PEO-PL(G)A copolymers, poly(ethylene imine), polyethylene glycol (PEG)-thiol, PEG-acrylate, acrylamide, N,N'-bis(acryloyl)cystamine, PEG, polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), bisacrylamide, diacrylate, diallylamine, triallylamine, divinyl sulfone, diethyleneglycol diallyl ether, ethyleneglycol diacrylate, polymethyleneglycol diacrylate, polyethyleneglycol diacrylate, trimethylopropoane trimethacrylate, ethoxylated trimethylol triacrylate, or ethoxylated pentaerythritol tetracrylate, or combinations thereof. Thus, for example, a combination may include a polymer and a crosslinker, for example polyethylene glycol (PEG)-thiol/PEG-acrylate, acrylamide/N,N'-bis(acryloyl)cystamine (BACy), or PEG/polypropylene oxide (PPO). In embodiments, the hydrogel includes chemical crosslinks (e.g., intermolecular or intramolecular joining of two or more molecules by a covalent bond) and may be referred to as a chemical hydrogel. In embodiments, the hydrogel includes physical crosslinks (e.g., intermolecular or intramolecular joining of two or more molecules by a non-covalent bond) and may be referred to as a physical hydrogel. In embodiments, the physical hydrogel include one or more crosslinks including hydrogen bonds, hydrophobic interactions, and/or polymer chain entanglements.

The terms "iniferter mediated polymerization" and the like refer, in the usual and customary sense, to polymerization employing an "iniferter" which, as known in the art, is a chemical compound that simultaneously acts as initiator, transfer agent, and terminator in controlled free radical polymerization reactions, e.g., dithiocarbamates. See e.g., Otsu, T., & Yashida, M., *Mackromol. Chem., Rapid Commun.*, 1982, 3:127-132.

The terms "stable free radical mediated polymerization,' "SRFP" and the like refer, in the usual and customary sense, to polymerization reactions wherein the coupling of the stable free radical with the polymeric radical is sufficiently reversible that the termination step is reversible, and the propagating radical concentration can be limited to levels that allow for controlled polymerization. See e.g., Veregin, R. P. N., et al., *Macromolecules* 1993, 26:5316-5320.

The terms "atom transfer radical polymerization," "ATRP" and the like refer, in the usual and customary sense, to methods of polymerization employing a transition metal catalyst, wherein the atom transfer step is the key step in the reaction responsible for uniform polymer chain growth. See e.g., Kato, M., et al., *Macromolecules* 1995, 28:1721-1723; Wang, J. & Matyjaszewski, K., *J. Am. Chem. Soc.* 1995, 117:5614-5615.

The terms "reversible addition fragmentation chain transfer polymerization," "RAFT" and the like refer, in the usual and customary sense, to methods of polymerization which use a chain transfer agent in the form of a thiocarbonylthio compound or the like to afford control over the generated molecular weight and polydispersity during a free-radical polymerization. See e.g., Yeole, N., *Synlett.* 2010(10): 1572-1573; Moad, G., et al., *Aust. J. Chem.,* 2005, 58:379-410.

As used herein, the term "discrete particles" refers to physically distinct particles having discernible boundaries. The term "particle" does not indicate any particular shape. The shapes and sizes of a collection of particles may be different or about the same (e.g., within a desired range of dimensions, or having a desired average or minimum dimension). A particle may be substantially spherical (e.g., microspheres) or have a non-spherical or irregular shape, such as cubic, cuboid, pyramidal, cylindrical, conical, oblong, or disc-shaped, and the like. In embodiments, the particle has the shape of a sphere, cylinder, spherocylinder, or ellipsoid. Discrete particles collected in a container and contacting one another will define a bulk volume containing the particles, and will typically leave some internal fraction of that bulk volume unoccupied by the particles, even when packed closely together. In embodiments, cores and/or core-shell particles are approximately spherical. As used herein the term "spherical" refers to structures which appear substantially or generally of spherical shape to the human eye, and does not require a sphere to a mathematical standard. In other words, "spherical" cores or particles are generally spheroidal in the sense of resembling or approximating to a sphere. In embodiments, the diameter of a spherical core or particle is substantially uniform, e.g., about the same at any point, but may contain imperfections, such as deviations of up to 1, 2, 3, 4, 5 or up to 10%. Because cores or particles may deviate from a perfect sphere, the term "diameter" refers to the longest dimension of a given core or particle. Likewise, polymer shells are not necessarily of perfect uniform thickness all around a given core. Thus, the term "thickness" in relation to a polymer structure (e.g., a shell polymer of a core-shell particle) refers to the average thickness of the polymer layer.

As used herein, the term "channel" refers to a passage in or on a substrate material that directs the flow of a fluid. A channel may run along the surface of a substrate, or may run through the substrate between openings in the substrate. A channel can have a cross section that is partially or fully surrounded by substrate material (e.g., a fluid impermeable substrate material). For example, a partially surrounded cross section can be a groove, trough, furrow or gutter that inhibits lateral flow of a fluid. The transverse cross section of an open channel can be, for example, U-shaped, V-shaped, curved, angular, polygonal, or hyperbolic. A channel can have a fully surrounded cross section such as a tunnel, tube, or pipe. A fully surrounded channel can have a rounded, circular, elliptical, square, rectangular, or polygonal cross section. A microfluidic flow channel is characterized by cross-sectional dimensions less than 1000 microns. Usually at least one, and preferably all, cross-sectional dimensions are greater than 500 microns.

As used herein, the term "substrate" refers to a solid support material. The substrate can be non-porous or porous. The substrate can be rigid or flexible. A nonporous substrate generally provides a seal against bulk flow of liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefin copolymers, polyimides etc.), nylon, ceramics, resins, Zeonor, silica or silica-based materials including silicon and modified silicon, carbon, metals, inorganic glasses, optical fiber bundles, photopatternable dry film resists, UV-cured adhesives and polymers. Particularly useful solid supports for some embodiments have at least one surface located on a microplate. Solid surfaces can also be varied in their shape depending on the application in a method described herein. For example, a solid surface useful herein can be planar, or contain regions which are concave or convex. In embodiments, the geometry of the concave or convex regions (e.g., wells) of the solid surface conform to the size and shape of a substantially circular particle to maximize the contact between the particle. In embodiments, the wells of an array are randomly located such that nearest neighbor wells have random spacing between each other. Alternatively, in embodiments the spacing between the wells can be ordered, for example, forming a regular pattern. The term solid substrate is encompassing of a substrate (e.g., a microplate) having a surface comprising a polymer coating covalently attached thereto.

The term "microplate", as used herein, refers to a substrate comprising a surface, the surface including a plurality of reaction chambers separated from each other by interstitial regions on the surface. In embodiments, the microplate has dimensions as provided and described by American National Standards Institute (ANSI) and Society for Laboratory Automation And Screening (SLAS); for example the tolerances and dimensions set forth in ANSI SLAS 1-2004 (R2012); ANSI SLAS 2-2004 (R2012); ANSI SLAS 3-2004 (R2012); ANSI SLAS 4-2004 (R2012); and ANSI SLAS 6-2012, which are incorporated herein by reference. The dimensions of the microplate as described herein and the arrangement of the reaction chambers may be compatible with an established format for automated laboratory equipment. In embodiments, the device described herein provides methods for high-throughput screening. High-throughput screening (HTS) refers to a process that uses a combination of modern robotics, data processing and control software, liquid handling devices, and/or sensitive detectors, to efficiently process a large amount of (e.g., thousands, hundreds of thousands, or millions) samples in biochemical, genetic, or pharmacological experiments, either in parallel or in sequence, within a reasonably short period of time (e.g., days). Preferably, the process is amenable to automation, such as robotic simultaneous handling of 96 samples, 384 samples, 1536 samples or more. A typical HTS robot tests up to 100,000 to a few hundred thousand compounds per day. The samples are often in small volumes, such as no more than 1 mL, 500 µl, 200 µl, 100 µl, 50 µl or less. Through this process, one can rapidly identify active compounds, small molecules, antibodies, proteins or polynucleotides in a cell.

The reaction chambers may be provided as wells (alternatively referred to as reaction chambers), for example a microplate may contain 2, 4, 6, 12, 24, 48, 96, 384, or 1536 sample wells. In embodiments, the 96 and 384 wells are arranged in a 2:3 rectangular matrix. In embodiments, the 24 wells are arranged in a 3:8 rectangular matrix. In embodiments, the 48 wells are arranged in a 3:4 rectangular matrix. In embodiments, the reaction chamber is a microscope slide (e.g., a glass slide about 75 mm by about 25 mm). In embodiments the slide is a concavity slide (e.g., the slide includes a depression). In embodiments, the slide includes a coating for enhanced cell adhesion (e.g., poly-L-lysine, silanes, carbon nanotubes, polymers, epoxy resins, or gold). In embodiments, the microplate is about 5 inches by about 3.33 inches, and includes a plurality of 5 mm diameter wells. In embodiments, the microplate is about 5 inches by about 3.33 inches, and includes a plurality of 6 mm diameter wells. In embodiments, the microplate is about 5 inches by about 3.33 inches, and includes a plurality of 7 mm diameter wells. In embodiments, the microplate is about 5 inches by about 3.33 inches, and includes a plurality of 7.5 mm diameter wells. In embodiments, the microplate is 5 inches by 3.33 inches, and includes a plurality of 7.5 mm diameter wells. In embodiments, the microplate is about 5 inches by about 3.33 inches, and includes a plurality of 8 mm diameter wells. In embodiments, the microplate is a flat glass or plastic tray in which an array of wells are formed, wherein each well can hold between from a few microliters to hundreds of microliters of fluid reagents and samples. In embodiments, the microplate has a rectangular shape that measures 127.7 mm±0.5 mm in length by 85.4 mm±0.5 mm in width, and includes 6, 12, 24, 48, or 96 wells, wherein each well has an average diameter of about 5-7 mm. In embodiments, the microplate has a rectangular shape that measures 127.7 mm±0.5 mm in length by 85.4 mm±0.5 mm in width, and includes 6, 12, 24, 48, or 96 wells, wherein each well has an average diameter of about 6 mm.

The term "surface" is intended to mean an external part or external layer of a substrate. The surface can be in contact with another material such as a gas, liquid, gel, polymer, organic polymer, second surface of a similar or different material, metal, or coat. The surface, or regions thereof, can be substantially flat. The substrate and/or the surface can have surface features such as wells, pits, channels, ridges, raised regions, pegs, posts or the like.

The term "well" refers to a discrete concave feature in a substrate having a surface opening that is completely surrounded by interstitial region(s) of the surface. Wells can have any of a variety of shapes at their opening in a surface including but not limited to round, elliptical, square, polygonal, or star shaped (i.e., star shaped with any number of vertices). The cross section of a well taken orthogonally with the surface may be curved, square, polygonal, hyperbolic, conical, or angular. The wells of a microplate are available in different shapes, for example F-Bottom: flat bottom; C-Bottom: bottom with minimal rounded edges; V-Bottom: V-shaped bottom; or U-Bottom: U-shaped bottom. In embodiments, the well is substantially square. In embodiments, the well is square. In embodiments, the well is F-bottom. In embodiments, the microplate includes 24 substantially round flat bottom wells. In embodiments, the microplate includes 48 substantially round flat bottom wells. In embodiments, the microplate includes 96 substantially round flat bottom wells. In embodiments, the microplate includes 384 substantially square flat bottom wells.

The discrete regions (i.e., features, wells) of the microplate may have defined locations in a regular array, which may correspond to a rectilinear pattern, circular pattern, hexagonal pattern, or the like. In embodiments, the pattern of wells includes concentric circles of regions, spiral patterns, rectilinear patterns, hexagonal patterns, and the like. In embodiments, the pattern of wells is arranged in a rectilinear or hexagonal pattern A regular array of such regions is advantageous for detection and data analysis of signals collected from the arrays during an analysis. These discrete regions are separated by interstitial regions. As used herein, the term "interstitial region" refers to an area in a substrate or on a surface that separates other areas of the substrate or surface. For example, an interstitial region can separate one concave feature of an array from another concave feature of the array. The two regions that are separated from each other can be discrete, lacking contact with each other. In another example, an interstitial region can separate a first portion of a feature from a second portion of a feature. In embodiments the interstitial region is continuous whereas the features are discrete, for example, as is the case for an array of wells in an otherwise continuous surface. The separation provided by an interstitial region can be partial or full separation. In embodiments, interstitial regions have a surface material that differs from the surface material of the wells (e.g., the interstitial region contains a photoresist and the surface of the well is glass). In embodiments, interstitial regions have a surface material that is the same as the surface material of the wells (e.g., both the surface of the interstitial region and the surface of well contain a polymer or copolymer).

"Contacting" is used in accordance with its plain ordinary meaning and refers to the process of allowing at least two distinct species (e.g., chemical compounds including biomolecules, particles, solid supports, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments contacting includes allowing a sample as described herein to interact with a microplate.

As used herein, the terms "fluidic contact" or "fluidic contacting" or "fluidic communication" refers to at least two spatial regions being connected together such that a liquid or gas may flow between the two spatial regions. In embodiments, two spatially separated species (e.g., chemical compounds, biomolecules, nucleotides, binding reagents, cells, substrates, polymers, polymeric gels, or solid supports) are in fluidic contact when a liquid is capable of contacting each species, optionally simultaneously contacting both species. For example, placing two permeable substrates in fluidic contact may allow diffusion or flowing of a fluid (e.g., one or more liquid reagents) from one substrate to the other substrate. In some embodiments, the first later, the second layer, and the third layer of a multi-layer composition are in fluidic contact, wherein the first layer and the third layer are also in fluidic contact if present in the same fluidic environment. In embodiments, fluidic contact may be achieved using an integrated system of one or more chambers, ports, and/or channels that are interconnected and coupled via one or more connections or tubes.

As used herein the term "determine" can be used to refer to the act of ascertaining, establishing or estimating. A determination can be probabilistic. For example, a determination can have an apparent likelihood of at least 50%, 75%, 90%, 95%, 98%, 99%, 99.9% or higher. In some cases, a determination can have an apparent likelihood of 100%. An exemplary determination is a maximum likelihood analysis or report. As used herein, the term "identify," when used in reference to a thing, can be used to refer to recognition of the thing, distinction of the thing from at least one other thing or categorization of the thing with at least one other thing. The recognition, distinction or categorization can be probabilistic. For example, a thing can be identified with an apparent likelihood of at least 50%, 75%, 90%, 95%, 98%, 99%, 99.9% or higher. A thing can be identified based on a result of a maximum likelihood analysis. In some cases, a thing can be identified with an apparent likelihood of 100%.

As used herein, the terms "sequencing", "sequence determination", and "determining a nucleotide sequence", are used in accordance with their ordinary meaning in the art, and refer to determination of partial as well as full sequence information of the nucleic acid being sequenced, and particular physical processes for generating such sequence information. That is, the term includes sequence comparisons, fingerprinting, and like levels of information about a target nucleic acid, as well as the express identification and ordering of nucleotides in a target nucleic acid. The term also includes the determination of the identification, ordering, and locations of one, two, or three of the four types of nucleotides within a target nucleic acid. Sequencing produces one or more sequencing reads.

As used herein, the term "sequencing cycle" is used in accordance with its plain and ordinary meaning and refers to incorporating one or more nucleotides (e.g., nucleotide analogues) to the 3' end of a polynucleotide with a polymerase, and detecting one or more labels that identify the one or more nucleotides incorporated. The sequencing may be accomplished by, for example, sequencing by synthesis, pyrosequencing, and the like. In embodiments, a sequencing cycle includes extending a complementary polynucleotide by incorporating a first nucleotide using a polymerase, wherein the polynucleotide is hybridized to a template nucleic acid, detecting the first nucleotide, and identifying the first nucleotide. In embodiments, to begin a sequencing cycle, one or more differently labeled nucleotides and a DNA polymerase can be introduced. Following nucleotide addition, signals produced (e.g., via excitation and emission of a detectable label) can be detected to determine the identity of the incorporated nucleotide (based on the labels on the nucleotides). Reagents can then be added to remove the 3' reversible terminator and to remove labels from each incorporated base. Reagents, enzymes and other substances can be removed between steps by washing. Cycles may include repeating these steps, and the sequence of each cluster is read over the multiple repetitions.

As used herein, the term "sequencing read" is used in accordance with its plain and ordinary meaning and refers to an inferred sequence of nucleotide bases (or nucleotide base probabilities) corresponding to all or part of a single polynucleotide fragment. A sequencing read may include 10, 20, 30, 40, 50, 60, 70, 80, 90, 100, 150, 200, 250, or more nucleotide bases. In embodiments, a sequencing read includes reading a barcode and a template nucleotide sequence. In embodiments, a sequencing read includes reading a template nucleotide sequence. In embodiments, a sequencing read includes reading a barcode and not a template nucleotide sequence.

As used herein, the term "sequencing reagent" is used in accordance with its plain and ordinary meaning and refers to an aqueous mixture that contains the reagents necessary to add and/or detect a nucleotide (e.g., s dNTP or dNTP analogue) to a DNA strand by a DNA polymerase. In embodiments, the sequencing reaction mixture includes a buffer. In embodiments, the buffer includes an acetate buffer, 3-(N-morpholino)propanesulfonic acid (MOPS) buffer, N-(2-Acetamido)-2-aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl-1-propanol (AMP) buffer, 4-(Cyclohexylamino)-1-butanesulfonic acid (CABS) buffer, glycine-NaOH buffer, N-Cyclohexyl-2-aminoethanesulfonic acid (CHES) buffer, tris(hydroxymethyl)aminomethane (Tris) buffer, or a N-cyclohexyl-3-aminopropanesulfonic acid (CAPS) buffer. In embodiments, the buffer is a borate buffer. In embodiments, the buffer is a CHES buffer. In embodiments, the sequencing reaction mixture includes nucleotides, wherein the nucleotides include a reversible terminating moiety and a label covalently linked to the nucleotide via a cleavable linker. In embodiments, the sequencing reaction mixture includes a buffer, DNA polymerase, detergent (e.g., Triton® X), a chelator (e.g., EDTA), and/or salts (e.g., ammonium sulfate, magnesium chloride, sodium chloride, or potassium chloride). Triton is a registered trademark of Dow Chemical.

As used herein, the term "extension" or "elongation" is used in accordance with its plain and ordinary meanings and refer to synthesis by a polymerase of a new polynucleotide strand complementary to a template strand by adding free nucleotides (e.g., dNTPs) from a reaction mixture that are complementary to the template in the 5'- to-3' direction. Extension includes condensing the 5'-phosphate group of the dNTPs with the 3'-hydroxy group at the end of the nascent (elongating) polynucleotide strand.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the invention. The upper and lower limits of any such smaller range (within a more broadly recited range) may independently be included in the smaller ranges, or as particular values themselves, and are also encompassed within the invention, subject to any specifically excluded limit in the stated range. Where the stated range includes one or both of the limits, ranges excluding either or both of those included limits are also included in the invention.

As used herein, the terms "incubate," and "incubation" refer collectively to altering the temperature of an object in a controlled manner such that conditions are sufficient for conducting the desired reaction. Thus, it is envisioned that the terms encompass heating a receptacle (e.g., a microplate) to a desired temperature and maintaining such temperature for a fixed time interval. Also included in the terms is the act of subjecting a receptacle to one or more heating and cooling cycles (i.e., "temperature cycling" or "thermal cycling"). While temperature cycling typically occurs at relatively high rates of change in temperature, the term is not limited thereto, and may encompass any rate of change in temperature.

As used herein, "biological activity" may include the in vivo activities of a compound or physiological responses that result upon in vivo administration of a compound, composition or other mixture. Biological activity, thus, may encompass therapeutic effects and pharmaceutical activity of such compounds, compositions and mixtures. Biological activities may be observed in vitro systems designed to test or use such activities.

The term "isolated" means altered or removed from the natural state. For example, a nucleic acid or a polypeptide naturally present in a living animal is not isolated, but the same nucleic acid or polypeptide partially or completely separated from the coexisting materials of its natural state is isolated. An isolated nucleic acid or protein can exist in substantially purified form, or can exist in a non-native environment such as, for example, a host cell.

As used herein, a "plurality" refers to two or more.

The term "transcriptome," as used herein, generally refers to sequencing many (e.g., 1-50 million) RNA or cDNA molecules, to determine gene expression, detect gene fusion, and alternative splicing events, and detect genetic variants expressed in the RNA.

The terms "particle" and "bead" are used interchangeably and mean a small body made of a rigid or semi-rigid material. The body can have a shape characterized, for example, as a sphere, oval, microsphere, or other recognized particle shape whether having regular or irregular dimensions. A "nanoparticle," as used herein, is a particle wherein the longest diameter is less than or equal to 1000 nanometers. Nanoparticles may be composed of any appropriate material. For example, nanoparticle cores may include appropriate metals and metal oxides thereof (e.g., a metal nanoparticle core), carbon (e.g., an organic nanoparticle core) silicon and oxides thereof (e.g., a silicon nanoparticle core) or boron and oxides thereof (e.g., a boron nanoparticle core), or mixtures thereof. Nanoparticles may be composed of at least two distinct materials, one material (e.g., silica) forms the core and the other material forms the shell (e.g., copolymer) surrounding the core.

Lengths and sizes of particles and functionalized particles as described herein may be measured using Transmission Electron Microscopy. For example, transmission electron microscopy measurements of the various particle samples may be drop coated (5 L) onto 200 mesh copper EM grids, air-dried and imaged using a FEI Tecnai 12 TEM equipped with a Gatan Ultrascan 2K CCD camera at an accelerating voltage of 120 kV. The average size distributions of the particles may then be obtained from the TEM images to obtain the histogram size distributions of the particles. In embodiment, the length of a nanoparticle refers to the longest dimension of the particle.

The terms "bioconjugate group," "bioconjugate reactive moiety," and "bioconjugate reactive group" refer to a chemical moiety which participates in a reaction to form a bioconjugate linker (e.g., covalent linker).

As used herein, the term "bioconjugate reactive moiety" and "bioconjugate reactive group" refers to a moiety or group capable of forming a bioconjugate (e.g., covalent linker) as a result of the association between atoms or molecules of bioconjugate reactive groups. The association can be direct or indirect. For example, a conjugate between a first bioconjugate reactive group (e.g., $-NH_2$, $-COOH$, $-N$-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine).

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds; (n) azides coupled to alkynes using copper catalyzed cycloaddition click chemistry; (o) biotin conjugate can react with avidin or strepavidin to form a avidin-biotin complex or streptavidin-biotin complex.

The term "covalent linker" is used in accordance with its ordinary meaning and refers to a divalent moiety which connects at least two moieties to form a molecule.

As used herein, the terms "thermoelectric Peltier device" and "Peltier device" are used in accordance with their plain ordinary meaning and refers to an alternating p and n-type semiconductor solid state heat pump capable of transferring heat from one side of the device to the other with consumption of electrical energy. Depending on the direction of current, it can be used to heat or cool a surface.

The terms "fluid communication" or "fluidically coupled" refers to two spatial regions being connected together such that a liquid or gas may flow between the two spatial regions. As used herein, the terms "fluid" or "solution" or "reagent" may be used interchangeably and includes any liquid or gas. A fluid can include, for example, a sequencing reaction solution (such as aqueous buffer containing enzymes, salts, and nucleotides); a wash solution (an aqueous buffer); a cleave solution (an aqueous buffer containing a cleaving agent, such as a reducing agent); or a cleaning solution (a dilute bleach solution, dilute NaOH solution, dilute HCl solution, a dilute antibacterial solution).

As used herein the terms "automated" and "semi-automated" mean that the operations are performed by system programming or configuration with little or no human interaction once the operations are initiated, or once processes including the operations are initiated.

Provided herein are methods, systems, devices, and compositions for analyzing a sample in situ. The term "in situ" is used in accordance with its ordinary meaning in the art and refers to a sample surrounded by at least a portion of its native environment, such as may preserve the relative position of two or more elements. For example, an extracted human cell obtained is considered in situ when the cell is retained in its local microenvironment so as to avoid extracting the target (e.g., nucleic acid molecules or proteins) away from their native environment. An in situ sample (e.g., a cell) can be obtained from a suitable subject. An in situ cell sample may refer to a cell and its surrounding milieu, or a tissue. A sample can be isolated or obtained directly from a subject or part thereof. In embodiments, the methods described herein (e.g., sequencing a plurality of target nucleic acids of a cell in situ) are applied to an isolated cell (i.e., a cell not surrounded by least a portion of its native environment). For the avoidance of any doubt, when the method is performed within a cell (e.g., an isolated cell) the method may be considered in situ. In some embodiments, a sample is obtained indirectly from an individual or medical professional. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may include cells or tissues that are normal, healthy, diseased (e.g., infected), and/or cancerous (e.g., cancer cells). A sample obtained from a subject may include cells or cellular material (e.g., nucleic acids) of multiple organisms (e.g., virus nucleic acid, fetal nucleic acid, bacterial nucleic acid, parasite nucleic acid). A sample may include a cell and RNA transcripts. A sample can include nucleic acids obtained from one or more subjects. In some embodiments a sample includes nucleic acid obtained from a single subject. A subject can be any living or non-living organism, including but not limited to a human, non-human animal, plant, bacterium, fungus, virus, or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a plant. In some embodiments, a subject is a human subject. A subject can be a patient (e.g., a human patient). In some embodiments a subject is suspected of having a genetic variation or a disease or condition associated with a genetic variation.

As used herein, the term "disease state" is used in accordance with its plain and ordinary meaning and refers to any abnormal biological state or aberration of a cell. The presence of a disease state may be identified by the same collection of biological constituents used to determine the cell's biological state. In general, a disease state will be detrimental to a biological system. A disease state may be a consequence of, inter alia, an environmental pathogen, for example a viral infection (e.g., HIV/AIDS, hepatitis B, hepatitis C, influenza, measles, etc.), a bacterial infection, a parasitic infection, a fungal infection, or infection by some other organism. A disease state may also be the consequence of some other environmental agent, such as a chemical toxin or a chemical carcinogen. As used herein, a disease state further includes genetic disorders wherein one or more copies of a gene is altered or disrupted, thereby affecting its biological function. Exemplary genetic diseases include, but are not limited to polycystic kidney disease, familial multiple endocrine neoplasia type I, neurofibromatoses, Tay-Sachs disease, Huntington's disease, sickle cell anemia, thalassemia, and Down's syndrome, as well as others (see, e.g., The Metabolic and Molecular Bases of Inherited Diseases, 7th ed., McGraw-Hill Inc., New York). Other exemplary diseases include, but are not limited to, cancer, hypertension, Alzheimer's disease, neurodegenerative diseases, and neuropsychiatric disorders such as bipolar affective disorders or paranoid schizophrenic disorders. Disease states are monitored to determine the level (e.g., the stage or progression) of one or more disease states of a subject and, more specifically, detect changes in the biological state of a subject which are correlated to one or more disease states (see, e.g., U.S. Pat. No. 6,218,122, which is incorporated by reference herein in its entirety). The methods of the present invention are also applicable to monitoring the disease state or states of a subject undergoing one or more therapies. Thus, the present invention also provides methods for determining or monitoring efficacy of a therapy or therapies (i.e., determining a level of therapeutic effect) upon a subject. In embodiment, the methods of the invention can be used to assess therapeutic efficacy in a clinical trial, e.g., as an early surrogate marker for success or failure in such a clinical trial. Within eukaryotic cells, there are hundreds to thousands of signaling pathways that are interconnected. For this reason, perturbations in the function of proteins within a cell have numerous effects on other proteins and the transcription of other genes that are connected by primary, secondary, and sometimes tertiary pathways. This extensive interconnection between the function of various proteins means that the alteration of any one protein is likely to result in compensatory changes in a wide number of other proteins. In particular, the partial disruption of even a single protein within a cell, such as by exposure to a drug or by a disease state which modulates the gene copy number (e.g., a genetic mutation), results in characteristic compensatory changes in the transcription of enough other genes that these changes in transcripts can be used to define a "signature" of particular transcript alterations which are related to the disruption of function, i.e., a particular disease state or therapy, even at a stage where changes in protein activity are undetectable.

As used herein, a "single cell" refers to one cell. Single cells useful in the methods described herein can be obtained from a tissue of interest, or from a biopsy, blood sample, or cell culture. Additionally, cells from specific organs, tissues, tumors, neoplasms, or the like can be obtained and used in the methods described herein. In general, cells from any population can be used in the methods, such as a population of prokaryotic or eukaryotic organisms, including bacteria or yeast.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer. A protein may refer to a protein expressed in a cell. A polypeptide, or a cell is "recombinant" when it is artificial or engineered, or derived from or contains an artificial or engineered protein or nucleic acid (e.g., non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

An "antibody" (Ab) is a protein that binds specifically to a particular substance, known as an "antigen" (Ag). An "antibody" or "antigen-binding fragment" is an immunoglobulin that binds a specific "epitope." The term encompasses polyclonal, monoclonal, and chimeric antibodies. In nature, antibodies are generally produced by lymphocytes in response to immune challenge, such as by infection or immunization. An "antigen" (Ag) is any substance that reacts specifically with antibodies or T lymphocytes (T cells). An antibody may include the entire antibody as well as any antibody fragments capable of binding the antigen or antigenic fragment of interest. Examples include complete antibody molecules, antibody fragments, such as Fab, F(ab') 2, CDRs, VL, VH, and any other portion of an antibody which is capable of specifically binding to an antigen. Antibodies used herein are immunospecific for, and therefore specifically and selectively bind to, for example, proteins either detected (i.e., biological targets of interest) or used for detection (i.e., probes containing oligonucleotide barcodes) in the methods and devices as described herein.

The terms "cellular component" is used in accordance with its ordinary meaning in the art and refers to any organelle, nucleic acid, protein, or analyte that is found in a prokaryotic, eukaryotic, archaeal, or other organismic cell type. Examples of cellular components (e.g., a component of a cell) include RNA transcripts, proteins, membranes, lipids, and other analytes.

A "gene" refers to a polynucleotide that is capable of conferring biological function after being transcribed and/or translated.

The term "multiplexing" as used herein refers to an analytical method in which the presence and/or amount of multiple targets, e.g., multiple nucleic acid target sequences, can be assayed simultaneously by using the methods and devices as described herein, each of which has at least one different detection characteristic, e.g., fluorescence characteristic (for example excitation wavelength, emission wavelength, emission intensity, FWHM (full width at half maximum peak height), or fluorescence lifetime) or a unique nucleic acid or protein sequence characteristic.

As used herein a "genetically modifying agent" is a substance that alters the genetic sequence of a cell following exposure to the cell, resulting in an agent-mediated nucleic acid sequence. In embodiments, the genetically modifying agent is a small molecule, protein, pathogen (e.g., virus or bacterium), toxin, oligonucleotide, or antigen. In embodiments, the genetically modifying agent is a virus (e.g., influenza) and the agent-mediated nucleic acid sequence is the nucleic acid sequence that develops within a T-cell upon cellular exposure and contact with the virus. In embodiments, the genetically modifying agent modulates the expression of a nucleic acid sequence in a cell relative to a control (e.g., the absence of the genetically modifying agent).

The term "synthetic target" as used herein refers to a modified protein or nucleic acid such as those constructed by synthetic methods. In embodiments, a synthetic target is artificial or engineered, or derived from or contains an artificial or engineered protein or nucleic acid (e.g., non-natural or not wild type). For example, a polynucleotide that is inserted or removed such that it is not associated with nucleotide sequences that normally flank the polynucleotide as it is found in nature is a synthetic target polynucleotide.

As used herein, the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association. In some instances two or more associated species are "tethered", "coated", "attached", or "immobilized" to one another or to a common solid or semisolid support (e.g., the well of a microplate). An association may refer to a relationship, or connection, between two entities. Associated may refer to the relationship between a sample and the DNA molecules, RNA molecules, or polynucleotides originating from or derived from that sample. These relationships may be encoded in oligonucleotide barcodes, as described herein. A polynucleotide is associated with a sample if it is an endogenous polynucleotide, i.e., it occurs in the sample at the time the sample is obtained, or is derived from an endogenous polynucleotide. For example, the RNAs endogenous to a cell are associated with that cell. cDNAs resulting from reverse transcription of these RNAs, and DNA amplicons resulting from PCR amplification of the cDNAs, contain the sequences of the RNAs and are also associated with the cell. The polynucleotides associated with a sample need not be located or synthesized in the sample, and are considered associated with the sample even after the sample has been destroyed (for example, after a cell has been lysed). Barcoding can be used to determine which polynucleotides in a mixture are associated with a particular sample.

The term "image" is used according to its ordinary meaning and refers to a representation of all or part of an object. The representation may be an optically detected reproduction. For example, an image can be obtained from fluorescent, luminescent, scatter, or absorption signals. The part of the object that is present in an image can be the surface or other xy plane of the object. Typically, an image is a 2 dimensional representation of a 3 dimensional object. An image may include signals at differing intensities (i.e., signal levels). An image can be provided in a computer readable format or medium. An image is derived from the collection of focus points of light rays coming from an object (e.g., the sample), which may be detected by any image sensor.

As used herein, the term "signal" is intended to include, for example, fluorescent, luminescent, scatter, or absorption impulse or electromagnetic wave transmitted or received. Signals can be detected in the ultraviolet (UV) range (about 200 to 390 nm), visible (VIS) range (about 391 to 770 nm), infrared (IR) range (about 0.771 to 25 microns), or other range of the electromagnetic spectrum. The term "signal level" refers to an amount or quantity of detected energy or coded information. For example, a signal may be quantified by its intensity, wavelength, energy, frequency, power, luminance, or a combination thereof. Other signals can be quantified according to characteristics such as voltage, current, electric field strength, magnetic field strength, frequency, power, temperature, etc. Absence of signal is understood to be a signal level of zero or a signal level that is not meaningfully distinguished from noise.

The term "xy coordinates" refers to information that specifies location, size, shape, and/or orientation in an xy plane. The information can be, for example, numerical coordinates in a Cartesian system. The coordinates can be provided relative to one or both of the x and y axes or can be provided relative to another location in the xy plane (e.g., a fiducial). The term "xy plane" refers to a 2 dimensional area defined by straight line axes x and y. When used in reference to a detecting apparatus and an object observed by the detector, the xy plane may be specified as being orthogonal to the direction of observation between the detector and object being detected.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

As used herein, the term "tissue section" refers to a piece of tissue that has been obtained from a subject, optionally fixed and attached to a surface, e.g., a microscope slide.

It will be apparent to one skilled in the art upon reading the present disclosure that there are numerous important areas of biological research, diagnostics, and drug development that will benefit from a high throughput multiplexed assay system that can measure simultaneously the amount and spatial location of a biological target in a biological sample. For example, combining the ability to estimate the relative abundance of different RNA transcripts with the ability to reconstruct an image of spatial patterns of abundance across many locations, which may be as small as or even smaller than individual cells, in a tissue enables many different areas of basic research.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

II. Systems and Devices

In an aspect, provided herein are systems and devices that can detect the quantity of a biological target, detect biological activity indicative of a biological target, and perform nucleic acid sequencing. In an aspect is provided a device. In embodiments, the device is an integrated system of one or more chambers, ports, and channels that are directly or indirectly interconnected and in fluid communication and configured for carrying out an analytical reaction or process, either alone or in cooperation with an appliance or instrument that provides support functions, such as sample introduction, fluid and/or reagent driving means, temperature control, detection systems, data collection and/or integration systems, at least for the purpose of profiling a cell and/or determining the nucleic acid sequence of a template polynucleotide. In embodiments, the device as described herein is capable of multiplex analysis of a sample.

Figure 3:
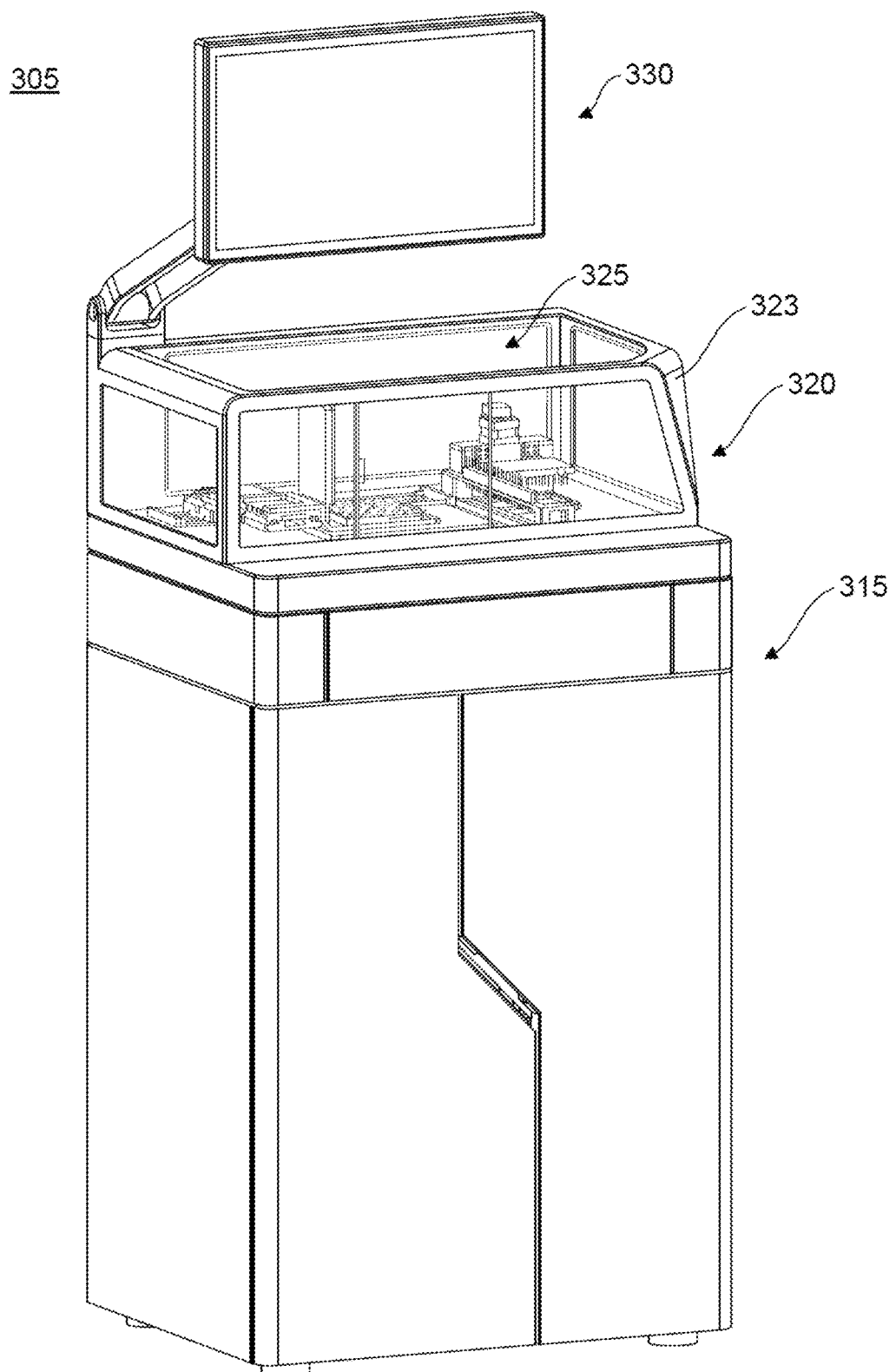
FIG. 3 shows an illustration of an example embodiment of a device as described herein.

FIG. 3 shows a perspective view of an example device and system 305 configured to detect the quantity of a biological target, detect biological activity indicative of a biological target, and perform nucleic acid sequencing. The system 305 includes a support structure or base structure 315 that supports a containment structure forming an enclosed chamber 320 that contains a sample stage assembly 325, as described further below. The base structure 315 can be any support structure such as a table. The base structure 315 can have a size that supports the sample stage assembly 325 at a desired height for access by a user. The enclosed chamber 320 is enclosed by a cover 323 that may be opened to access the sample stage assembly 325. The cover 323 can include at least one transparent window. In embodiments, the window can be transparent to radiation in a particular spectral range including, but not limited to, x-ray, ultraviolet (UV), visible (VIS), infrared (IR), microwave and/or radio wave radiation. In embodiments, one or more windows can provide a view to a microplate contained within the enclosed chamber.

A display 330 is attached or otherwise coupled to the base structure 315. The display 330 is configured to display a user interface that a user can use to interact with the system 305, alternatively referred to herein as a graphical user interface (GUI). For example, the user interface may include a display 330 to display or request information from a user and a user input device to receive user inputs. In embodiments, the display 330 and the user input device are the same device. For example, the user interface may include a touch-sensitive display configured to detect the presence of an individual's touch and also identify a location of the touch on the display. However, other user input devices may be used, such as a mouse, touchpad, keyboard, keypad, handheld scanner, voice-recognition system, motion-recognition system, and the like. Suitable displays include liquid crystal displays (LCD), thin film transistor liquid crystal displays (TFT-LCD), organic light emitting diode (OLED) displays (including passive-matrix OLED (PMOLED) and active-matrix OLED (AMOLED) displays), plasma displays, video projectors, and head-mounted displays (such as a VR headset) in communication with the device. Suitable VR headsets include, by way of non-limiting examples, HTC Vive, Oculus Rift, Oculus Quest, Samsung Gear VR, Microsoft HoloLens, Razer OSVR, FOVE VR, Zeiss VR One, Avegant Glyph, Freefly VR headset, and the like. The graphical display 330 may include a screen including selectable menu options or visual tools, such as drop-down boxes, radio buttons, prompts for numerical values and/or ranges, available for a user to select. In embodiments, the GUI can enable the user to formulate or select an experiment parameter (e.g., experiment type, duration, and/or conditions). The GUI can further display alerts and/or data associated with alerts, including diagnostic information. In embodiments, a user can view and edit workflows with a graphical user interface.

Figure 4A:
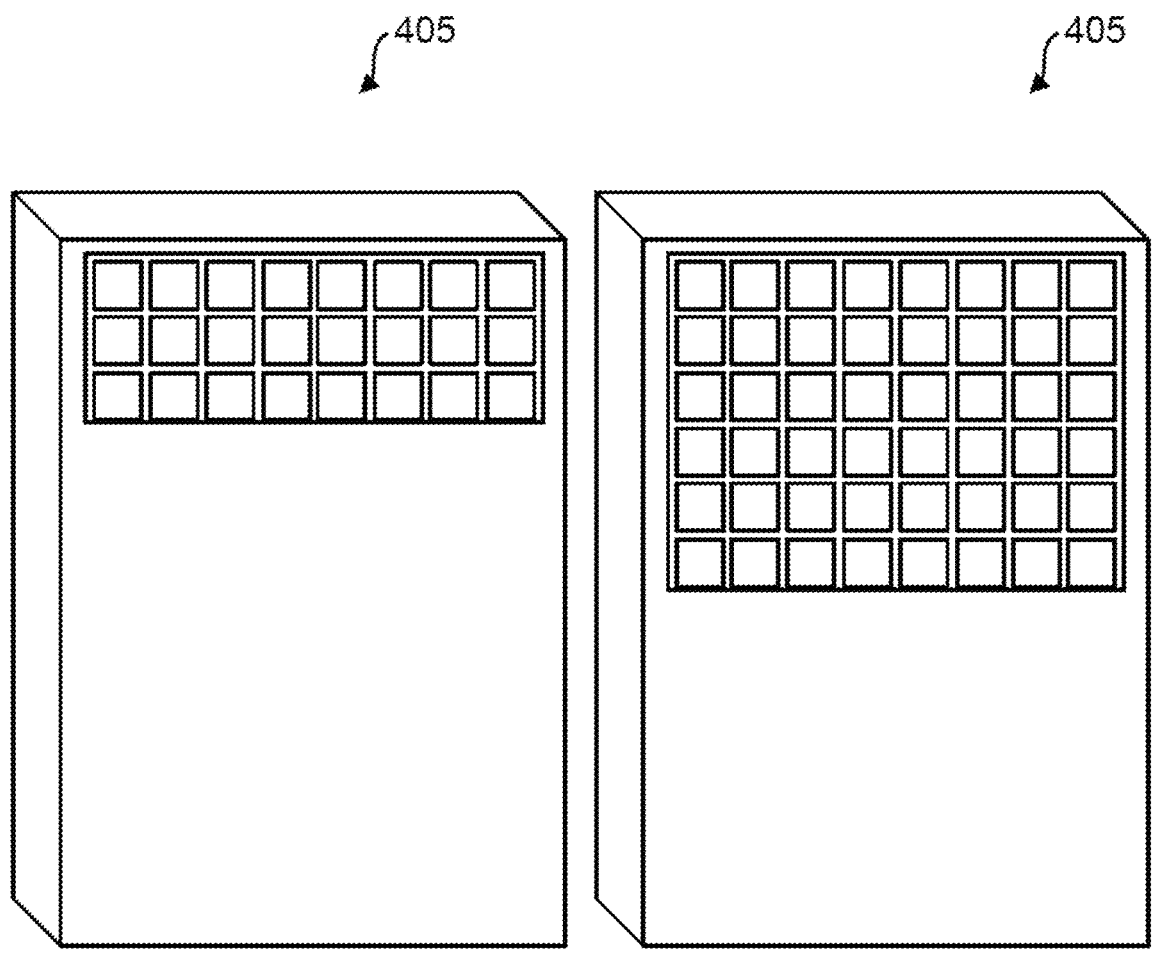
FIGS. 4A-4B show top-down views of example microplates 405 for use in the device described herein. In embodiments, the microplate 405 includes 24 reaction wells (FIG. 4A, left), 48 reaction wells (FIG. 4A, right), 96 reaction wells (FIG. 4B, left), or is configured to retain microscope slides (FIG. 4B, right). In embodiments, the microplate has a rectangular shape that measures 127.7 mm±0.5 mm in length by 85.4 mm±0.5 mm in width. In embodiments, the at least one of the four corners of the microplate are rounded with a corner radius to the outside of 3.1±1.6 mm. In embodiments, one or more corners may be chamfered to assist in aligning the microplate to the receiver.
Figure 4B:
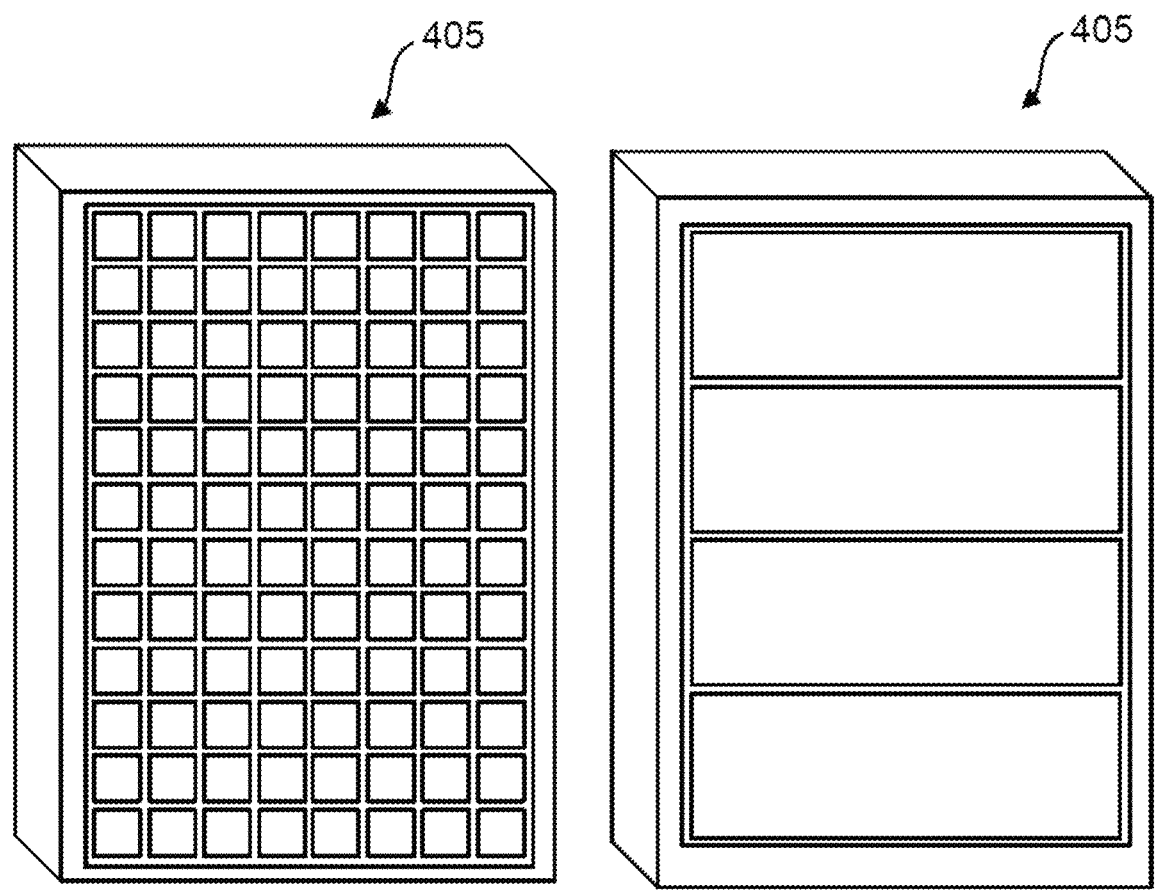

The sample stage assembly 325 is configured to receive or support a microplate. FIGS. 4A-4B show top-down views of example microplates 405 for use in the system 305. In a non-limiting example embodiment shown in FIG. 4A, the microplate 405 includes 24 reaction wells (to the left in FIG. 4A or microplate 405 includes 48 reaction wells (to the right in FIG. 4A. In a non-limiting example embodiment shown in FIG. 4B, the microplate 405 includes 96 reaction wells (FIG. 4B, to the left). The microplate 405 can also be configured to retain microscope slides, as shown in FIG. 4B to the right). In embodiments, the microplate has a rectangular shape with a dimension that can vary. For example, the microplate can measure 127.7 mm±0.5 mm in length by 85.4 mm±0.5 mm in width. In embodiments, the at least one of the four corners of the microplate are rounded with a corner radius to the outside of 3.1±1.6 mm. In embodiments, one or more corners may be chamfered to assist in aligning the microplate to the receiver. In embodiments, the microplate frame includes one or more microplate inserts.

Figure 5:
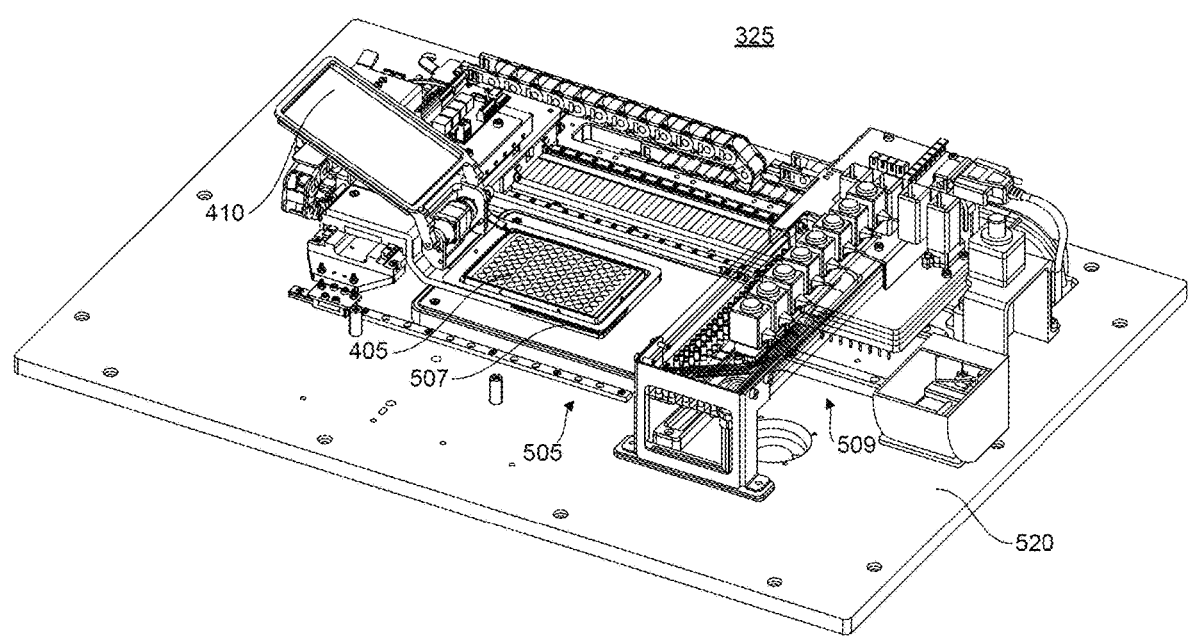
FIG. 5 shows a perspective view of an example embodiment of the sample stage assembly 325 contained within the chamber 320 (as illustrated in FIG. 3.) The sample stage assembly 325 includes a microplate receiver 505 positioned atop a support structure 520. The microplate receiver 505 is at least partially formed of a stage or platform 507 that is configured to support or otherwise be coupled to a microplate 405.

FIG. 5 shows a perspective view of an example embodiment of the sample stage assembly 325 contained within the chamber 320 (FIG. 3.) The sample stage assembly 325 includes a microplate receiver 505 positioned atop a support structure 520. The microplate receiver 505 is at least partially formed of a stage or platform 507 that is configured to support or otherwise be coupled to a microplate 405. In this regard, the platform 507 provides a surface or seat sized and shaped to receive the microplate 405. The platform 507 can form a flat or a contoured surface. The system 305 can include one or more mechanisms configured to enable movement, such as translation, of the microplate 405 when the microplate is seated on the platform 507. Such movement may be along a plane that is parallel to the platform 507 (e.g., along an xy plane).

At least one heating element is thermally coupled to the microplate receiver 505. The heating element is configured to provide heat to a microplate coupled to the microplate receiver 505. In embodiments, the lid 410 is configured to provide heat. In embodiments, the platform 507 is configured to provide heat. The sample stage assembly 325 or any other portion of the system 305 includes a fluidics dispenser configured to dispense one or more reagents into the microplate 405. The fluidics dispenser may include one or more fluidic manifolds 509 configured to direct fluid flow in a predetermined manner. In embodiments, the fluidics dispenser is configured to dispense one or more reagents into only a fraction of the entire microplate 405 (e.g., 12 of the total available wells of the microplate, or into the total number of wells in the microplates as illustrated in FIGS. 4A-4B) at a given time. For example, the device is configured to dispense one or more reagents into only 25% of the entire microplate. In embodiments, the device is configured to dispense one or more reagents into only 50% of the entire microplate 405. In embodiments, the device is configured to dispense one or more reagents into only 75% of the entire microplate 405. The percentages of the microplate recited above may be considered upper limits such that the device is configured to dispense reagents into no more of the microplate than the recited percentage. The one or more fluidics manifolds can be individually controllable and coupled to the microplate 405 in a manner that permits a user to control the percentage of the microplate that is filled. In embodiments, the fluidics dispenser is capable of removing one or more reagents from the microplate (e.g., removing the reagent(s) from the microplate wells).

In embodiments, the device is configured to dispense one or more wash reagents into only a fraction of the entire microplate at a given time. In embodiments, the device is configured to dispense one or more wash reagents into 2-24 wells of a 96 well microplate a given time. In embodiments, the device is configured to dispense one or more wash reagents into 2-12 wells of a 48 well microplate a given time. In embodiments, the device is configured to dispense one or more wash reagents into only 25% of the entire microplate. In embodiments, the device is configured to dispense one or more wash reagents into only 50% of the entire microplate. In embodiments, the device is configured to dispense one or more wash reagents into only 75% of the entire microplate. In embodiments, the device is configured to dispense wash reagents in parallel to all or a fraction of the reaction chambers of the microplate.

In embodiments, the device is configured to sequentially dispense and/or aspirate reagents into 25% of the entire plate (e.g., 24 wells of a 96 well microplate), followed by dispensing and/or aspirating reagents into another 25% of the entire plate (e.g., a different set of 24 wells of a 96 well microplate). In embodiments, the device is configured to sequentially dispense and/or aspirate reagents into another 25% of the entire plate (e.g., a different set from the first set of 24 wells and the second set of 24 wells of a 96 well microplate), followed by dispensing and/or aspirating reagents into a different 25% of the entire plate (e.g., a different set of 24 wells of a 96 well microplate).

Commercial microplates are typically made from plastic polymers (e.g., polypropylene). However, common plastic polymers, such as polypropylene and polyethylene, are susceptible to degradations issues. Thermal degradation, photodegradation, oxidative degradation, and UV degradation can occur, limiting the service life of a plastic microplate. Moreover, solvent compatibility with a range of solvents is required for certain types of analyses. Degradation generally involves changes to the molecular weight and/or structure of the plastic. Other property changes include a reduction in ductility and embrittlement, chalking, color changes, cracking, and a general reduction in desirable physical properties. Biological analyses often require incubation with abrasive chemicals and/or significant thermal shifts (e.g., about 20° C. to about 100° C.). The systems and devices used herein utilize microplates that are stable to temperature shifts and/or chemicals. Biological analyses often require subjecting the sample to significant thermal changes. For example, nucleic acid amplification and/or epitope expression may require cycling between room temperatures (e.g., 20° C. to 25° C.) to an elevated temperature (e.g., 90° C. to 120° C.). Plastic microplates (e.g., polystyrene, polypropylene, cyclic olefin copolymer, or cyclic olefin plastic microplates) are susceptible to warping and thermal degradation. Experiments with plastic microplates fused to an optically clear (COC/COP, glass, or quartz) bottom supports over these temperature ranges resulted in significant sample contamination. Without wishing to be bound by any theory, the different thermal expansion between the planar support (i.e., the glass bottom) and the fused well frame resulted in shearing, separating the well frame from the planar support, resulting in well-to-well leakage. In embodiments, the microwell insert is resistant to chemical degradation. Chemical durability is measured according to known methods in the art, for example via measuring weight loss per surface area following contact with a chemical (e.g., HCl). In embodiments, the microwell insert is capable of contacting xylene without significant degradation (e.g., without significant weight loss). In embodiments, the microwell insert is capable of contacting HCl, $HNO_3$, HF, and/or NaOH, without significant degradation (e.g., without significant weight loss). In embodiments, the microwell insert is capable of contacting organic solvents, such as hexanes or xylenes. Such chemicals can react with the microplate polymers (i.e., oxidization, reaction with functional groups, catalyze de-polymerization), or be absorbed into the bulk microplate material and soften/swell the microplate.

Microplates with clear-bottom wells facilitate optical measurements from the bottom, e.g., inverted high-resolution microscopy and imaging. For optical detection modalities, an optically transparent planar support is useful. Microplate color may be tuned to maximize the signal-to-background ratio. Black microplates are well-suited for fluorescence-based readouts; the black color can reduce well-to-well crosstalk, while also reducing background autofluorescence. In embodiments, the microplate includes a thermoplastic. In embodiments, the microplate includes a thermoplastic polyetherimide (PEI), for example ULTEM™ PEI PolyEtherImide (PEI). In embodiments, the microplate is glass. In embodiments, the microplate is ceramic. In embodiments, the microplate includes steel attached to a glass bottom. In embodiments, the microplate is glass, wherein a plurality of wells are bored directly into the glass. In embodiments, the microplate does not degrade at temperatures greater than 50° C., 60° C., 70° C., 80° C., 90° C., 100° C., 110° C., or 120° C. In embodiments, the microplate does not degrade at temperatures greater than 50° C., 60° C., 70° C., 80° C., 90° C., or 100° C. In embodiments, the microplate does not degrade at 100° C. In embodiments, the microplate bonded to the planar support does not degrade or result in sample contamination at elevated temperatures (e.g., 80° C.-120° C.). The microplate may be used to detect biomolecules (e.g., nucleic acids). Typically, the nucleic acids need to be amplified. In embodiments the term "amplified" refers to a method that comprises a polymerase chain reaction (PCR). Conditions conducive to amplification (i.e., amplification conditions) are well known and often comprise at least a suitable polymerase, a suitable template, a suitable primer or set of primers, suitable nucleotides (e.g., dNTPs), a suitable buffer, and application of suitable annealing, hybridization and/or extension times and temperatures. Amplification conditions may cycle between different temperatures, often involving a large temperature gradient (e.g., 20° C.-40° C.). Additionally, samples embedded in formalin may require additional protocols to render biomolecules available. Heat induced epitope retrieval (HIER) uses heat coupled with buffered solutions to recover antigen reactivity in formalin fixed paraffin embedded tissue samples. Typical HIER methods include increasing the temperature from 25° C. to 95° C.-120° C., if utilizing a water bath or pressure enhanced temperature device (e.g., a pressure cooker). In embodiments, the microplate includes a microplate insert and a planar support attached to the microplate insert. In embodiments, a the planar support can include glass (e.g., a glass slide) that has been coated with a substance or otherwise modified to confer conductive properties to the glass. In some embodiments, a glass slide can be coated with a conductive coating. In some embodiments, a conductive coating includes tin oxide (TO) or indium tin oxide (ITO). In some embodiments, a conductive coating includes a transparent conductive oxide (TCO). In some embodiments, a conductive coating includes aluminum doped zinc oxide (AZO). In some embodiments, a conductive coating includes fluorine doped tin oxide (FTO).

The fluidics dispenser may be coupled to a heating element that provides for heat transfer to fluid passing through the fluid dispenser. The system 305 further includes an imaging system configured to detect at least one feature (e.g., one or more features) in the microplate 405. In embodiments, the fluidic dispenser is static (i.e., does not move) relative to the microplate receiver.

Figure 6:
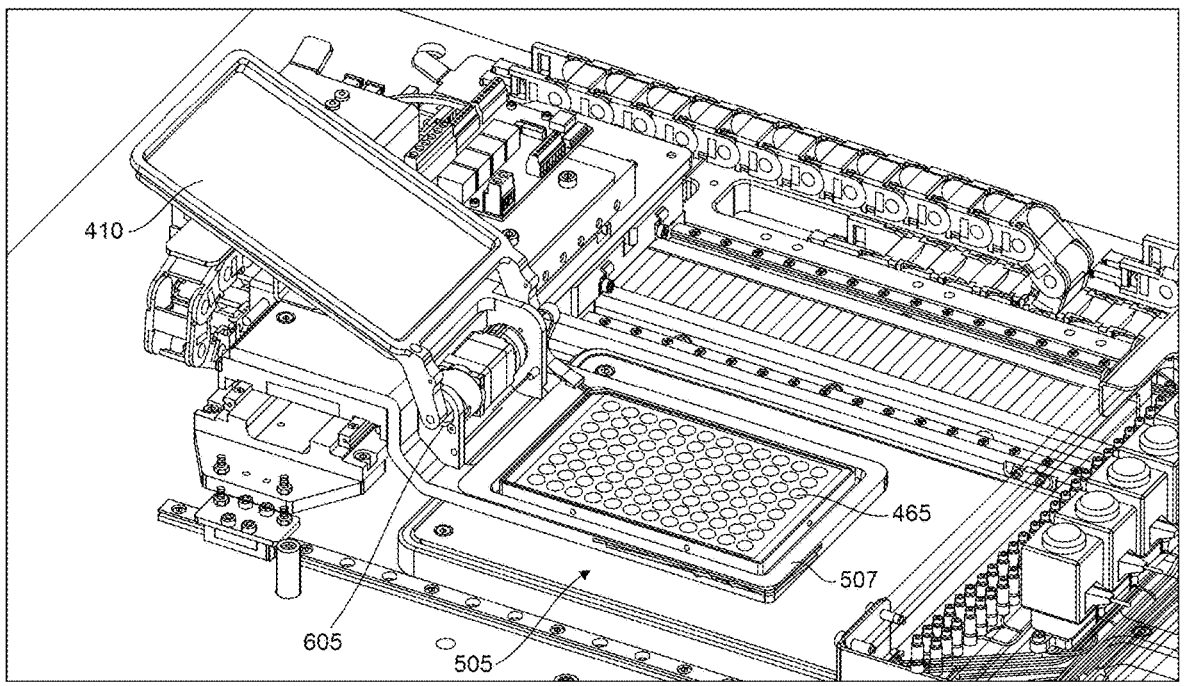
FIG. 6. shows a perspective view of an example embodiment of a sample stage assembly of the device. The lid 410 is attached to the microplate receiver 505 via a hinge assembly 605, which is configured to enable the lid 410 to move between a raised or open position (relative to the microplate receiver 505) and closed position relative to the microplate receiver 505.

With reference still to FIGS. 5-6, a lid 410 is movably attached to the microplate receiver 505. The lid is sized and shaped to be able to enclose or cover a microplate 405 positioned on the microplate receiver 507. As shown in FIG. 6, the lid 410 is attached to the microplate receiver 505 via a hinge assembly 605, which is configured to enable the lid 410 to move between a raised or open position (relative to the microplate receiver 505) and closed position relative to the microplate receiver 505. In an embodiment, the lid 410 transitions between the open and closed positions via a rotational or pivoting movement although the type of movement can vary.

Figure 7:
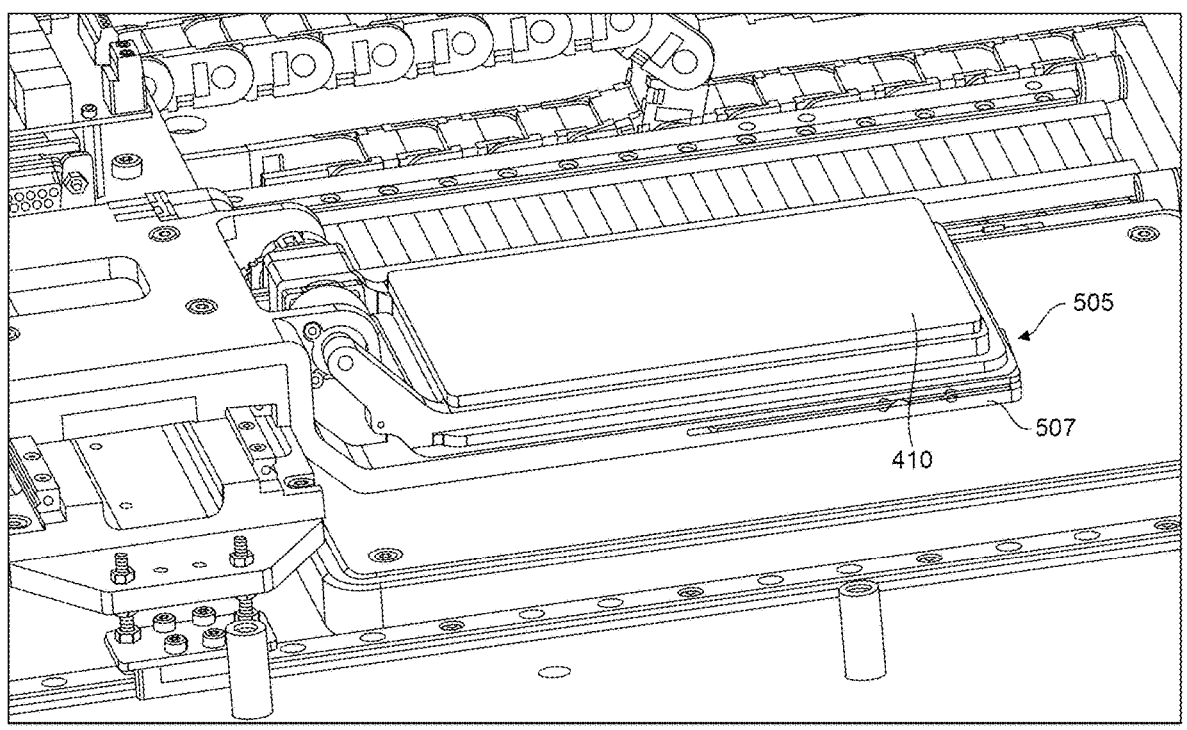
FIG. 7. shows the lid 410 in the closed position wherein the lid 410 is juxtaposed with the platform 507 and the microplate receiver 505. The lid 410 encloses the microplate receiver 505 relative to the platform 507 when the lid 410 is closed.
Figure 8A:
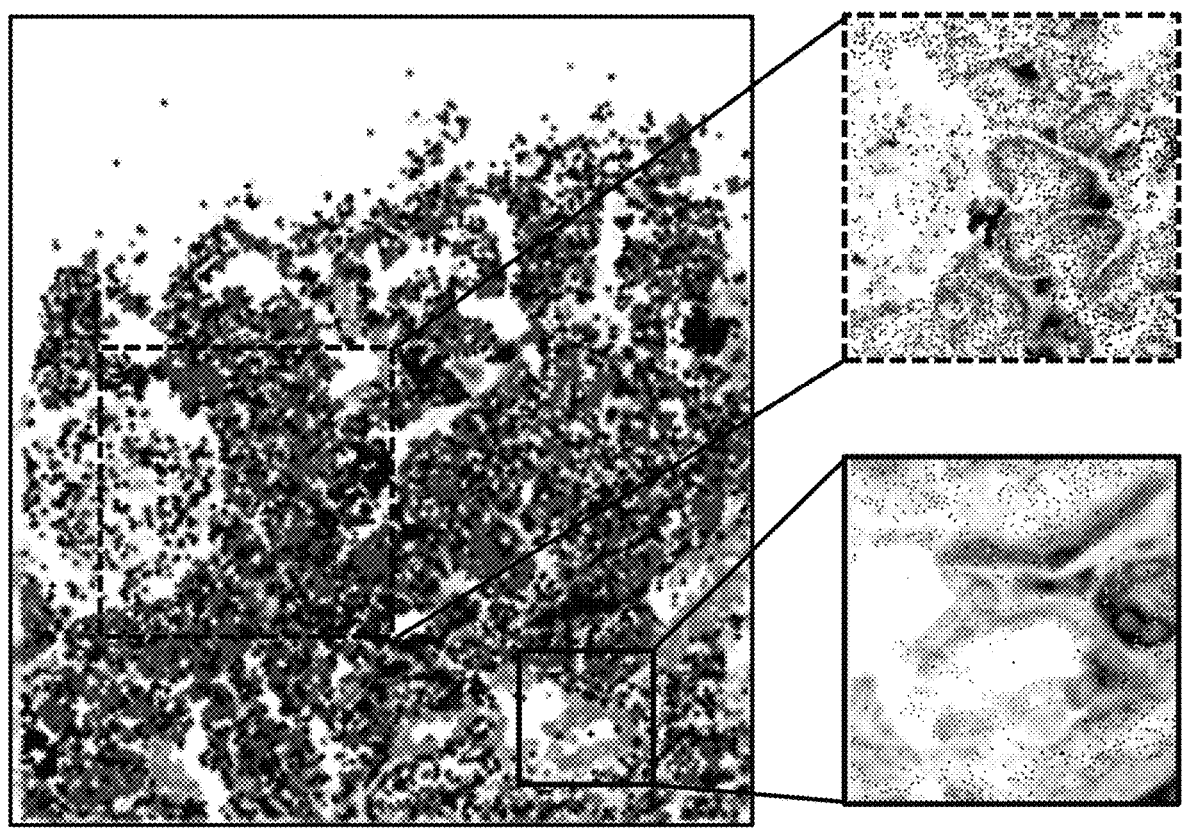
FIGS. 8A-8C. provide images of a tissue sample obtained from the device described herein, wherein the detected transcripts and proteins are associated with the expected tissue morphology.
Figure 8B:
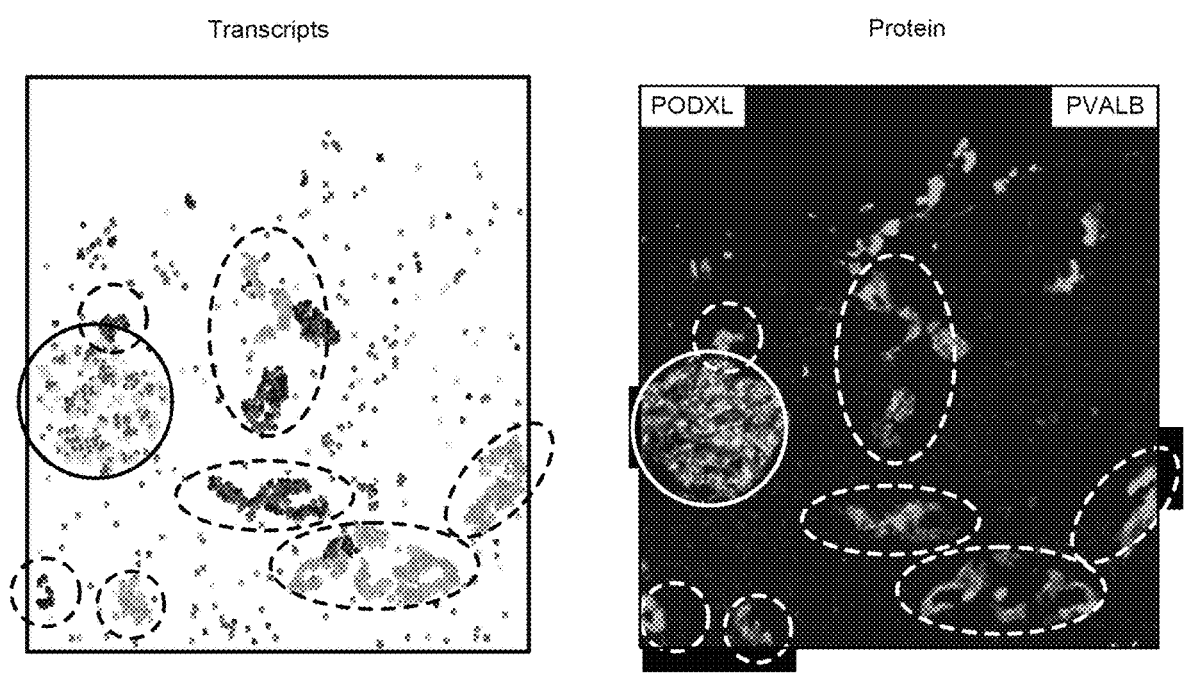
Figure 8C:
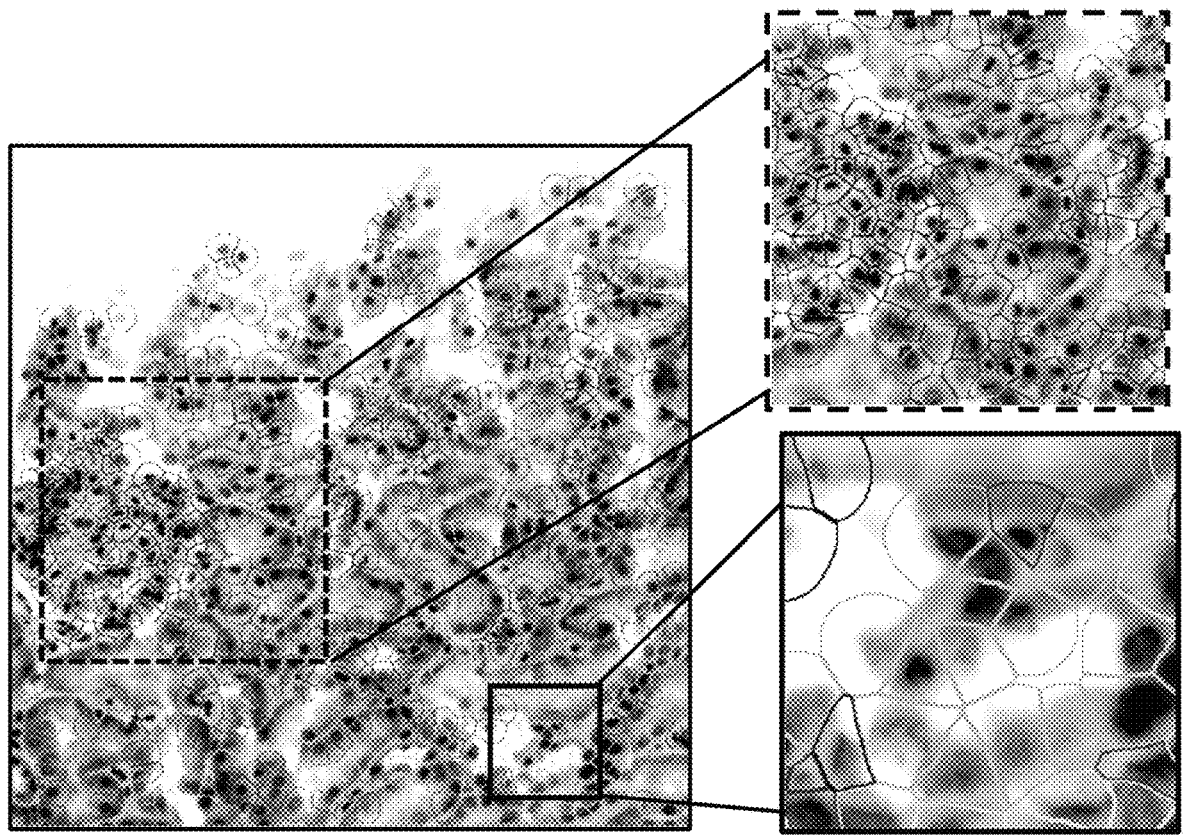
Figure 9A:
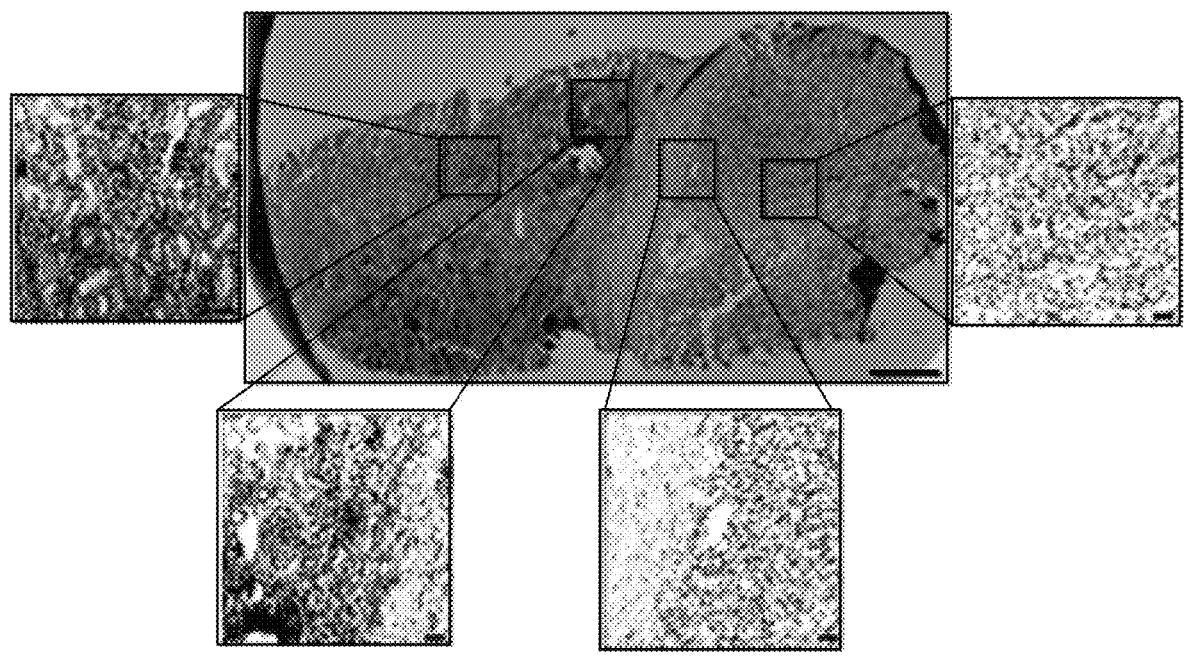
FIGS. 9A-9B provides images of a kidney tumor section obtained with the device described herein. Also depicted are magnified regions indicating that the left side of the kidney tumor section is relatively healthy and retains the expected tubule morphology, but gradually breaks down when moving across the sample (i.e., to the right) and into the diseased region. The device and methods described herein facilitates diagnoses which can impact clinical outcomes. The images were obtained using the following imaging parameters: Complete Section Scale: 500 um; 4× objective; and Zoomed insets: Scale: 200 um; 20× objective.
Figure 9B:
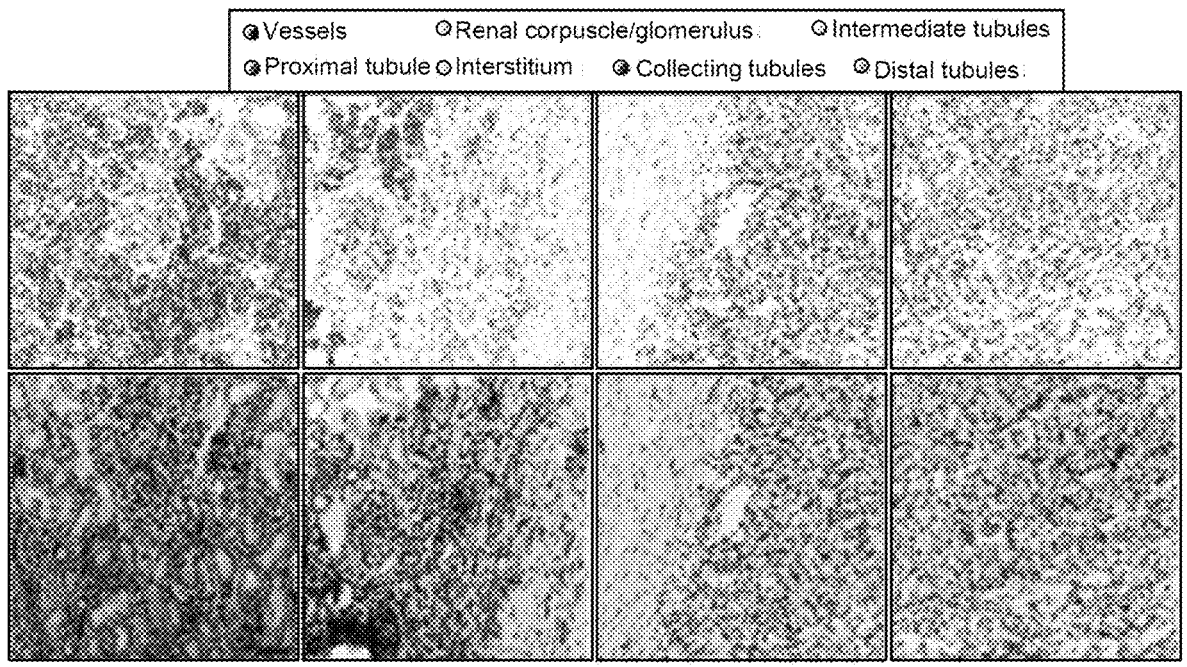

FIGS. 5-6 shows the lid 410 in the open position wherein at least a portion of the lid 410 is spaced from the microplate receiver 505 and the microplate 405 such that at least a top surface of the microplate 405 is exposed. The lid 410 is raised relative to the microplate 405 to provide access to the microplate 405 when open. FIG. 7 shows the lid 410 in the closed position wherein the lid 410 is juxtaposed with the platform 507 and the microplate receiver 505 with the microplate 405 enclosed. The lid 410 encloses the microplate 405 relative to the platform 507 when the lid 410 is closed. The lid 410 and/or another portion of the system 305, such as the platform 507 and/or the cover 323, thus define a containment structure that defines an enclosed, temperature-controlled region. In this regard, the lid 410 is configured to be heated or to provide heat. The lid 410 can be thermally coupled to or can contain one or more heating elements for providing heat to and controlling the temperature-controlled region. In another embodiment, the temperature-controlled region is the entire space contained within the cover 323. In embodiments, the containment structure is an enclosed, temperature-controlled region with a defined humidity.

In an aspect is provided a device including: a sample stage configured to be coupled to a microplate receiver; a microplate receiver configured to be coupled to a microplate; at least one heating element thermally coupled to the microplate receiver; a fluidics dispenser configured to dispense one or more reagents into the microplate; and an imaging system configured to detect at least one feature (e.g., one or more features) in the microplate; and a structure physically coupled to the sample stage, the heating element, the fluidics dispenser, and the imaging system. In embodiments, the sample stage retains the microplate. In embodiments, the structure includes a support structure formed of a base platform or a table. In embodiments, the one or more features include a reaction chamber and its contents. In embodiments, the one or more features includes a target (e.g., a nucleic acid, protein, or biomarker), a cell, or a tissue sample. In embodiments, the feature is a nucleotide (e.g., a fluorescently labeled nucleotide). In embodiments, the feature is a nucleic acid. In embodiments, the feature is a protein. In embodiments, the feature is a biomolecule.

In embodiments, the imaging system is configured to detect one or more fluorescent features in the microplate. In embodiments, the imaging system is configured to detect one or more fluorescent nucleotides in the microplate. In embodiments, the imaging system configured to detect one or more features in each reaction chamber (e.g., well) of the microplate. In embodiments, the imaging system configured to detect the cellular morphology of a cell. In embodiments, the imaging system configured to image the cell and characterize the cell morphology (e.g., the cell boundary, granularity, or cell shape). In embodiments, the imaging system configured to obtain images of a histologically-stained cell. In embodiments, the imaging system is configured to detect fluorescently-labeled nucleotides and obtain structural information about a cell on the microplate.

In an aspect is provided a microplate array, including: a substrate including a surface, the surface comprising a plurality of wells separated from each other by interstitial regions on the surface, wherein one or more wells includes a sample (e.g., a cell or tissue sample), particle, or nucleic acid. In embodiments, the sample includes a cell. In embodiments, the sample includes a particle. In embodiments, the sample includes a nucleic acid. In embodiments, the sample is a tissue sample. In embodiments, the sample includes a cell. In embodiments, the surface is substantially free of oligonucleotides. In embodiments, the microplate array includes 2, 4, 6, 12, 24, 48, 96, 384 or 1536 wells. In embodiments, the microplate array includes 24, 48, 96, or 384 wells. In embodiments, the microplate array includes 24 wells. In embodiments, the microplate array includes 48 wells. In embodiments, the microplate array includes 96 wells. In embodiments, the microplate array includes 384 wells. In embodiments, the dimensions of the microplate conform to the standards provided by the American National Standards Institute (ANSI) and Society For Laboratory Automation And Screening (SLAS); for example the tolerances and dimensions set forth in ANSI SLAS 1-2004 (R2012); ANSI SLAS 2-2004 (R2012); ANSI SLAS 3-2004 (R2012); ANSI SLAS 4-2004 (R2012); and ANSI SLAS 6-2012. In embodiments, the microplate has a rectangular shape that measures 127.7 mm±0.5 mm in length by 85.4 mm±0.5 mm in width, and includes 6, 12, 24, 48, or 96 wells. In embodiments, the microplate has a rectangular shape that measures 127.7 mm±0.5 mm in length by 85.4 mm±0.5 mm in width, and includes 6, 12, 24, 48, or 96 wells, wherein each well has an average diameter of about 5-7 mm. In embodiments, the microplate has a rectangular shape that measures 127.7 mm±0.5 mm in length by 85.4 mm±0.5 mm in width, and includes 6, 12, 24, 48, or 96 wells, wherein each well has an average diameter of about 6 mm. In embodiments, the microplate includes an array of femoliter wells, array of nanoliter wells, or array of microliter wells. In embodiments, the wells in an array may all have substantially the same volume. The array of wells may have a volume up to 100 e.g., about 0.1 femtoliter, 1 femtoliter, 10 femtoliter, 25 femtoliter, 50 femtoliter, 100 femtoliter, 0.1 pL, 1 pL, 10 pL, 25 pL, 50 pL, 100 pL, 0.1 nL, 1 nL, 10 nL, 25 nL, 50 nL, 100 nL, 0.1 microliter, 1 microliter, 10 microliter, 25 microliter, 50 microliter, or 100 microliter.

In embodiments, the microplate includes a plurality of wells. In embodiments, each well includes about 10,000 to 100,000 cells per well. In embodiments, each well includes at least 1000, 2000, 3000, 4000, 5000, 6000, 7000, 8000, 9000 or at least 10,000 cells per well. In embodiments, each well includes about 10,000, 20,000, 30,000, 40,000, 50,000, 60,000, 70,000, 80,000, 90,000 or at least 100,000 cells per well.

In embodiments, each well includes a sample. In embodiments, each well includes one or more cells. In embodiments, a portion of the microplate includes a biological sample, e.g., about 10% to about 99%, about 10% to about 95%, about 10% to about 90%, about 10% to about 85%, about 10% to about 80%, about 10% to about 75%, about 10% to about 70%, about a 10% to about 65%, about 10% to about 60%, about 10% to about 55%, about 10% to about 50%, about 10% to about 45%, about 10% to about 40%, about 10% to about 35%, about 10% to about 30%, about 10% to about 25%, about 10% to about 20%, about 10% to about 15%, about 15% to about 99%, about 15% to about 95%, about 15% to about 90%, about 15% to about 85%, about 15% to about 80%, about 15% to about 75%, about 15% to about 70%, about a 15% to about 65%, about 15% to about 60%, about 15% to about 55%, about 15% to about 50%, about 15% to about 45%, about 15% to about 40%, about 15% to about 35%, about 15% to about 30%, about 15% to about 25%, about 15% to about 20%, about 20% to about 99%, about 20% to about 95%, about 20% to about 90%, about 20% to about 85%, about 20% to about 80%, about 20% to about 75%, about 20% to about 70%, about a 20% to about 65%, about 20% to about 60%, about 20% to about 55%, about 20% to about 50%, about 20% to about 45%, about 20% to about 40%, about 20% to about 35%, about 20% to about 30%, about 20% to about 25%, about 25% to about 99%, about 25% to about 95%, about 25% to about 90%, about 25% to about 85%, about 25% to about 80%, about 25% to about 75%, about 25% to about 70%, about a 25% to about 65%, about 25% to about 60%, about 25% to about 55%, about 25% to about 50%, about 25% to about 45%, about 25% to about 40%, about 25% to about 35%, about 25% to about 30%, about 30% to about 99%, about 30% to about 95%, about 30% to about 90%, about 30% to about 85%, about 30% to about 80%, about 30% to about 75%, about 30% to about 70%, about a 30% to about 65%, about 30% to about 60%, about 30% to about 55%, about 30% to about 50%, about 30% to about 45%, about 30% to about 40%, about 30% to about 35%, about 35% to about 99%, about 35% to about 95%, about 35% to about 90%, about 35% to about 85%, about 35% to about 80%, about 35% to about 75%, about 35% to about 70%, about a 35% to about 65%, about 35% to about 60%, about 35% to about 55%, about 35% to about 50%, about 35% to about 45%, about 35% to about 40%, about 40% to about 99%, about 40% to about 95%, about 40% to about 90%, about 40% to about 85%, about 40% to about 80%, about 40% to about 75%, about 40% to about 70%, about a 40% to about 65%, about 40% to about 60%, about 40% to about 55%, about 40% to about 50%, about 40% to about 45%, about 45% to about 99%, about 45% to about 95%, about 45% to about 90%, about 45% to about 85%, about 45% to about 80%, about 45% to about 75%, about 45% to about 70%, about a 45% to about 65%, about 45% to about 60%, about 45% to about 55%, about 45% to about 50%, about 50% to about 99%, about 50% to about 95%, about 50% to about 90%, about 50% to about 85%, about 50% to about 80%, about 50% to about 75%, about 50% to about 70%, about a 50% to about 65%, about 50% to about 60%, about 50% to about 55%, about 55% to about 99%, about 55% to about 95%, about 55% to about 90%, about 55% to about 85%, about 55% to about 80%, about 55% to about 75%, about 55% to about 70%, about a 55% to about 65%, about 55% to about 60%, about 60% to about 99%, about 60% to about 95%, about 60% to about 90%, about 60% to about 85%, about 60% to about 80%, about 60% to about 75%, about 60% to about 70%, about a 60% to about 65%, about 65% to about 99%, about 65% to about 95%, about 65% to about 90%, about 65% to about 85%, about 65% to about 80%, about 65% to about 75%, about 65% to about 70%, about 70% to about 99%, about 70% to about 95%, about 70% to about 90%, about 70% to about 85%, about 70% to about 80%, about 70% to about 75%, about 75% to about 99%, about 75% to about 95%, about 75% to about 90%, about 75% to about 85%, about 75% to about 80%, about 80% to about 99%, about 80% to about 95%, about 80% to about 90%, about 80% to about 85%, about 85% to about 99%, about 85% to about 95%, about 85% to about 90%, about 90% to about 99%, about 90% to about 95%, or about 95% to about 99%, of the wells include a biological sample.

In embodiments, the sample stage is mobile (e.g., capable of at least moving in the xy plane). In embodiments, the sample stage is a motorized translation stage. In embodiments, the sample stage is configured to receive and retain a microplate receiver and/or a microplate. In embodiments, the sample stage is configured to receive and retain a microplate receiver and a microplate containing a sample. In embodiments, the device further includes one or more "fascia plates", or covers, that hides fasteners, circuit boards, and similar delicate components, protecting them from dust and/or human contact, and providing visual appeal. In embodiments, the sample stage is capable of moving independently relative to imaging system. For example, the sample stage may translate (e.g., 0.5 mm to 100 mm) in the xy plane while the camera rotates about a longitudinal and/or transverse axis. In embodiments, the sample stage may translate in the xy plane while the camera remains static. In embodiments, the base platform is capable of rotating relative to the xy plane of the sample on the sample stage. In embodiments, the sample stage is capable of translating in an xy plane, and the image sensor is capable of moving along a polar angle formed between the z axis and the normal vector of the xy plane. In embodiments, the sample stage is capable of translating only in an xy plane, and the image sensor is capable of moving along a polar angle formed between the z axis and the normal vector of the xy plane. In embodiments, the sample stage is mobile (e.g., capable of at least moving in the xy plane). In embodiments, the sample stage is a motorized translation stage. In embodiments, the motorized translation stage includes at least one motor attached (connected) to the sample stage. In embodiments, the motor is a stepper motor, piezo motor, brushless motor, hysteresis motor, linear motor, or a servomotor. In embodiments, the motor is a stepper motor. In embodiments, the stepper motor includes an integrated ball spline. In embodiments, the motor is a piezo motor. In embodiments, the motor is a brushless motor. In embodiments, the motor is a hysteresis motor. In embodiments, the motor is a linear motor. In embodiments, the motor is a servomotor. In embodiments, the servomotor includes a braking mechanism.

In embodiments, the sample stage is not configured to rotate about the longitudinal axis. In embodiments, the sample stage is not configured to rotate about the transverse axis. In embodiments, the sample stage is not configured to tip or tilt (e.g., tip or tilt relative to the xy plane). In embodiments, the sample stage is not configured to tilt (e.g., tilt relative to the xy plane). In embodiments, the xy plane is dynamically determined as the sample is scanned (e.g., continuously scanned in a scan axis, such as the x axis). The system may further include a scanning element, which may be a mechanical, electro-mechanical component, software component, or combination thereof configured to scan the sample along a direction, which may correspond to a scan direction. In an embodiment, the scan direction is orthogonal to the excitation direction of the sample. In an embodiment, the scan direction is non-orthogonal to the excitation beam direction, wherein the orthogonal projected component directly contributes to the final image reconstruction. The term "scanning element" is intended to mean an element capable of sequentially detecting different portions of a sample. A scanning element can operate, by changing the position of one or more component of the system including, for example, the light source the objective lens, the image sensor, or the sample. Exemplary scanning elements include, but are not limited to a galvanometer configured to move a beam (e.g., excitation beam) across a sample or a translation stage configured to move the sample across the beam. In embodiments, the sample is scanned at about 1 $mm^2$/sec, 1.5 $mm^2$/sec, 5 $mm^2$/sec, 10 $mm^2$/sec, 50 $mm^2$/sec or 100 $mm^2$/sec. In embodiments, the sample is scanned at 10 $mm^2$/sec, 20 $mm^2$/sec, 30 $mm^2$/sec, 40 $mm^2$/sec, or 50 $mm^2$/sec. In embodiments, the sample is scanned at least 20 $mm^2$/sec.

In embodiments, the microplate includes wells that are formatted for compatibility with automated reagent loading equipment (e.g., pipetting robots) that already exist and are in common usage in laboratories and manufacturing facilities.

In embodiments, the microplate includes a plurality of wells, wherein one or more wells include a particle. In embodiments, the particle includes a plurality of oligonucleotide moieties. In embodiments, there is at least one particle per well. In embodiments, there is at most one particle per well. In embodiments, the particles are non-covalently attached to the wells. In embodiments, the particles are physiosorbed to the wells. In embodiments, each particle attaches to the polymer layer of the surface (e.g., non-covalently attach to the polymer layer). In some embodiments, the particle is a functionalized particle including a particle core and a particle shell, wherein said particle shell includes the plurality of oligonucleotide moieties, wherein each of the oligonucleotide moieties includes a linker binding the oligonucleotide to the particle core. In some embodiments, the particle core includes glass, ceramic, metal, silica, magnetic material, or a paramagnetic material. The particle core may be an inorganic particle core. The inorganic particle core may be a metal particle core. When the particle core is a metal, the metal may be titanium, zirconium, gold, silver, platinum, cerium, arsenic, iron, aluminum or silicon.

The metal particle core may be titanium, zirconium, gold, silver, or platinum and appropriate metal oxides thereof. In embodiments, the particle core is titanium oxide, zirconium oxide, cerium oxide, arsenic oxide, iron oxide, aluminum oxide, or silicon oxide. The metal oxide particle core may be titanium oxide or zirconium oxide. The particle may be titanium. The particle may be gold. The particle may be silicon dioxide. The particle may be silica. In embodiments, the particle core is in the form of a bead. For example, the core/shell layers may be formed around a supporting structure, for example, a silica, magnetic, or paramagnetic bead. In some embodiments, the composition includes a solid bead support (which itself may include a magnetic core and an encapsulating polymer layer), a functional core layer around the bead for primer attachment, and a shell polymer layer in which no amplification reactions take place. In embodiments, the particle is a silica particle includes a magnetic core, and a copolymer shell. In embodiments, the particle shell is chemically distinct from the particle core. In embodiments, the average longest dimension of the particle is from about 100 nm to about 400 nm. In embodiments, the average longest dimension of the particle is from about 200 nm to about 700 nm. In embodiments, the average longest dimension of the particle is less than about 1000 nm.

In some embodiments, the wells of the array are separated from each other by about 1 mm to about 10 mm. In embodiments, the well is about 3 mm in diameter. In embodiments, the well is about 3.6 mm in diameter. In embodiments, the well is about 4 mm in diameter. In embodiments, the well is about 5 mm in diameter. In embodiments, the well is about 6 mm in diameter. In embodiments, the well is about 6.5 mm in diameter. In embodiments, the well is about 7 mm in diameter. In embodiments, the well is about 7.5 mm in diameter. In embodiments, the well is about 8 mm in diameter. In embodiments, the well is 5 mm in diameter. In embodiments, the well is 6 mm in diameter. In embodiments, the well is 6.5 mm in diameter. In embodiments, the well is 7 mm in diameter. In embodiments, the well is 7.5 mm in diameter. In embodiments, the well is 8 mm in diameter. In embodiments, the well is about 6 to 12 mm in depth. It is also understood that the size of the wells on the array can be of various sizes and will ultimately depend on the systems and/or apparatus used to analyze later reactions.

In embodiments, the microplate and wells are comprised of the same material. Though typically glass, suitable microplate materials may include polymeric materials, plastics, silicon, quartz (fused silica), Borofloat® glass, silica, silica-based materials, carbon, metals, an optical fiber or optical fiber bundles, sapphire, or plastic materials such as COCs and epoxies. The material can be selected based on properties desired for a particular use. For example, materials that are transparent to a desired wavelength of radiation are useful for analytical techniques that will utilize radiation of the desired wavelength. Conversely, it may be desirable to select a material that does not pass radiation of a certain wavelength (e.g., being opaque, absorptive, or reflective). In embodiments, at least a portion of the bottom of the wells is transparent and the sides (i.e., walls) of the wells are opaque. In embodiments, the material of the microplate is selected due to the ability to conduct thermal energy. In embodiments, the microplate is capable of being removed from the microplate receiver. In embodiments, the microplate and wells are comprised of different materials. In embodiments, the microplate is black. Black microplates are well-suited for fluorescence-based readouts, which have higher signal intensities than luminescence.

In embodiments, the well contains a gel. The term "gel" in this context refers to a semi-rigid solid that is permeable to liquids and gases. Exemplary gels include, but are not limited to, those having a colloidal structure, such as agarose; polymer mesh structure, such as gelatin; or cross-linked polymer structure, such as polyacrylamide or a derivative thereof. Analytes, such as polynucleotides, can be attached to a gel or polymer material via covalent or non-covalent means. Exemplary methods and reactants for attaching nucleic acids to gels are described, for example, in US 2011/0059865 which is incorporated herein by reference. The analytes, sample, tissue, or cell can include nucleic acids and the nucleic acids can be attached to the gel or polymer via their 3' oxygen, 5' oxygen, or at other locations along their length such as via a base moiety of the 3' terminal nucleotide, a base moiety of the 5' nucleotide, and/or one or more base moieties elsewhere in the molecule. In embodiments, the microplate includes a polymer layer (alternatively referred to as a polymer coating). In embodiments, the microplate includes a polymer layer, wherein the polymer layer includes an amphiphilic copolymer. The term "amphiphilic copolymer" is used in accordance with its ordinary meaning and refers to a copolymer composed of polymerized hydrophilic (e.g., PEG monomers) and hydrophobic monomers (e.g., alkoxysilyl or (poly(propylene oxide) monomers). Amphiphilic copolymers can have both hydrophilic and hydrophobic properties. In embodiments, the polymer layer includes an amphiphilic acrylate copolymer or amphiphilic methacrylate copolymer. In embodiments, the amphiphilic polymer includes a poloxamer. In some embodiments, the solid support includes a poloxamer layer. In some embodiments, the poloxamer is a polyoxyethylene-polyoxypropylene copolymer. In embodiments, the wells include a hydrogel. In embodiments, the wells include a sample (e.g., a biological sample such as a cell and/or tissue). In embodiments, the wells include a sample, wherein the sample includes an analyte of interest. Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In embodiments, the analytes within a cell can be localized to subcellular locations, including, for example, organelles, e.g., mitochondria, Golgi apparatus, endoplasmic reticulum, chloroplasts, endocytic vesicles, exocytic vesicles, vacuoles, lysosomes, etc. In embodiments, analyte(s) can be peptides or proteins, including antibodies and/or enzymes. In embodiments, an analyte can be detected indirectly, such as through detection of an intermediate agent, for example, a ligation product or an analyte capture agent (e.g., an oligonucleotide-conjugated antibody), such as those described herein.

In embodiments, the structure further includes a containment structure having a lid. In embodiments, the containment structure defines an enclosed, temperature-controlled region. In embodiments, the sample stage is positioned inside the temperature-controlled region. In embodiments, the lid is movable between an open position and a closed position relative to the microplate, and may be moved to any position between open and closed. In the open position, the lid does not obstruct access to the microplate. When in the closed position, the lid will block and/or obstruct access to the microplate from a location external to the enclosed region. The lid may be made of any suitable material capable of maintaining a temperature-controlled region encasing the microplate. Exemplary materials from which the lid may be made include, but are not limited to, glass, polymer (e.g., polyetherimide (PEI), polycarbonate, or polyetheretherketone (PEEK), ceramic, beryllium copper, spring steel, chrome vanadium, chrome silicon, phosphor bronze, stainless steel, aluminum, titanium, tungsten, metal alloys, metal composites, plastic, or any suitable rigid or semi-rigid material. In embodiments, the lid is made from aluminum. In embodiments, the lid is attached with a hinge (i.e., is rotatably mounted) so as to enable movement between the open and closed positions. As used herein, the term "rotatably mounted" refers to any mounting orientation that allows the rotatable member to rotate about its center axis. In embodiments, the containment structure includes a gasket between the lid and the device. In embodiments, the lid includes an access panel (e.g., a sliding access door) so as to allow the user to access the microplate.

In embodiments, the containment structure includes at least one transparent window. In embodiments, the window can be transparent to radiation in a particular spectral range including, but not limited to x-ray, ultraviolet (UV), visible (VIS), infrared (IR), microwave and/or radio wave radiation. In embodiments, one or more windows can provide a view to the microplate.

In embodiments, the device includes a humidity control module configured to control the humidity level of the air circulating within the temperature-controlled region. As part of this process, the humidity control module is optionally equipped to collect condensed water, and route it for disposal. In embodiments, the humidity of the device is measured with a hygrometer present in the temperature-controlled region. In embodiments, the humidity level of the air circulating within the temperature-controlled region is maintained between 80% and 95%. In embodiments, the humidity level of the air circulating within the temperature-controlled region is maintained between 80% and 85%. In embodiments, the humidity level of the air circulating within the temperature-controlled region is maintained between 85% and 90%. In embodiments, the humidity level of the air circulating within the temperature-controlled region is maintained between 90% and 95%. In embodiments, the humidity level of the air circulating within the temperature-controlled region is maintained below 80%, below 70%, below 60%, below 50%, below 40%, or below 30%. In embodiments, the humidity control module is optionally equipped to inject $CO_2$ into the air circulating within the temperature-controlled region. In embodiments, the $CO_2$ levels in the air circulating within the temperature-controlled region are maintained at between 1% to 10%. In embodiments, the $CO_2$ levels in the air circulating within the temperature-controlled region are maintained at between 1% to 3%. In embodiments, the $CO_2$ levels in the air circulating within the temperature-controlled region are maintained at between 3% to 5%. In embodiments, the $CO_2$ levels in the air circulating within the temperature-controlled region are maintained at between 5% to 7%. In embodiments, the $CO_2$ levels in the air circulating within the temperature-controlled region are maintained at between 7% to 10%.

In embodiments, the imaging system includes at least one of a kinematic mount and an auto-leveler mechanism. In embodiments, the imaging system includes a kinematic mount and an auto-leveler mechanism. In embodiments, the imaging system includes a kinematic mount. In embodiments, the imaging system includes an auto-leveler mechanism. The kinematic optical mount assembly provides a means of camera translocation relative to a microplate, and separates some of the degrees of freedom and permits the camera(s) to capture a greater number of in-focus images as the microplate moves. In embodiments, the kinematic optical mount assembly is motorized in a manner that allows for rapid tip and tilt adjustment of the kinematic optical mount assembly and the camera. In a non-limiting example, the kinematic optical mount assembly can include a quantity (such as a quantity of one, two, three, or four) stepper motors configured to positionally adjust the kinematic optical mount assembly. The positional adjustment of the camera, such as $X/Y/\theta$ adjustment of the camera, within the kinematic optical mount assembly allows centering of the image sensor (i.e., the camera) with respect to the optical axis and rotational alignment of the image sensor to patterned features in the microplate and/or the laser illumination area. This has the benefit of trimming out gross optical misalignment.

In embodiments, the imaging system includes at least one of a three-dimensional imager, a TDI scanner, a laser, a camera, an autofocus, and a transilluminator. In embodiments, the imaging system is configured to perform conventional immunohistochemical (IHC) imaging and immunofluorescence (IF) imaging. Examples of suitable imaging systems include optical waveguides, microscopes, diodes, light stimulating devices (e.g., lasers), photo multiplier tubes, processors (e.g., computers and software), and combinations thereof, which cooperate to detect a signal representative of a characteristic, marker, or target. In embodiments, the imaging system includes a CCD, EMCCD, or s-CMOS detector. In embodiments, the imaging system includes a light source that illuminates a sample, an objective lens, and a sensor array (e.g., complementary metal-oxide-semiconductor (CMOS) array or a charge-coupled device (CCD) array). In embodiments, the illuminator or light source is a radiation source (i.e., an origin or generator of propagated electromagnetic energy) providing incident light to the sample. A radiation source can include an illumination source producing electromagnetic radiation in the ultraviolet (UV) range (about 200 to 390 nm), visible (VIS) range (about 390 to 770 nm), or infrared (IR) range (about 0.77 to 25 microns), or other range of the electromagnetic spectrum. In embodiments, the illuminator or light source is a lamp such as an arc lamp or quartz halogen lamp. In embodiments, the illuminator or light source is a coherent light source. In embodiments, the light source is a laser, LED (light emitting diode), a mercury or tungsten lamp, or a super-continuous diode. In embodiments, the light source provides excitation beams having a wavelength between 200 nm to 1500 nm. In embodiments, the laser provides excitation beams having a wavelength of 405 nm, 470 nm, 488 nm, 514 nm, 520 nm, 532 nm, 561 nm, 633 nm, 639 nm, 640 nm, 800 nm, 808 nm, 912 nm, 1024 nm, or 1500 nm. In embodiments, the laser provides excitation beams having a wavelength of 405 nm, 488 nm, 532 nm, or 633 nm. In embodiments, the illuminator or light source is a light-emitting diode (LED). The LED can be, for example, an Organic Light Emitting Diode (OLED), a Thin Film Electroluminescent Device (TFELD), or a Quantum dot based inorganic organic LED. The LED can include a phosphorescent OLED (PHOLED). In embodiments, the device is configured to obtain images at various depths (e.g., different z depths) of a sample. For example, the device is capable of obtaining a image at a first depth and a second depth, wherein the first and second depth are separated by about 1.5 μm. In embodiments, the device is capable of obtaining multiple images at a plurality of depths (e.g., depths separated by about 1.5 μm intervals). In embodiments, the device obtains an image at different focus depths. In embodiments, the focus depths are at 0.0 (i.e., on the surface of the sample), −0.5, −1.0, −1.5, and −2.0 μm, wherein the negative sign indicates the length from the surface. In embodiments, the focus depths are separated at interval depths. In embodiments, the interval depths (e.g., delta z) are 0.1, 0.25, 0.5, 0.75, 1.0, 1.25, 1.5, 1.75, or 2.0 μm relative to the surface. For example, when the imaging system has an interval depth of 1.0 μm, wherein the total depth imaged is 5.0 μm relative to the surface of the sample. In embodiments, the imaging system is an imaging system as described in WO 2022/056385, which is incorporated herein by reference in its entirety for all purposes. In non-limiting example embodiments, the imaging system includes a light source that illuminates a sample, an objective lens, and a sensor array (e.g., complementary metal-oxide-semiconductor (CMOS) array or a charge-coupled device (CCD) array), wherein the sample is in a microplate, and the sensor array is on a detection stage.

In embodiments, the light source is a laser (e.g., a laser such as a solid state laser or a gas laser). In embodiments, the light source includes one or more vertical cavity surface emitting lasers (VCSELs), vertical external cavity surface emitting lasers (VECSELs), or diode pumped solid state (DPSS) lasers. In embodiments, the light source is a continuous wave (CW) laser or a pulsed laser. In embodiments, the light source is a pulsed laser. In embodiments, the light source is an ultrashort pulsed laser. An ultrashort laser is a laser capable of producing excitation beams for a time duration of a picosecond or less. An ultrashort laser typically includes additional components, such as a pulse controller, pulse shaper, and spatial light modulator, and the like for controlling the pulse of excitation beams. In embodiments, the ultrashort laser provides excitation beams for femtoseconds or picoseconds. In embodiments, the light source is a pulsed femtosecond or picosecond laser. In embodiments, the laser is a Ti-sapphire laser, a dye-laser, or a fiber laser. In embodiments, the system includes two or more light sources (e.g., lasers). In embodiments, the first light source configured to emit light in red wavelengths, and a second light source configured to emit light in green wavelengths. In embodiments, the device includes two or more lasers. In embodiments, the device includes two lasers. The system 305 may include safety features configured to limit unintentional exposure of the laser. For example, the system may include one or more kill switches that automatically turns off the laser when a predetermined condition is satisfied.

In embodiments, the imaging system includes components necessary to perform bright field microscopy, phase contrast microscopy, Nomarski differential-interference-contrast microscopy, or dark field microscopy. In embodiments, the imaging system includes either 2D or 3D fluorescent imaging modalities can be used. An advantage of 3D imaging is that a larger number of individual targets (e.g., proteins or nucleic acids) can be resolved within a single reaction chamber (e.g., a well). 3D fluorescent imaging methods include confocal microscopy, light sheet microscopy, and multi-photon microscopy. Suitable imaging technologies are known in the art, as exemplified by Larsson et al., Nat. Methods (2010) 7:395-397 and US Provisional application US/63/077,852; associated supplemental materials, the entire content of each is incorporated by reference herein in its entirety. In embodiments of the methods provided herein, the imaging is accomplished by confocal microscopy. Confocal fluorescence microscopy involves scanning a focused laser beam across the sample and imaging the emission from the focal point through an appropriately-sized pinhole. This suppresses the unwanted fluorescence from sections at other depths in the sample. In embodiments, the imaging is accomplished by multi-photon microscopy (e.g., two-photon excited fluorescence or two-photon-pumped microscopy). Unlike conventional single-photon emission, multi-photon microscopy can utilize much longer excitation wavelength up to the red or near-infrared spectral region. This lower energy excitation requirement enables the implementation of semiconductor diode lasers as pump sources to significantly enhance the photostability of materials. Scanning a single focal point across the field of view is likely to be too slow for many sequencing applications. To speed up the image acquisition, an array of multiple focal points can be used. The emission from each of these focal points can be imaged onto a detector, and the time information from the scanning mirrors can be translated into image coordinates. Alternatively, the multiple focal points can be used just for the purpose of confining the fluorescence to a narrow axial section, and the emission can be imaged onto an imaging detector, such as a CCD, EMCCD, or s-CMOS detector. A scientific grade CMOS detector offers an optimal combination of sensitivity, readout speed, and low cost. One configuration used for confocal microscopy is spinning disk confocal microscopy. In 2-photon microscopy, the technique of using multiple focal points simultaneously to parallelize the readout has been called Multifocal Two-Photon Microscopy (MTPM). Several techniques for MTPM are available, with applications typically involving imaging in biological tissue. In embodiments of the methods provided herein, the imaging is accomplished by light sheet fluorescence microscopy (LSFM). In embodiments, detecting includes 3D structured illumination (3DSIM). In 3DSIM, patterned light is used for excitation, and fringes in the Moiré pattern generated by interference of the illumination pattern and the sample, are used to reconstruct the source of light in three dimensions. In order to illuminate the entire field, multiple spatial patterns are used to excite the same physical area, which are then digitally processed (e.g., aligned relative to other images) to reconstruct the final image. See York, Andrew G., et al. "Instant super-resolution imaging in live cells and embryos via analog image processing." *Nature methods* 10.11 (2013): 1122-1126 which is incorporated herein by reference. In embodiments, detecting includes selective planar illumination microscopy, light sheet microscopy, emission manipulation, pinhole confocal microscopy, aperture correlation confocal microscopy, volumetric reconstruction from slices, deconvolution microscopy, or aberration-corrected multifocus microscopy. In embodiments, detecting includes digital holographic microscopy (see for example Manoharan, V. N. Frontiers of Engineering: Reports on Leading-edge Engineering from the 2009 Symposium, 2010, 5-12, which is incorporated herein by reference). In embodiments, detecting includes confocal microscopy, light sheet microscopy, or multi-photon microscopy.

In embodiments, the imaging system is configured to perform histochemistry analysis (e.g., imaging a stained cell, wherein the stain is hematoxylin and eosin stain (or haematoxylin and eosin stain or hematoxylin-eosin stain; often abbreviated as H&E stain or HE stain)). H&E is the combination of two histological stains: hematoxylin and eosin. The hematoxylin typically stains cell nuclei blue, and eosin typically stains the extracellular matrix and cytoplasm pink, with other structures taking on different shades, hues, and combinations of these colors. In embodiments, the device is configured to image a cell (e.g., one or more cells within each reaction chamber of the microplate). Alternative histological stains are known in the art, for example 4', 6-diamidino-2-phenylindole (DAPI), acid fast, alkaline phosphatase, Bielschowsky Stain, Congo Red, Gram Stain, Grocott-Gomori's (or Gömöri) Methenamine Silver, Hoechst stain, Luxol® Fast Blue, Methylene Blue, Oil Red O, Periodic-acid Schiff, Perl's Prussian Blue, Sudan Black B, Toluidine Blue, Trichrome, Verhoeff-van Gieson Stain, or Warthin-Starry.

In embodiments, the imaging system may also include other components, including a collection of lenses (such as a collimating lens, a beam shaping lens (e.g., Powell lens), and a cylindrical lens), mirrors (e.g., a dichromatic mirror), beam splitter, one or more pinhole apertures, excitation filter, or combinations thereof. For example, the direction, size, and/or polarization of the light source may be adjusted by using lenses, mirrors, and/or polarizers. In embodiments, one or more of the components of the system may be adjusted or manipulated automatically. Automatic control devices may include a motorized translation stage, an actuation device, one or more piezo stages, and/or one or more automatic switch and flip mirrors and lenses. In embodiments, the system includes one or more optical components (e.g., a beam shaping lens) configured to shape the light emitted from the one or more light sources into desired patterns. For example, in some embodiments, the optical components may shape the light into line patterns (e.g., by using one or more Powell lenses, or other beam shaping lenses, diffractive, or scattering components). In embodiments, the optical component includes a line generator. A "line generator" as used herein refers to an optical component that is configured to generate a diffraction-limited or near diffraction-limited excitation beam in the plane perpendicular to the optical axis of propagation with a substantially uniform intensity distribution along the horizontal axis of the line. Exemplary line generators include, but are not limited to, a one dimensional diffuser having angular uniformity, cylindrical micro-lens array, diffractive element or aspheric refractive lens such as a Powell lens. In embodiments, the optical components include a Powell lens, a micro-lens, or micro-lens array. In embodiments, the optical component includes a micro-lens fabricated on glass, metal, or plastic. In embodiments, the excitation beams may be directed through a beam shaping lens or lenses. In some embodiments, a single beam shaping lens may be used to shape the excitation beams output from a plurality light sources (e.g., 2 light sources). In some embodiments, a separate beam shaping lens may be used for each light beam. In embodiments, the beam shaping lens is a Powell lens, alternatively referred to as a Powell prism. The shape of the beam may be shaped into an appropriate geometry according to known techniques, e.g., a line, conical, super-Gaussian, ring, doughnut, Bessel-Gauss, Hermite-Gaussian, Laguerre-Gaussian, Hypergeometric-Gaussian, Ince-Gaussian, and the like. In embodiments, the beam is uniform within acceptable limits (e.g., less than 30% intensity variation across the beam). In embodiments, the beam is profiled or includes a gradient.

In embodiments, the image system includes an image sensor. In embodiments, the image sensor is a CMOS array. A CMOS array, alternatively referred to as a CMOS camera, typically use an active-pixel sensor (APS) that is an image sensor comprising of an integrated circuit containing an array of pixels, where each pixel includes a photodetector and an active amplifier. In embodiments, the image sensor includes a PIN photodiode, a CCD array, a CMOS array, a line scanner, a photodiode, a phototransistor, a photomultiplier, or an avalanche photodiode. In embodiments, the image sensor is a CCD array. In embodiments, the image sensor includes a confocal time delay and integration (TDI) line scan imaging system that has high S/N ratio and high confocality for producing high resolution images of a sample. The image sensor may be or include a complementary metal-oxide-semiconductor (CMOS) array, a charge-coupled device (CCD) array, an array of photodiodes, an array of avalanche photodiodes, an array of photomultiplier tubes (PMTs), or an array of optical fibers. In embodiments, the image sensor is at least one of a complementary metal-oxide-semiconductor (CMOS) array and a charge-coupled device (CCD) array. In an embodiment, the image sensor is a camera. In an embodiment, the image sensor is a plurality of cameras. In an embodiment, the image sensor includes four cameras. In an embodiment, the image sensor is two cameras. In an embodiment, the image sensor is a single camera. In an embodiment, the image sensor is an array of optical fibers. Each camera is configured to move independently from each other to increase or maximize the coincidence of the image plane to minimize second order aberrations as the sample moves in the scan dimension. In embodiments, the cameras include an objective lens having high numerical aperture (NA) values. For example, the NA may be at least about 0.65, 0.7, 0.75, 0.8, 0.85, 0.9, 0.95, or higher. Those skilled in the art will appreciate that NA, being dependent upon the index of refraction of the medium in which the lens is working, may be higher including, for example, up to 1.0 for air, 1.33 for pure water, or higher for other media such as oils. However, other embodiments may have lower NA values than the examples listed above. In embodiments, the objective lens includes a numerical aperture less than 1.0. In embodiments, the objective lens includes a numerical aperture of 0.1 to 1.65. In embodiments, the objective lens includes a numerical aperture of 0.1 to 0.95. In embodiments, the objective lens includes a numerical aperture of 1.0 to 1.65. In embodiments, the objective lens includes a numerical aperture of at least 0.2, 0.3, 0.4, or 0.5. In embodiments, the objective lens includes a numerical aperture is no greater than 0.8, 0.7, 0.6 or 0.5. In embodiments, the objective lens includes a numerical aperture is no greater than 1.4, 1.3, 1.2, 1.1, or 1.0. Image data obtained by the optical assembly may have a resolution that is between 0.1 and 50 microns or, more particularly, between 0.1 and 10 microns. In embodiments, the numerical aperture for the camera is at least 0.2. In embodiments, the numerical aperture for the camera is no greater than 0.8. In embodiments, the numerical aperture for the camera is no greater than 0.5. Image systems described herein may have a resolution that is sufficient to individually resolve the features or sites that are separated by a distance of less than 10 μm, 5 μm, 2 μm, 1.5 μm, 1.0 μm, 0.8 μm, 0.5 μm, or less. In embodiments, the image systems described herein may have a resolution that is sufficient to individually resolve the features or sites that are separated by a distance of 100 μm at most. In embodiments, the imaging system may generate image data, for example, at a resolution between 0.1 and 50 microns, which is then forwarded to a control/processing system within the bioanalytical instrument. The control/processing system may perform various operations, such as analog-to-digital conversion, scaling, filtering, and association of the data in multiple frames to appropriately and accurately image multiple sites at specific locations on a sample. The control/processing system may store the image data and may ultimately forward the image data to a post-processing system where the data is further analyzed. For example, further analysis may include determining nucleotide sequence information from the image data. In embodiments, the control/processing system may include hardware, firmware, and software designed to control operation of the bioanalytical instrument. The image data may be analyzed by the bioanalytical instrument itself, or may be stored for analysis by other systems and at different times subsequent to imaging. The data and files generated from the methods and analyses described herein may be a typical format, such as FASTQ files, FASTA files, binary alignment files (bam), .bcl, .vcf, and/or .csv files. The output files may be in file formats that are compatible with available sequence data viewing, modification, annotation, and/or additional manipulation software.

In embodiments, the device as described herein detects scattered light from the sample. In embodiments, the device as described herein detects diffracted light from the sample. In embodiments, the device as described herein detects reflected light from the sample. In embodiments, the device as described herein detects absorbed light from the sample. In embodiments, the device as described herein detects refracted light from the sample. In embodiments, the device as described herein detects transmitted light not absorbed by the sample. In embodiments, the device is configured to determine the cell morphology (e.g., the cell boundary, granularity, or cell shape). For example, to determining the cell boundary includes comparing the pixel values of an image to a single intensity threshold, which may be determined quickly using histogram-based approaches as described in Carpenter, A. et al Genome Biology 7, R100 (2006) and Arce, S., Sci Rep 3, 2266 (2013)).

In embodiments, the device further includes at least one reservoir physically coupled to the structure. In embodiments, the at least one reservoir is fluidically coupled to the reagent aspiration manifold and/or the reagent dispense manifold. In embodiments, the reservoir is configured to store one or more reagents or hold waste material. In some embodiments, the reagents include fluids such as water, buffer solution, target capture reagents, or nucleic acid amplification reagents. In some embodiments, the reagent container compartments may be configured to maintain the contents of such containers at prescribed storage temperatures and/or to agitate such containers to maintain the contents of the containers in solution or suspension. In embodiments, the at least one reservoir includes reaction reagents, for example nucleic acid amplification reagents (e.g., polymerase and nucleotides needed for amplification), and/or nucleic acid sequencing reagents. In embodiments, the at least one reservoir includes at least one of a waste reservoir, a sequencing reagent reservoir, a clustering reagent reservoir, and a wash solution reservoir. In embodiments, the device includes a plurality of a sequencing reagent reservoirs and clustering reagent reservoirs. In embodiments, the clustering reagent reservoir includes amplification reagents (e.g., an aqueous buffer containing enzymes, salts, and nucleotides, denaturants, crowding agents, etc.)

In embodiments, the reservoirs include sequencing reagents (such as an aqueous buffer containing enzymes, salts, and nucleotides); a wash solution (an aqueous buffer); a cleave solution (an aqueous buffer containing a cleaving agent, such as a reducing agent); or a cleaning solution (a dilute bleach solution, dilute NaOH solution, dilute HCl solution, dilute antibacterial solution, or water). The fluid of the reservoirs can vary. The fluid can be, for example, an aqueous solution which may contain buffers (e.g., saline-sodium citrate (SSC), tris(hydroxymethyl)aminomethane or "Tris"), aqueous salts (e.g., KCl or $(NH_4)_2SO_4$)), nucleotides, polymerases, cleaving agent (e.g., tri-n-butyl-phosphine, triphenyl phosphine and its sulfonated versions (i.e., tris(3-sulfophenyl)-phosphine, TPPTS), and tri(carboxyethyl)phosphine (TCEP) and its salts, cleaving agent scavenger compounds (e.g., 2'-Dithiobisethanamine or 11-Azido-3,6,9-trioxaundecane-1-amine), chelating agents (e.g., EDTA), detergents, surfactants, crowding agents, or stabilizers (e.g., PEG, Tween, BSA). Non-limited examples of reservoirs include cartridges, pouches, vials, containers, and eppendorf tubes.

In embodiments, the device is configured to effectuate temperature cycling of the microplate. In embodiments, the device is configured to maintain a microplate at a preferred or any elevated temperature for a specified duration of time. Nucleic acid sequencing, in particular enzymatically catalyzed sequencing, is highly temperature dependent. Often suitable reaction temperatures to enable efficient sequencing are between 55° C. and 75° C. In embodiments, the device is configured to hold one or more reaction chambers (e.g., wells) in an environment that is maintained at higher than ambient temperatures so as to raise the temperature of the contents within each of the chambers. In embodiments, the device is configured to hold all of the wells in an environment that is maintained at higher than ambient temperatures so as to raise the temperature of the contents within each of the wells. In embodiments, the device is configured to hold one or more reaction chambers (e.g., wells) in an environment that is maintained at lower than ambient temperatures so as to lower the temperature of the contents within each of the chambers. In embodiments, the device is configured to hold all of the wells in an environment that is maintained at lower than ambient temperatures so as to lower the temperature of the contents within each of the wells. In embodiments, the device is configured to cycle between higher and lower temperatures. In embodiments, the device is configured to cycle between about 100° C. and about 20° C. In embodiments, the device is configured to cycle between about 70° C. and about 20° C. In embodiments, the device is configured to cycle between about 60° C. and about 40° C. In embodiments, the device is configured cool the microplate. For example, the device may include one or more cooling regions to reduce the temperature of the microplate. In embodiments, the device is configured cool the microplate by contacting the microplate with air at a lower temperature, wherein the temperature of the air is reduced relative to the temperature of the microplate. Thermoelectric coolers are available and can generally be configured to apply temperature control to a wide variety of different structures and materials. Temperature controllers may include any of a variety of different temperature control systems, including simple heaters and coolers, fans or radiators, integrated within the device. Temperature control systems are typically included along with temperature sensing systems for monitoring the temperature of the device or select regions of the device, e.g., the microplate and/or the microplate receiver, so as to provide feedback control to the overall temperature control system.

In embodiments, the device includes one or more heating elements positioned proximal to the microplate. In embodiments, the device includes one or more heating elements positioned proximal to the microplate receiver. In embodiments, the microplate receiver is in thermal contact with the heating elements. It is understood that for something to be in thermal contact it does not necessarily need to be in physical contact (e.g., radiative thermal transfer). As used herein, the term "heating element" and "temperature regulation apparatus" may include any known heating element for heating and cooling applications. In one embodiment, the heating element is a resistive heating element, such as a thin metal film. The heating element can also be provided as a molded or machined insert. Alternatively, in embodiments, the heating element is a thermoelectric device, such as a "Peltier device," which is generally constructed from electron-doped n-p semiconductor pairs that act as heat pumps. When current is applied to the semiconductor pairs, a temperature difference is established, where one side becomes hot and the other cold. If the current direction is reversed, the hot and cold faces is reversed. Typically, an electrically nonconductive material layer, such as aluminum nitride or polyimide, is disposed over the substrate faces of the thermoelectric modules so as to allow for proper isolation of the semiconductor element arrays. The heating element may be a resistive heater, inductive heater, peltier/thermoelectric, or radiative heater (e.g., infrared heater). The heating element may be comprised of any suitable material. For example, the heating element may include metals, such as nichrome, kanthal, cupronickel, and the like. In embodiments, the heating element includes a ceramic material (e.g., molybdenum disilicide, silicon carbine, barium titanate, lead titanate, or quartz). The heating element may include PTC rubber (i.e., polydimethylsiloxane (PDMS) loaded with carbon nanoparticles). The heating element may be a resistive heater comprised of any suitable material. The heating element may include an etched resistive metal film (e.g., an etched nichrome resistive metal film). The heating element may include a resistance heating alloy wire. The heating element may include additional insulating elements. The heating element may include an etched nichrome resistive metal film with Kapton insulation. Proper temperature control is maintained by ensuring suitable thermal contact with the microplate, and positioning the heating elements to minimize systematic biases due to heating gradients. Microplates may experience different temperatures depending on their proximity to heating elements. This temperature differential may perturb the assay readout (e.g., alter cell growth, denature, or enhance enzymes). A bias that shifts upon microplate rotation (compare left and right panels) or re-orientation is suggestive of an incubation-based systematic error.

Controlling the temperature may be carried out by a variety of means. For example, in embodiments, the temperature regulation apparatus is a thermoelectric temperature controller, e.g., a Peltier heater/cooler. Alternatively, the temperature regulation apparatus may incorporate a series of channels through which is flowed a recirculating temperature controlled fluid, e.g., water, ethylene glycol or oil, which is heated or cooled to a desired temperature, e.g., in an attached water bath. By way of example, some sequencing by synthesis methods include various cycles of extension, ligation, cleavage, and/or hybridization in which it may be desired to cycle the temperature. Further, in some sequencing techniques, temperatures may range from about 0° C. to about 20° C., to a higher temperature ranging from about 50° C. to about 95° C. for denaturation and/or other reaction stages.

In embodiments, the tubes carrying the fluids may be heated. For example, the wall of the tube may be configured to insulate, be heated and/or configured to generate heat so as to heat fluid within the lumen of the tube. In this regard, the tube can be at least partially wrapped, coated, surrounded, or otherwise coupled with a material that generates heat or that is configured to generate heat such as when an electrical current is applied thereto. In an embodiment, the material comprises a heat shrink jacket provided around the tube. The composition of the fluidic tubes may be any suitable material provided it can withstand the temperature changes and is chemically resistant to the solution. In a non-limiting example, in the device, the heated tube is a hose made using polytetrafluoroethylene (PTFE), steel, with rubber hose as a base hose. The tubing is a perfluoroalkoxy alkanes (PFA) tube for chemical and heat resistance. The heating element is a metal foil encapsulated in Kapton and coiled around the tubing. The jacket is a heat shrink material. In embodiments, the heated tube is a hose that includes PTFE, steel, or rubber.

In embodiments, the device includes at least one manifold coupled to the structure.

In embodiments, the at least one manifold includes at least one of a reagent aspiration manifold and a reagent dispense manifold. In embodiments, the manifold includes one or more substance-transfer devices for transferring fluids, e.g., sample fluids, reagents, fluids, waste fluids, etc., to and from reaction chambers of the microplate and/or other containers or reservoirs. In some embodiments, the substance-transfer devices may include one or more robotic pipettors configured for controlled, automated movement and access to the reaction chambers, reservoirs holding reagents, and reservoirs holding samples. In some embodiments, the substance-transfer devices may also include fluid dispensers, for example, nozzles, disposed within other devices and connected by suitable connectors.

In embodiments, the reagent aspiration manifold and/or the reagent dispense manifold may be positioned above the microplate at an angle. The angle at which the reagent aspiration manifold and/or the reagent dispense manifold is positioned with respect to the microplate, for example, may be about or at least about 1°, 2°, 3°, 4, 5°, 6°, 7° 8°, 9°, 10°, 11°, 12°, 13°, 14°, 15°, 16°, 17°, 18°, 19°, 20°, 21°, 22°, 23°, 24°, 25°, 26°, 27°, 28°, 29°, 30°, 35°, 40°, 45°, 50°, or more. Optimization of the positioning of the reagent aspiration manifold and/or the reagent dispense manifold with respect to microplate can give rise to more uniform reagent distribution and less sample disturbance.

In embodiments, the device includes an integrated system of one or more interconnected chambers, ports, and channels in fluid communication and configured for carrying out an analytical reaction or process, either alone or in cooperation with an appliance or instrument that provides support functions. The device may be integrated in that the one or more interconnected chambers, ports, and channels may be contained or housed in a single housing or collection of housings mechanically attached to one another. The reagent aspiration manifold and/or the reagent dispense manifold are in fluidic communication with a fluidic system. The fluid system may store fluids for washing or cleaning the fluidic network of the device, and also for diluting the reactants. For example, the fluid system may include various reservoirs to store reagents, enzymes, other biomolecules, buffer solutions, aqueous, and non-polar solutions. Furthermore, the fluid system may also include waste reservoirs for receiving waste products. As used herein, fluids may be liquids, gels, gases, or a mixture of thereof. Also, a fluid can be a mixture of two or more fluids. The fluidic network may include a plurality of fluidic components (e.g., fluid lines, pumps, aspirators, nozzles, valves, or other fluidic devices, manifolds, reservoirs) configured to have one or more fluids flowing therethrough. In embodiments, the device includes one or more peristaltic pumps. In embodiments, the device includes one or more syringe pumps. Exemplary systems having fluidic components that can be readily modified for use in a system herein include, but are not limited to, those set forth in U.S. Pat. Nos. 8,241,573, 8,039,817; or US Pat. App. Pub. No. 2012/0270305 A1, each of which is incorporated herein by reference. In embodiments, the microfluidic device further includes one or more excitation lasers. In embodiments, the device includes straight cut dispensing tips. In embodiments, the microfluidic device is configured for generating and actuating (such as moving, merging, splitting, etc.) liquids and reagents via active or passive forces. Examples of active forces include, but are not limited to, electric field. Exemplary active force techniques include electrowetting, dielectrophoresis, opto-electrowetting, electrode-mediated, electric-field mediated, electrostatic actuation, and the like or a combination thereof.

In embodiments, the support functions include at least one of sample introduction, fluid and/or reagent driving means, temperature control, detection systems, data collection and integration systems, and are configured to determine the nucleic acid sequence of a template polynucleotide (e.g., a target polynucleotide, optionally comprising a barcode). The device can use pressure drive flow control, e.g., utilizing valves and pumps, to manipulate the flow of reagents, molecules, or enzymes in one or more directions and/or into one or more channels of a device.

In an aspect is provided a device, the device configured to perform at least: a) in situ single cell analysis; b) in situ tissue analysis; and c) sequencing (e.g., nucleic acid sequencing). In embodiments, sequencing includes at least one of RNA-sequencing and immune repertoire sequencing. In embodiments, sequencing includes RNA-sequencing and immune repertoire sequencing. In embodiments, the device includes a unitary structure. In embodiments, the unitary structure includes a base platform or a table. In embodiments, the device is capable of performing a) in situ single cell analysis; b) in situ tissue analysis; and c) sequencing (e.g., nucleic acid sequencing), and obtaining images of a sample.

In embodiments, the device is further configured to provide RNA transcription analysis (e.g., counting RNA) for targeted panels. In embodiments, the device is further configured to perform protein expression analysis (e.g., counting of proteins) for targeted panels. In embodiments, the device is further configured to perform sequencing of variable regions in immune cells (e.g., B-cells or T-cells) or cancer cells. In embodiments, the device includes at least one microplate. In embodiments, the microplate includes 6, 12, 24, 48, 96, 384 or 1536 sample wells.

In embodiments, the device includes a sample stage configured to be coupled to a microplate receiver. In embodiments, the device includes a microplate receiver configured to be coupled to a microplate (e.g., a microplate as described herein). In embodiments, the imaging system includes at least one of a kinematic mount and an auto leveler. In embodiments, the imaging system includes an autofocusing system.

In embodiments, the device is configured to dispense one or more reagents into only a fraction of the entire microplate. In embodiments, the device is configured to dispense one or more reagents into only 25% of the entire microplate. In embodiments, the device is configured to dispense one or more reagents into only 50% of the entire microplate. In embodiments, the device is configured to dispense one or more reagents into only 75% of the entire microplate.

In embodiments, the device is configured to dispense one or more wash reagents into only a fraction of the entire microplate. In embodiments, the device is configured to dispense one or more wash reagents into only 25% of the entire microplate. In embodiments, the device is configured to dispense one or more wash reagents into only 50% of the entire microplate. In embodiments, the device is configured to dispense one or more wash reagents into only 75% of the entire microplate. In embodiments, the device is configured to dispense wash reagents in parallel to all or a fraction of the reaction chambers of the microplate.

In embodiments, the device includes an imaging system. In embodiments, the imaging system includes at least one of a three-dimensional imager, a TDI scanner, a laser, a camera, an autofocus, and a transilluminator. In embodiments, the device includes at least one structure configured to enclose a region and control temperature within the region. In embodiments, the device is configured to perform temperature cycling of a microplate. In embodiments, the device includes at least one of a waste reservoir, a sequencing reagent reservoir, a clustering reagent reservoir, and a wash solution reservoir. In embodiments, the device includes a reagent aspiration manifold. In embodiments, the device includes a reagent dispense manifold. In embodiments, the device includes both a reagent aspiration manifold and a reagent dispense manifold.

In embodiments, the device images an area less than about 1 μm in xy plane; and less than about 2 μm in z direction (i.e., orthogonal to the xy plane). In embodiments, the device images an area less than about 1 μm in xy plane; and about 1-20 μm in z direction (i.e., orthogonal to the xy plane). A plane refers to a 2-dimensional (2D) area defined by two axes (e.g., x and y together form the xy plane). When used in reference to a detecting apparatus and an object observed by the detector, the xy plane may be specified as being orthogonal to the direction of observation between the detector and object being detected. The image plane is a projection of the image on a two-dimensional plane. For example, in embodiments, the image plane is the projection of an image on the surface of the image sensor.

In embodiments, the device is configured to perform fluorescent imaging. In embodiments, the device includes one or more light sources (e.g., one or more lasers). In embodiments, the illuminator or light source is a radiation source (i.e., an origin or generator of propagated electromagnetic energy) providing incident light to the sample. A radiation source can include an illumination source producing electromagnetic radiation in the ultraviolet (UV) range (about 200 to 390 nm), visible (VIS) range (about 390 to 770 nm), or infrared (IR) range (about 0.77 to 25 microns), or other range of the electromagnetic spectrum. In embodiments, the illuminator or light source is a lamp such as an arc lamp or quartz halogen lamp. In embodiments, the illuminator or light source is a coherent light source. In embodiments, the light source is a laser, LED (light emitting diode), a mercury or tungsten lamp, or a super-continuous diode. In embodiments, the light source provides excitation beams having a wavelength between 200 nm to 1500 nm. In embodiments, the laser provides excitation beams having a wavelength of 405 nm, 470 nm, 488 nm, 514 nm, 520 nm, 532 nm, 561 nm, 633 nm, 639 nm, 640 nm, 800 nm, 808 nm, 912 nm, 1024 nm, or 1500 nm. In embodiments, the laser provides excitation beams having a wavelength of 405 nm, 488 nm, 532 nm, or 633 nm.

In embodiments, the light source provides one or more excitation beams. An excitation beam is intended to mean electromagnetic energy propagated toward a sample or sample region. An excitation beam may be shaped such that the collection of electromagnetic waves or particles are propagated in a uniform direction, wherein the 2-dimensional cross section orthogonal to the direction of propagation is rectangular or oblong. Exemplary 2-dimensional cross sections of an excitation beam can include a rectangular, elliptical, or oval shape. The cross-sectional width of an excitation beam can have one or both dimensions in a range of, for example, about 0.5 µm to about 50 µm. For example, a dimension of the excitation beam can be at least about 0.05 µm, 0.1 µm, 0.5 µm, 1 µm, 5 µm or 10 µm. Furthermore, a dimension of an excitation beam can be, for example, at most about 0.1 µm, 0.2 µm, 0.5 µm, 1 µm, 5 µm or 10 µm. In embodiments, a dimension of an excitation beam is about 0.2 µm to about 50 µm. In embodiments, a dimension of a excitation beam is 10 µm to about 30 µm. In embodiments, a dimension of an excitation beam is 20 µm to about 30 µm. In embodiments, a dimension of an excitation beam is 20 µm. It will be understood that these dimensions are merely exemplary and excitation beams having other dimensions can be used if desired.

In embodiments, the light source is a laser (e.g., a laser such as a solid state laser or a gas laser). In embodiments, the light source includes one or more vertical cavity surface emitting lasers (VCSELs), vertical external cavity surface emitting lasers (VECSELs), or diode pumped solid state (DPSS) lasers. In embodiments, the light source is a continuous wave (CW) laser or a pulsed laser. In embodiments, the light source is a pulsed laser. In embodiments, the light source is an ultrashort pulsed laser. An ultrashort laser is a laser capable of producing excitation beams for a time duration of a picosecond or less. An ultrashort laser typically includes additional components, such as a pulse controller, pulse shaper, and spatial light modulator, and the like for controlling the pulse of excitation beams. In embodiments, the ultrashort laser provides excitation beams for femtoseconds or picoseconds. In embodiments, the light source is a pulsed femtosecond or picosecond laser. In embodiments, the laser is a Ti-sapphire laser, a dye-laser, or a fiber laser. In embodiments, the system includes two or more light sources (e.g., lasers). In embodiments, the first light source configured to emit light in red wavelengths, and a second light source configured to emit light in green wavelengths. In embodiments, the device includes two or more lasers.

In embodiments, the device includes one or more sensor arrays. In embodiments, each sensor array is a TDI sensor array. A sensor array refers to a device or apparatus having a plurality of elements that convert the energy of contacted photons into an electrical response. The term "time delay integration" or "TDI" refers to sequential detection of different portions of a sample by different subsets of elements of a detector array, wherein transfer of charge between the subsets of elements proceeds at a rate synchronized with and in the same direction as the apparent motion of the sample being imaged. For example, TDI can be carried out by scanning a sample such that a frame transfer device produces a continuous video image of the sample by means of a stack of linear arrays aligned with and synchronized to the apparent movement of the sample, whereby as the image moves from one line to the next, the stored charge moves along with it. Accumulation of charge can integrate during the entire time required for the row of charge to move from one end of the detector to the serial register. In embodiments, the sensor array (e.g., TDI sensor array) can be configured for binning. Binning increases the detector array's sensitivity by summing the charges from multiple pixels in the array into one pixel. Exemplary types of binning that can be used include horizontal binning, vertical binning, or full binning. With horizontal binning, pairs of adjacent pixels in each line of a detector array are summed. With vertical binning, pairs of adjacent pixels from two lines in the array are summed. Full binning is a combination of horizontal and vertical binning in which four adjacent pixels are summed.

In embodiments, each sensor array is at least 2,000 pixels wide. In embodiments, each sensor array is at least 4,000 pixels wide. In embodiments, each sensor array is at least 8,000 pixels wide. In embodiments, each sensor array is at least 12,000 pixels wide. In embodiments, each sensor array is at least 16,000 pixels wide. In embodiments, each sensor array is at least 16 pixels long. In embodiments, each sensor array is at least 32 pixels long. In embodiments, each sensor array is at least 64 pixels long. In embodiments, each sensor array is at least 128 pixels long. In embodiments, each sensor array is at least 256 pixels long. In embodiments, each sensor array is at least 8,000 pixels wide and at least 64 pixels long. In embodiments, each sensor array is at least 8,000 pixels wide and at least 128 pixels long. In embodiments, each sensor array is at least 8,000 pixels wide and at least 256 pixels long.

In embodiments, the device further includes a display and a graphical user interface. Suitable displays include liquid crystal displays (LCD), thin film transistor liquid crystal displays (TFT-LCD), organic light emitting diode (OLED) displays (including passive-matrix OLED (PMOLED) and active-matrix OLED (AMOLED) displays), plasma displays, video projectors, and head-mounted displays (such as a VR headset) in communication with the device.

The devices described herein are implemented via control and computing hardware components, user-created software, data input components, and data output components. Computing hardware components include computing and control modules (e.g., system controller(s)), such as microprocessors and computers, configured to control steps by receiving one or more input values, executing one or more algorithms stored on non-transitory machine-readable media (e.g., software) that provide instruction for manipulating or otherwise acting on the input values, and output one or more output values. Such outputs may be displayed or otherwise indicated to an operator for providing information to the operator, e.g., information as to the status of the device or a process being performed by such a device, or such outputs may comprise inputs to other processes and/or control algorithms. Data input components include elements by which data is input for use by the control and computing hardware components, e.g., positions sensors, such as graphic user interfaces, keyboards, touch screens, microphones, barcode scanners, or switches. Data output components may include hard drives or other storage media, graphic user interfaces, monitors, printers, indicator lights, or audible signal elements (e.g., buzzer, horn, or bell). The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), the Internet, WiFi (IEEE 802.11 standards), NFC, BLU- ETOOTH®, ZIGBEE, and the like. In embodiments, the device or system also may include integrated control software or firmware for instructing the operation of the various components of the system, typically programmed into a connected processor, which may be integrated into the instrument itself, or maintained on a directly or wirelessly connected, but separate processor, e.g., a computer, tablet, smartphone, or the like, for controlling the operation of, and/or for obtaining data from the various subsystems and/or components of the overall system.

Certain processes and actions such as "detecting," "receiving," "quantifying," "measuring", "mapping," "generating," "registering," "determining," "processing," "computing," "estimating," "calculating," and the like may refer to the actions and processes of a computer system, or similar electronic computing device, that manipulates and transforms data represented as physical (e.g., electronic) quantities within the computer system's components and memories or other such information storage. Embodiments of the methods described herein may be implemented using computer software. If written in a programming language conforming to a recognized standard, sequences of instructions designed to implement the methods may be compiled for execution on a variety of hardware platforms and for interface to a variety of operating systems. In some embodiments, the disclosed methods may be implemented using software applications that are stored in a memory and executed by a processor (e.g., CPU) provided on the system. In some embodiments, the disclosed methods may be implanted using software applications that are stored in memories and executed by CPUs distributed across the system. As such, the modules of the system may be a general purpose computer system that becomes a specific purpose computer system when executing the routine of the disclosure. The modules of the system may also include an operating system and micro instruction code. The various processes and functions described herein may either be part of the micro instruction code or part of the application program or routine (or combination thereof) that is executed via the operating system. In embodiments, the device includes a storage and/or memory device. The storage and/or memory device is one or more physical apparatuses used to store data or programs on a temporary or permanent basis. In embodiments, the device is volatile memory and requires power to maintain stored information. In some cases, the device is non-volatile memory and retains stored information when the digital processing device is not powered. The non-volatile memory may comprise flash memory, dynamic random-access memory (DRAM), ferroelectric random access memory (FRAM), phase-change random access memory (PRAM), or the like. In other cases, the device is a storage device including, by way of non-limiting examples, CD-ROMs, DVDs, flash memory devices, magnetic disk drives, magnetic tapes drives, optical disk drives, cloud computing-based storage, and the like. In various cases, the storage and/or memory device is a combination of devices such as those disclosed herein.

In an aspect is provided a device (e.g., a device as described herein), including a microplate receiver configured to be coupled to a microplate; a microplate including one or more wells; at least one heating element thermally coupled to the microplate receiver; a fluidics dispenser configured to dispense one or more reagents into the microplate; and an imaging system configured to detect one or more features in the microplate; and a structure physically coupled to the sample stage, the heating element, the fluidics dispenser, and the imaging system. In embodiments, the microplate includes a plurality of wells, wherein one or more wells include a tissue section. In embodiments, the tissue is immobilized to the well of the microplate by covalently binding the tissue to the well. In embodiments, the tissue is immobilized to the receiving substrate by non-covalently binding the tissue to well. For non-covalent binding, the tissue sections attach to the well surface due to surface interactions, such as Van der Waal forces, electrostatic forces, hydrophobic interactions and hydrogen bonds.

In embodiments, the tissue section may be referred to herein as a biological sample. In embodiments, the thickness of the biological sample is about 1 μm to about 20 μm. In embodiments, the thickness of the biological sample is about 5 μm to about 12 μm. In embodiments, the thickness of the biological sample is about 8 μm to about 15 μm. In embodiments, the thickness of the biological sample is about 1 μm, about 2 μm, about 3 μm, about 4 μm, about 5 μm, about 6 μm, about 7 μm, about 8 μm, about 9 μm, about 10 μm, about 11 μm, about 12 μm, about 13 μm, about 14 μm, or about 15 μm. In embodiments, the thickness of the biological sample is about 1 μm. In embodiments, the thickness of the biological sample is about 2 μm. In embodiments, the thickness of the biological sample is about 3 μm. In embodiments, the thickness of the biological sample is about 4 μm. In embodiments, the thickness of the biological sample is about 5 μm. In embodiments, the thickness of the biological sample is about 6 μm. In embodiments, the thickness of the biological sample is about 7 μm. In embodiments, the thickness of the biological sample is about 8 μm. In embodiments, the thickness of the biological sample is about 9 μm. In embodiments, the thickness of the biological sample is about 10 μm. In embodiments, the thickness of the biological sample is about 11 μm. In embodiments, the thickness of the biological sample is about 12 μm. In embodiments, the thickness of the biological sample is about 13 μm. In embodiments, the thickness of the biological sample is about 14 μm. In embodiments, the thickness of the biological sample is about 15 μm. In particular embodiments, a tissue section has a size greater than sections typically examined by traditional pathology thin section or immunohistochemical analysis, which are typically in the range of 4-10 microns thick. In certain embodiments, a tissue section is greater than 20 microns, greater than 50 microns, greater than 100 microns, greater than 200 microns, greater than 500 microns, greater than 1 mm, greater than 2 mm, greater than 5 mm, greater than 10 mm or greater than 20 mm in thickness and/or length. In particular embodiments, the tissue section has a length and/or a thickness between 20 microns and 20 mm, between 20 microns and 10 mm, or between 50 microns and 1 mm. In certain embodiments, a tissue section is a cubic sample with each side greater than 10 microns, greater than 20 microns, greater than 50 microns, greater than 100 microns, greater than 200 microns, greater than 500 microns, greater than 1 mm, greater than 2 mm, greater than 5 mm, greater than 10 mm, or greater than 2 mm in thickness and/or length. In some embodiments, a tissue section is thinner, e.g., from about 4-10 or 4-20 microns in thickness. The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 micrometers thick. Multiple tissue sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analyzed successively to derive three-dimensional information about the biological sample.

In embodiments, the tissue section includes a tissue or a cell (e.g., a plurality of cells such as blood cells). In embodiments, the tissue section includes one or more cells. In embodiments, the tissue section is embedded in an embedding material including paraffin wax, polyepoxide polymer, polyacrylic polymer, agar, gelatin, celloidin, cryogel, optimal cutting temperature (OCT) compositions, glycols, or a combination thereof. In embodiments, the tissue section is embedded in an embedding material including paraffin wax. In embodiments, the tissue section is embedded in an embedding material including a polyepoxide polymer. In embodiments, the tissue section is embedded in an embedding material including polyacrylic polymer. In embodiments, the tissue section is embedded in an embedding material including agar. In embodiments, the tissue section is embedded in an embedding material including gelatin. In embodiments, the tissue section is embedded in an embedding material including celloidin. In embodiments, the tissue section is embedded in an embedding material including a cryogel. In embodiments, the tissue section is embedded in an embedding material including an optimal cutting temperature (OCT) compositions. In embodiments, the tissue section is embedded in an embedding material including one or more glycols. Tissue sections may be obtained from a subject by any means known and available in the art. In particular embodiments, a tissue section, e.g., a tumor tissue sample, is obtained from a subject by fine needle aspiration, core needle biopsy, stereotactic core needle biopsy, vacuum-assisted core biopsy, or surgical biopsy. In particular embodiments, the surgical biopsy is an incisional biopsy, which removes only part of the suspicious area.

In embodiments, the tissue section includes a tissue or a cell. Biological tissue samples suitable for use with the methods and systems described herein generally include any type of tissue samples collected from living or dead subjects, such as, for example, tumor tissue and autopsy samples. Tissue samples may be collected and processed using the methods and systems described herein and subjected to microscopic analysis immediately following processing, or may be preserved and subjected to microscopic analysis at a future time, e.g., after storage for an extended period of time. In some embodiments, the methods described herein may be used to preserve tissue samples in a stable, accessible and fully intact form for future analysis. For example, tissue samples, such as, e.g., human tumor tissue samples, may be processed as described herein and cleared to remove a plurality of cellular components, such as, e.g., lipids, and then stored for future analysis. In some embodiments, the methods and systems described herein may be used to analyze a fresh tissue section. In some embodiments, the methods and systems described herein may be used to analyze a previously-preserved (e.g., previously fixed) or stored tissue section (e.g., tissue sample). For example, in some embodiments a previously-preserved tissue sample that has not been subjected to a sample preparation process described herein may be processed and analyzed as described herein. In particular methods, a tissue sample is frozen prior to being processed as described herein. In some embodiments, the biological sample is a tissue section. In some embodiments, the sample is a fixed and/or stained biological sample (e.g., a fixed and/or stained tissue section).

Non-limiting examples of stains include histological stains (e.g., hematoxylin and/or eosin) and immunological stains (e.g., fluorescent stains).

In certain embodiments, tissue sections are tumor tissue samples. Tumor samples may contain only tumor cells, or they may contain both tumor cells and non-tumor cells. In particular embodiments, a tissue section comprises only non-tumor cells. In particular embodiments, the tumor is a solid tumor. In particular embodiments, the tissue section is obtained from or comprises an adrenal cortical cancer, anal cancer, aplastic anemia, bileduct cancer, bladder cancer, bone cancer, bone metastasis, brain tumor, brain cancer, breast cancer, childhood cancer, cancer of unknown primary origin, Castleman disease, cervical cancer, colon/rectal cancer, endometrial cancer, esophagus cancer, Ewing family of tumors, eye cancer, gallbladder cancer, gastrointestinal carcinoid tumors, gastrointestinal stromal tumors, gestational trophoblastic disease, head or neck cancer, Kaposi sarcoma, renal cell carcinoma, laryngeal and hypopharyngeal cancer, liver cancer, non-small cell lung cancer, small cell lung cancer, lung carcinoid tumor, lymphoma of the skin, malignant mesothelioma, myelodysplasia syndrome, nasal cavity or paranasal sinus cancer, nasopharyngeal cancer, neuroblastoma, oral cavity or oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma in adult soft tissue, basal or squamous cell skin cancer, melanoma, small intestine cancer, stomach cancer, testicular cancer, throat cancer, thymus cancer, thyroid cancer, uterine sarcoma, vaginal cancer, vulvar cancer, Waldenstrom macroglobulinemia, Wilms tumor and secondary cancers caused by cancer treatment, is a tissue section obtained from a subject diagnosed with or suspected of having any of these tumors or cancers.

In embodiments, the tissue section includes one or more detection agents. In embodiments, the tissue section includes one or more barcodes. In embodiments, the detection agent includes a label. In embodiments, the detection agent includes a fluorescent label. In embodiments, the detection agent includes an oligonucleotide barcode (e.g., a 5 to 15 nucleotide sequence). In embodiments, the oligonucleotide barcode includes at least two primer binding sequences. In embodiments, the oligonucleotide barcode includes an amplification primer binding sequence. In embodiments, the oligonucleotide barcode includes a sequencing primer binding sequence. The amplification primer binding sequence refers to a nucleotide sequence that is complementary to a primer useful in initiating amplification (i.e., an amplification primer). Likewise, a sequencing primer binding sequence is a nucleotide sequence that is complementary to a primer useful in initiating sequencing (i.e., a sequencing primer). Primer binding sequences usually have a length in the range of between 3 to 36 nucleotides, also 5 to 24 nucleotides, also from 14 to 36 nucleotides. In embodiments, an amplification primer and a sequencing primer are complementary to the same primer binding sequence, or overlapping primer binding sequences. In embodiments, an amplification primer and a sequencing primer are complementary to different primer binding sequences. In embodiments, the primer binding sequence is complementary to a fluorescent in situ hybridization (FISH) probe. FISH probes may be custom designed using known techniques in the art, see for example Gelali, E., et al. Nat Commun 10, 1636 (2019). In embodiments, the detection agent includes a padlock probe. Padlock probes are specialized ligation probes, examples of which are known in the art, see for example Nilsson M, et al. *Science*. 1994; 265(5181):2085-2088), and has been applied to detect transcribed RNA in cells, see for example Christian A T, et al. Proc Natl Acad Sci USA. 2001; 98(25):14238-14243, both of which are incorporated herein by reference in their entireties. In embodiments, the padlock probe is approximately 50 to 200 nucleotides. In embodiments, a padlock probe has a first domain that is capable of hybridizing to a first target sequence domain, and a second ligation domain, capable of hybridizing to an adjacent second sequence domain. The configuration of the padlock probe is such that upon ligation of the first and second ligation domains of the padlock probe, the probe forms a circular polynucleotide, and forms a complex with the sequence (i.e., the sequence it hybridized to, the target sequence) wherein the target sequence is "inserted" into the loop of the circle. Padlock probes are useful for the methods provided herein and include, for example, padlock probes for genomic analyses, as exemplified by Gore, A. et al. Nature 471, 63-67 (2011); Porreca, G. J. et al. Nat Methods 4, 931-936 (2007); Li, J. B. et al. Genome Res 19, 1606-1615 (2009), Zhang, K. et al. Nat Methods 6, 613-618 (2009); Noggle, S. et al. Nature 478, 70-75 (2011); and Li, J. B. et al. Science 324, 1210-1213 (2009), the content of each of which is incorporated by reference in its entirety.

In embodiments, the detection agent includes a protein-specific binding agent. In embodiments, the detection agent includes a protein-specific binding agent bound to a nucleic acid sequence, bioconjugate reactive moiety, an enzyme, or a label. In embodiments, the protein-specific binding agent is an antibody, single-chain Fv fragment (scFv), antibody fragment-antigen binding (Fab), affimer, or an aptamer.

In embodiments, the systems, devices, methods, and compositions can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual well of the substrate.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above.

III. Kits

In an aspect is provided a kit. In embodiments, the kit is to support analysis of single cells and tissue sections on the device described herein. In embodiments, the kits enable multiomics analysis, including RNA transcription, protein expression, and targeted gene sequencing. In embodiments, the kits include specialized well-plates, and reagents for sample preparation, and sequencing readout. In embodiments, the kits for protein detection include DNA-conjugated antibodies.

In an aspect is provided a kit, including the plurality of particles, adapters, primers, and enzymes as described herein. Generally, the kit includes one or more containers providing a composition and one or more additional reagents (e.g., a buffer suitable for polynucleotide extension and/or sequencing.

In embodiments, amplification reagents and other reagents may be provided in lyophilized form. In embodiments, amplification reagents and other reagents may be provided in a container that includes wells within which the lyophilized reagent may be reconstituted.

In embodiments the kits are for use in accordance with any of the devices, systems, or methods disclosed herein, and including one or more elements thereof. In embodiments, a kit includes labeled nucleotides including differently labeled nucleotides, enzymes, buffers, oligonucleotides, and related solvents and solutions. In embodiments, the kit includes an oligonucleotide primer (e.g., an oligonucleotide primer as described herein). The kit may also include a template nucleic acid (DNA and/or RNA), one or more primer polynucleotides, nucleoside triphosphates (including, e.g., deoxyribonucleotides, dideoxynucleotides, ribonucleotides, labeled nucleotides, and/or modified nucleotides), buffers, salts, and/or labels (e.g., fluorophores). In embodiments, the kit includes components useful for circularizing template polynucleotides using a ligation enzyme (e.g., CircligaseTM enzyme, Taq DNA Ligase, HiFi Taq DNA Ligase, T4 ligase, or Ampligase DNA Ligase). For example, such a kit further includes the following components: (a) reaction buffer for controlling pH and providing an optimized salt composition for a ligation enzyme (e.g., CircligaseTM enzyme, Taq DNA Ligase, HiFi Taq DNA Ligase, T4 ligase, or Ampligase DNA Ligase), and (b) ligation enzyme cofactors. In embodiments, the kit further includes instructions for use thereof. In embodiments, kits described herein include a polymerase. In embodiments, the polymerase is a DNA polymerase. In embodiments, the DNA polymerase is a thermophilic nucleic acid polymerase. In embodiments, the DNA polymerase is a modified archaeal DNA polymerase. In embodiments, the kit includes a sequencing solution. In embodiments, the sequencing solution include labeled nucleotides including differently labeled nucleotides, wherein the label (or lack thereof) identifies the type of nucleotide. For example, each adenine nucleotide, or analog thereof; a thymine nucleotide; a cytosine nucleotide, or analog thereof; and a guanine nucleotide, or analog thereof may be labeled with a different fluorescent label. In embodiments, the kit includes a modified terminal deoxynucleotidyl transferase (TdT) enzyme. CircLigase is a trademark of EpiCentre Technologies Corp.

In embodiments, the kit includes a sequencing polymerase, and one or more amplification polymerases. In embodiments, the sequencing polymerase is capable of incorporating modified nucleotides. In embodiments, the polymerase is a DNA polymerase. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol µ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g., Therminator™ γ, 9° N polymerase (exo–), Therminator™ II, Therminator™ III, or Therminator™ IX). In embodiments, the DNA polymerase is a thermophilic nucleic acid polymerase. In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044, each of which are incorporated herein by reference for all purposes). In embodiments, the kit includes a strand-displacing polymerase. In embodiments, the kit includes a strand-displacing polymerase, such as a phi29 polymerase, phi29 mutant polymerase or a thermostable phi29 mutant polymerase.

In embodiments, the kit includes a buffered solution. Typically, the buffered solutions contemplated herein are made from a weak acid and its conjugate base or a weak base and its conjugate acid. For example, sodium acetate and acetic acid are buffer agents that can be used to form an acetate buffer. Other examples of buffer agents that can be used to make buffered solutions include, but are not limited to, Tris, bicine, tricine, HEPES, TES, MOPS, MOPSO and PIPES. Additionally, other buffer agents that can be used in enzyme reactions, hybridization reactions, and detection reactions are known in the art. In embodiments, the buffered solution can include Tris. With respect to the embodiments described herein, the pH of the buffered solution can be modulated to permit any of the described reactions. In some embodiments, the buffered solution can have a pH greater than pH 7.0, greater than pH 7.5, greater than pH 8.0, greater than pH 8.5, greater than pH 9.0, greater than pH 9.5, greater than pH 10, greater than pH 10.5, greater than pH 11.0, or greater than pH 11.5. In other embodiments, the buffered solution can have a pH ranging, for example, from about pH 6 to about pH 9, from about pH 8 to about pH 10, or from about pH 7 to about pH 9. In embodiments, the buffered solution can comprise one or more divalent cations. Examples of divalent cations can include, but are not limited to, $Mg^{2+}$, $Mn^{2+}$, $Zn^{2+}$, and $Ca^{2+}$. In embodiments, the buffered solution can contain one or more divalent cations at a concentration sufficient to permit hybridization of a nucleic acid. In embodiments, the buffered solution can contain one or more divalent cations at a concentration sufficient to permit hybridization of a nucleic acid. In embodiments, the buffered solution includes about 10 mM Tris, about 20 mM Tris, about 30 mM Tris, about 40 mM Tris, or about 50 mM Tris. In embodiments the buffered solution includes about 50 mM NaCl, about 75 mM NaCl, about 100 mM NaCl, about 125 mM NaCl, about 150 mM NaCl, about 200 mM NaCl, about 300 mM NaCl, about 400 mM NaCl, or about 500 mM NaCl. In embodiments, the buffered solution includes about 0.05 mM EDTA, about 0.1 mM EDTA, about 0.25 mM EDTA, about 0.5 mM EDTA, about 1.0 mM EDTA, about 1.5 mM EDTA or about 2.0 mM EDTA. In embodiments, the buffered solution includes about 0.01% Triton® X-100, about 0.025% Triton® X-100, about 0.05% Triton® X-100, about 0.1% Triton® X-100, or about 0.5% Triton® X-100. In embodiments, the buffered solution includes 20 mM Tris pH 8.0, 100 mM NaCl, 0.1 mM EDTA, 0.025% Triton® X-100. In embodiments, the buffered solution includes 20 mM Tris pH 8.0, 150 mM NaCl, 0.1 mM EDTA, 0.025% Triton® X-100. In embodiments, the buffered solution includes 20 mM Tris pH 8.0, 300 mM NaCl, 0.1 mM EDTA, 0.025% Triton® X-100. In embodiments, the buffered solution includes 20 mM Tris pH 8.0, 400 mM NaCl, 0.1 mM EDTA, 0.025% Triton® X-100.

In embodiments, the buffered solution includes 20 mM Tris pH 8.0, 500 mM NaCl, 0.1 mM EDTA, 0.025% Triton® X-100.

In embodiments, the kit includes one or more sequencing reaction mixtures. In embodiments, the sequencing reaction mixture includes a buffer. In embodiments, the buffer includes an acetate buffer, 3-(N-morpholino)propanesulfonic acid (MOPS) buffer, N-(2-Acetamido)-2-aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl-1-propanol (AMP) buffer, 4-(Cyclohexylamino)-1-butanesulfonic acid (CABS) buffer, glycine-NaOH buffer, N-Cyclohexyl-2-aminoethanesulfonic acid (CHES) buffer, tris(hydroxymethyl)aminomethane (Tris) buffer, or a N-cyclohexyl-3-aminopropanesulfonic acid (CAPS) buffer. In embodiments, the buffer is a borate buffer. In embodiments, the buffer is a CHES buffer. In embodiments, the sequencing reaction mixture includes nucleotides, wherein the nucleotides include a reversible terminating moiety and a label covalently linked to the nucleotide via a cleavable linker. In embodiments, the sequencing reaction mixture includes a buffer, DNA polymerase, detergent (e.g., Triton® X), a chelator (e.g., EDTA), and/or salts (e.g., ammonium sulfate, magnesium chloride, sodium chloride, or potassium chloride).

The term "kit" includes both fragmented and combined kits. In embodiments, the kit includes, without limitation, nucleic acid primers, probes, adapters, enzymes, and the like, and are each packaged in a container, such as, without limitation, a vial, tube or bottle, in a package suitable for commercial distribution, such as, without limitation, a box, a sealed pouch, a blister pack and a carton. The package typically contains a label or packaging insert indicating the uses of the packaged materials. As used herein, "packaging materials" includes any article used in the packaging for distribution of reagents in a kit, including without limitation containers, vials, tubes, bottles, pouches, blister packaging, labels, tags, instruction sheets and package inserts.

Adapters and/or primers may be supplied in the kits ready for use, as concentrates-requiring dilution before use, or in a lyophilized or dried form requiring reconstitution prior to use. If required, the kits may further include a supply of a suitable diluent for dilution or reconstitution of the primers and/or adapters. Optionally, the kits may further include supplies of reagents, buffers, enzymes, and dNTPs for use in carrying out nucleic acid amplification and/or sequencing. Further components which may optionally be supplied in the kit include sequencing primers suitable for sequencing templates prepared using the methods described herein.

In embodiments, the kit can further include one or more biological stain(s) (e.g., any of the biological stains as described herein). For example, the kit can further include eosin and hematoxylin. In other examples, the kit can include a biological stain such as acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, safranin, or any combination thereof.

IV. Methods of Use

In an aspect is provided a method of profiling a sample (e.g., a cell). In embodiments, the method includes determining information (e.g., gene and protein expression) about the transcriptome of an organism thus elucidating subcellular substances and processes while gaining valuable spatial localization information within a cell. In embodiments, the method includes simultaneously sequencing a plurality of nucleic acids, such as RNA transcripts, in situ within an optically resolved volume of a sample (e.g., a voxel). RNA transcripts are responsible for the process of converting DNA into an organism's phenotype, thus by determining the types and quantity of RNA present in a sample (e.g., a cell), it is possible to assign a phenotype to the cell. RNA transcripts include coding RNA and non-coding RNA molecules, such as messenger RNA (mRNA), transfer RNA (tRNA), micro RNA (miRNA), small interfering RNA (siRNA), small nucleolar RNA (snoRNA), small nuclear RNA (snRNA), Piwi-interacting RNA (piRNA), enhancer RNA (eRNA), or ribosomal RNA (rRNA). In embodiments, the target is pre-mRNA. In embodiments, the target is heterogeneous nuclear RNA (hnRNA). In embodiments, the method includes, within one or more wells of a microplate, detecting a probe hybridized to a target of interest in a sample (e.g., a cell or a tissue).

In embodiments, the sample is a living cell, otherwise referred to herein as a live cell. In some embodiments, a live cell is immobilized to the microplate by contacting the live cell with a hydrogel. In embodiments, the method includes obtaining a plurality of images of the live cell and quantifying the mobility of the cell. In embodiments, the method includes monitoring over time the levels of an analyte within the cell. In embodiments, the method includes obtaining a plurality of images and aligning the images to provide a "movie-like" display of the desired structure with the motion. In embodiments, the device is configured for acquiring a sequence of images, and processing means for processing the sequence of images.

In an aspect is provided a method of imaging a plurality of cells within a well of a microplate, the method including: contacting the microplate with a sample including the plurality of cells and attaching the sample to the well; heating the microplate to at least 90° C. (e.g., 90° C., 95° C., 99° C., 100° C., 105° C., 110° C., 115° C., or about 120° C.); contacting the sample with solution comprising a plurality of different probes, wherein said probes bind to different analytes within the cell; and obtaining a two-dimensional or three-dimensional image of the plurality of cells using the imaging system as described herein. In embodiments, the probes are antibodies. In embodiments, the probes are antibodies including a barcode. In embodiments, the method includes imaging a plurality of cells within different wells of a microplate. In embodiments, heating the microplate includes maintaining the temperature for at least 30 minutes, at least 60 minutes, or at least 90 minutes. In embodiments, heating the microplate includes maintaining the temperature (e.g., 100° C.) for about 30 minutes, about 60 minutes, or about 90 minutes.

In an aspect is provided a method of detecting a plurality of nucleic acid molecules and two or more proteins from a cell in situ, the method including contacting the cell with different fluorescently labeled nucleic acid probes, wherein said nucleic acid probes hybridize to different nucleic acid sequences (e.g., different sequences of the same nucleic acid molecule or different sequences of different nucleic acid molecules, such as two different gene sequences) and detecting the fluorescently labeled nucleic acid probes; contacting the cell with different protein probes (e.g., antibodies), wherein the protein probes specifically bind to different proteins and detecting the protein probes. In embodiments, the method detects at least 10, at least 20, at least 30, at least 50, at least 60, at least 70, at least 80, at least 90, at least 100 or more different nucleic acid sequences (e.g., different transcript targets) in the same cell.

In an aspect is provided a method of amplifying a target polynucleotide, the method including: contacting a microplate with a sample including a target polynucleotide; and amplifying the target polynucleotide to produce an amplification product, wherein amplifying includes extension of an amplification primer hybridized to the target polynucleotide. In embodiments, the microplate includes a plurality of wells. In embodiments, amplifying includes a plurality of cycles of strand denaturation, primer hybridization, and primer extension. In embodiments, amplifying includes thermally cycling between (i) about 80-95° C. for about 15-30 sec for denaturation, and (ii) about 50-75° C. for about 1 minute for annealing/extension of the primer. In embodiments, amplifying includes thermally cycling between about 72-80° C. for about 5 seconds to about 30 seconds for denaturation; and (ii) about 60-70° C. for about 30 to 90 seconds for annealing/extension of the primer. In embodiments, amplifying includes thermally cycling between (i) about 67-80° C. for about 5 seconds to about 30 seconds for denaturation; and (ii) about 60-70° C. for about 30 to 90 seconds for annealing/extension of the primer. In embodiments, amplifying includes thermally cycling between about 35° C. and about 65° C. In embodiments, amplifying includes thermally cycling between about 40° C. and about 60° C. In embodiments, amplifying includes thermally cycling between about 40° C. and about 58° C. In embodiments, amplifying includes thermally cycling between about 42° C. and about 62° C. In embodiments, amplifying includes thermally cycling between 35° C. and 65° C. In embodiments, amplifying includes thermally cycling between 40° C. and 60° C. In embodiments, amplifying includes thermally cycling between 40° C. and 58° C. In embodiments, amplifying includes thermally cycling between 42° C. and 62° C. In embodiments, amplifying includes thermally cycling about +/−45° C. In embodiments, amplifying includes thermally cycling about +/−40° C. In embodiments, amplifying includes thermally cycling about +/−35° C. In embodiments, amplifying includes thermally cycling about +/−30° C. In embodiments, amplifying includes thermally cycling about +/−25° C. In embodiments, amplifying includes thermally cycling about +/−20° C. In embodiments, amplifying includes thermally cycling about +/−15° C. In embodiments, amplifying includes thermally cycling about +/−10° C. In embodiments, amplifying includes thermally cycling about +/−5° C. In embodiments, amplifying includes thermally cycling about +/−2° C. In embodiments, the device as described herein is configured to perform amplifying of a target polynucleotide. Primer binding sequences usually have a length in the range of between 3 to 36 nucleotides, also 5 to 24 nucleotides, also from 12 to 36 nucleotides.

In embodiments, amplifying includes contacting the well with an amplification solution (e.g., a buffered solution including a polymerase and dNTPs) for about 5 minutes to about 1 hour, about 5 minutes to about 50 minutes, about 5 minutes to about 40 minutes, about 5 minutes to about 30 minutes, about 5 minutes to about 20 minutes, about 5 minutes to about 10 minutes, about 10 minutes to about 1 hour, about 10 minutes to about 50 minutes, about 10 minutes to about 40 minutes, about 10 minutes to about 30 minutes, about 10 minutes to about 20 minutes, about 20 minutes to about 1 hour, about 20 minutes to about 50 minutes, about 20 minutes to about 40 minutes, about 20 minutes to about 30 minutes, about 30 minutes to about 1 hour, about 30 minutes to about 50 minutes, about 30 minutes to about 40 minutes, about 40 minutes to about 1 hour, about 40 minutes to about 50 minutes, or about 50 minutes to about 1 hour, at an initial temperature of about 4° C. C to about 35° C., about 4° C. to about 30° C., about 4° C. to about 25° C., about 4° C. to about 20° C., about 4° C. to about 15° C., about 4° C. to about 10° C., about 10° C. to about 35° C., about 10° C. to about 30° C., about 10° C. to about 25° C., about 10° C. to about 20° C., about 10° C. to about 15° C., about 15° C. to about 35° C., about 15° C. to about 30° C., about 15° C. to about 25° C., about 15° C. to about 20° C., about 20° C. to about 35° C., about 20° C. to about 30° C., about 20° C. to about 25° C., about 25° C. to about 35° C., about 25° C. to about 30° C., or about 30° C. to about 35° C. In embodiments, amplifying includes modulating the temperature (i.e., thermocycling) between an upper and lower temperature to facilitate hybridization, extension and denaturing.

In another aspect is provided a method of sequencing a plurality of target nucleic acids of a cell in situ on a microplate, the method including the following steps in situ for each of the plurality of target nucleic acids: hybridizing an oligonucleotide primer to the target nucleic acid, wherein the target nucleic acid is on a microplate, circularizing the oligonucleotide primer to generate a circular oligonucleotide, amplifying the circular oligonucleotide by extending an amplification primer hybridized to the circular oligonucleotide with a strand-displacing polymerase, wherein the amplification primer extension generates an extension product including multiple complements of the circular oligonucleotide; and sequencing the extension product. In embodiments, circularizing includes extending the 3' end of the oligonucleotide primer along the target nucleic acid to generate a complementary sequence, and ligating the complementary sequence to the 5' end of the oligonucleotide primer. In embodiments, the device as described herein is configured to perform the method of sequencing a plurality of target nucleic acids of a cell in situ on a microplate. In embodiments, the method includes circularizing and ligating the complementary sequence to the 5' end of the oligonucleotide primer. In embodiments, the ligation includes enzymatic ligation. In embodiments, ligating includes enzymatic ligation including a ligation enzyme (e.g., Circligase™ enzyme, Taq DNA Ligase, HiFi Taq DNA Ligase, T4 ligase, PBCV-1 DNA Ligase (also known as SplintR™ ligase) or Ampligase DNA Ligase). Non-limiting examples of ligases include DNA ligases such as DNA Ligase I, DNA Ligase II, DNA Ligase III, DNA Ligase IV, T4 DNA ligase, T7 DNA ligase, T3 DNA Ligase, *E. coli* DNA Ligase, PBCV-1 DNA Ligase (also known as SplintR™ ligase) or a Taq DNA Ligase. In embodiments, ligating includes chemical ligation (e.g., enzyme-free, click-mediated ligation). In embodiments, the oligonucleotide primer includes a first bioconjugate reactive moiety capable of bonding upon contact with a second (complementary) bioconjugate reactive moiety. SplintR is a trademark of New England Biolabs, Inc.

The oligonucleotide primer is similar to a padlock probe, however with an important distinction. Typically, padlock probes hybridize to adjacent sequences and are then ligated together to form a circular oligonucleotide. The oligonucleotide primers hybridize to sequences adjacent to the target nucleic acid sequence resulting in a gap (e.g., a gap spanning the length of the target nucleic acid sequence). Padlock probes are specialized ligation probes, examples of which are known in the art, see for example Nilsson M, et al. *Science*. 1994; 265(5181):2085-2088), and has been applied to detect transcribed RNA in cells, see for example Christian A T, et al. Proc Natl Acad Sci USA. 2001; 98(25):14238-14243, both of which are incorporated herein by reference in their entireties. The construction of the oligonucleotide primer allows for selective targeting, enabling detection of specific targets within the cell. In embodiments, the oligonucleotide primer includes at least one target-specific region. In embodiments, the oligonucleotide primer includes two target-specific regions. In embodiments, the oligonucleotide primer includes at least one flanking-target region (i.e., an oligonucleotide sequence that flanks the region of interest). In embodiments, the oligonucleotide primer includes two flanking-target regions. A target-specific region is a single stranded polynucleotide that is at least 50% complementary, at least 75% complementary, at least 85% complementary, at least 90% complementary, at least 95% complementary, at least 98%, at least 99% complementary, or 100% complementary to a portion of a nucleic acid molecule that includes a target sequence (e.g., a gene of interest). In embodiments, the target-specific region is capable of hybridizing to at least a portion of the target sequence. In embodiments, the target-specific region is substantially non-complementary to other target sequences present in the sample.

In embodiments, the oligonucleotide primer is approximately 50 to 200 nucleotides. In embodiments, the oligonucleotide primer has a first domain that is capable of hybridizing to a first target sequence domain, and a second ligation domain, capable of hybridizing to a target nucleic acid sequence-adjacent second sequence domain. In embodiments, following hybridization there is a gap between the first target sequence domain, and the second ligation domain, wherein the gap spans the length of the target nucleic acid sequence.

In embodiments, the target nucleic acid can include any nucleic acid of interest. The nucleic acid can include DNA, RNA, peptide nucleic acid, morpholino nucleic acid, locked nucleic acid, glycol nucleic acid, threose nucleic acid, mixtures thereof, and hybrids thereof. In embodiments, the nucleic acid is obtained from one or more source organisms. In some embodiments, the nucleic acid can include a selected sequence or a portion of a larger sequence. In embodiments, sequencing a portion of a nucleic acid or a fragment thereof can be used to identify the source of the nucleic acid. With reference to nucleic acids, polynucleotides and/or nucleotide sequences a "portion," "fragment" or "region" can be at least 5 consecutive nucleotides, at least 10 consecutive nucleotides, at least 15 consecutive nucleotides, at least 20 consecutive nucleotides, at least 25 consecutive nucleotides, at least 50 consecutive nucleotides, at least 100 consecutive nucleotides, or at least 150 consecutive nucleotides.

In another aspect is provided a method of detecting a plurality of different targets within an optically resolved volume of a cell in situ, wherein the targets are nucleic acid sequences or proteins on a microplate; the method including: associating a different oligonucleotide barcode from a known set of barcodes with each of the plurality of targets; sequencing each barcode to obtain a multiplexed signal in the cell in situ; demultiplexing the multiplexed signal by comparison with the known set of barcodes; and detecting the plurality of targets by identifying the associated barcodes detected in the cell. In embodiments, the device as described herein is configured to perform the method of detecting a plurality of different targets within an optically resolved volume of a cell in situ, wherein the targets are nucleic acid sequences or proteins on a microplate. In embodiments, demultiplexing the multiplexed signal includes a linear decomposition of the multiplexed signal. Any of a variety of techniques may be employed for decomposition of the multiplexed signal. Examples include, but are not limited to, Zimmerman et al. Chapter 5: Clearing Up the Signal: Spectral Imaging and Linear Unmixing in Fluorescence Microscopy; Confocal Microscopy: Methods and Protocols, Methods in Molecular Biology, vol. 1075 (2014); Shirawaka H. et al.; Biophysical Journal Volume 86, Issue 3, March 2004, Pages 1739-1752; and S. Schlachter, et al, Opt. Express 17, 22747-22760 (2009); the content of each of which is incorporated herein by reference in its entirety. In embodiments, multiplexed signal includes overlap of a first signal and a second signal and is computationally resolved, for example, by imaging software. In embodiments, more than one analyte type (e.g., nucleic acids and proteins) from a biological sample can be detected (e.g., simultaneously or sequentially) using any appropriate multiplexing technique.

In an aspect is provided a method of detecting a plurality of targets including different nucleic acid sequences within an optically resolved volume of a cell in situ on a microplate; the method including: associating a different oligonucleotide barcode from a known set of barcodes with each of the plurality of targets, wherein associating an oligonucleotide barcode with each of the plurality of targets includes hybridizing a padlock probe to two adjacent nucleic acid sequences of the target, wherein the padlock probe is a single-stranded polynucleotide having a 5' and a 3' end, the padlock probe includes at least one oligonucleotide barcode, and wherein the padlock probe includes a primer binding sequence from a known set of primer binding sequences; sequencing each barcode to obtain a multiplexed signal in the cell in situ; demultiplexing the multiplexed signal by comparison with the known set of barcodes; and detecting the plurality of targets by identifying the associated barcodes detected in the cell. In embodiments, the device as described herein is configured to perform the method of detecting a plurality of targets including different nucleic acid sequences within an optically resolved volume of a cell in situ on a microplate. In embodiments, the oligonucleotide primer includes at least one primer binding sequence. In embodiments, the oligonucleotide primer includes at least two primer binding sequences. In embodiments, the oligonucleotide primer includes an amplification primer binding sequence. In embodiments, the oligonucleotide primer includes a sequencing primer binding sequence. The amplification primer binding sequence refers to a nucleotide sequence that is complementary to a primer useful in initiating amplification (i.e., an amplification primer). Likewise, a sequencing primer binding sequence is a nucleotide sequence that is complementary to a primer useful in initiating sequencing (i.e., a sequencing primer). Primer binding sequences usually have a length in the range of between 3 to 36 nucleotides, also 5 to 24 nucleotides, also from 14 to 36 nucleotides. In embodiments, an amplification primer and a sequencing primer are complementary to the same primer binding sequence, or overlapping primer binding sequences. In embodiments, an amplification primer and a sequencing primer are complementary to different primer binding sequences.

In embodiments, the barcode is at least 5, 6, 7, 8, 9, 10, 11, 12, 13, 14, or 15 nucleotides in length. In embodiments, the barcode is 5, 6, 7, 8, 9, 10, 11, 12, 13, 14, or 15 nucleotides in length. In embodiments, the barcode is 10 to 15 nucleotides in length. An oligonucleotide barcode is at least about 1, 2, 3, 4, 5, 6, 7, 8, 9, 10, 15, 20, 25, 30, 35, 40, 45, 50 or more nucleotides in length. An oligonucleotide barcode can be at most about 300, 200, 100, 90, 80, 70, 60, 50, 40, 30, 20, 15, 12, 10, 9, 8, 7, 6, 5, 4 or fewer or more nucleotides in length. In embodiments, an oligonucleotide barcode includes between about 5 to about 8, about 5 to about 10, about 5 to about 15, about 5 to about 20, about 10 to about 150 nucleotides. In embodiments, an oligonucleotide barcode includes between 5 to 8, 5 to 10, 5 to 15, 5 to 20, 10 to 150 nucleotides. In embodiments, an oligonucleotide barcode is 10 nucleotides. An oligonucleotide barcode may include a unique sequence (e.g., a barcode sequence) that gives the oligonucleotide barcode its identifying functionality. The unique sequence may be random or non-random. Attachment of the barcode sequence to a nucleic acid of interest (i.e., the target) may associate the barcode sequence with the nucleic acid of interest. The barcode may then be used to identify the nucleic acid of interest during sequencing, even when other nucleic acids of interest (e.g., comprising different oligonucleotide barcodes) are present. In embodiments, the oligonucleotide barcode consists only of a unique barcode sequence. In embodiments, the 5' end of a barcoded oligonucleotide is phosphorylated. In embodiments, the oligonucleotide barcode is known (i.e., the nucleic sequence is known before sequencing) and is sorted into a basis-set according to their Hamming distance. Oligonucleotide barcodes can be associated with a target of interest by knowing, a priori, the target of interest, such as a gene or protein. In embodiments, the oligonucleotide barcodes further include one or more sequences capable of specifically binding a gene or nucleic acid sequence of interest. For example, in embodiments, the oligonucleotide barcode includes a sequence capable of hybridizing to mRNA, e.g., one containing a poly-T sequence (e.g., having several T's in a row, e.g., 4, 5, 6, 7, 8, or more T's).

In embodiments, the cell forms part of a tissue in situ. In embodiments, the cell is an isolated single cell. In embodiments, the cell is a prokaryotic cell. In embodiments, the cell is a eukaryotic cell. In embodiments, the cell is a bacterial cell, a fungal cell, a plant cell, or a mammalian cell. In embodiments, the cell is a stem cell. In embodiments, the stem cell is an embryonic stem cell, a tissue-specific stem cell, a mesenchymal stem cell, or an induced pluripotent stem cell. In embodiments, the cell is an endothelial cell, muscle cell, myocardial, smooth muscle cell, skeletal muscle cell, mesenchymal cell, epithelial cell; hematopoietic cell, such as lymphocytes, including T cell, e.g., (Th1 T cell, Th2 T cell, ThO T cell, cytotoxic T cell); B cell, pre-B cell; monocytes; dendritic cell; neutrophils; or a macrophage. In embodiments, the cell is a stem cell, an immune cell, a cancer cell, a viral-host cell, or a cell that selectively binds to a desired target. In embodiments, the cell includes a T cell receptor gene sequence, a B cell receptor gene sequence, or an immunoglobulin gene sequence. In embodiments, the cell includes a Toll-like receptor (TLR) gene sequence. In embodiments, the cell includes a gene sequence corresponding to an immunoglobulin light chain polypeptide and a gene sequence corresponding to an immunoglobulin heavy chain polypeptide. In embodiments, the cell is a genetically modified cell.

In embodiments, the cell is a prokaryotic cell. In embodiments, the cell is a bacterial cell. In embodiments, the bacterial cell is a *Bacteroides, Clostridium, Faecalibacterium, Eubacterium, Ruminococcus, Peptococcus, Peptostreptococcus*, or *Bifidobacterium* cell. In embodiments, the bacterial cell is a *Bacteroides fragilis, Bacteroides melaninogenicus, Bacteroides oralis, Enterococcus faecalis, Escherichia coli, Enterobacter* sp., *Klebsiella* sp., *Bifidobacterium bifidum, Staphylococcus aureus, Lactobacillus*,

*Clostridium perfringens, Proteus mirabilis, Clostridium tetani, Clostridium septicum, Pseudomonas aeruginosa, Salmonella enterica, Faecalibacterium prausnitzii, Peptostreptococcus* sp., or *Peptococcus* sp. cell. In embodiments, the cell is a fungal cell. In embodiments, the fungal cell is a *Candida, Saccharomyces, Aspergillus, Penicillium, Rhodotorula, Trametes, Pleospora, Sclerotinia, Bullera,* or a *Galactomyces* cell. In embodiments, the cell is a viral-host cell. A "viral-host cell" is used in accordance with its ordinary meaning in virology and refers to a cell that is infected with a viral genome (e.g., viral DNA or viral RNA). The cell, prior to infection with a viral genome, can be any cell that is susceptible to viral entry. In embodiments, the viral-host cell is a lytic viral-host cell. In embodiments, the viral-host cell is capable of producing viral protein. In embodiments, the viral-host cell is a lysogenic viral-host cell. In embodiments, the cell is a viral-host cell including a viral nucleic acid sequence, wherein the viral nucleic acid sequence is from a Hepadnaviridae, Adenoviridae, Herpesviridae, Poxviridae, Parvoviridae, Reoviridae, Coronaviridae, Retroviridae virus.

In embodiments, the cell is an adherent cell (e.g., epithelial cell, endothelial cell, or neural cell). Adherent cells are usually derived from tissues of organs and attach to a substrate (e.g., epithelial cells adhere to an extracellular matrix coated substrate via transmembrane adhesion protein complexes). Adherent cells typically require a substrate, e.g., tissue culture plastic, which may be coated with extracellular matrix (e.g., collagen and laminin) components to increase adhesion properties and provide other signals needed for growth and differentiation. Examples of such cells include, but are not limited to, cell lines derived from hematopoietic cells, and from the following cell lines: Colo205, CCRF-CEM, HL-60, K562, MOLT-4, RPMI-8226, SR, HOP-92, NCI-H322M, and MALME-3M. Non-limiting examples of adherent cells include DU145 (prostate cancer) cells, H295R (adrenocortical cancer) cells, HeLa (cervical cancer) cells, KBM-7 (chronic myelogenous leukemia) cells, LNCaP (prostate cancer) cells, MCF-7 (breast cancer) cells, MDA-MB-468 (breast cancer) cells, PC3 (prostate cancer) cells, SaOS-2 (bone cancer) cells, SH-SY5Y (neuroblastoma, cloned from a myeloma) cells, T-47D (breast cancer) cells, THP-1 (acute myeloid leukemia) cells, U87 (glioblastoma) cells, National Cancer Institute's 60 cancer cell line panel (NCI60), vero (African green monkey Chlorocebus kidney epithelial cell line) cells, MC3T3 (embryonic calvarium) cells, GH3 (pituitary tumor) cells, PC12 (pheochromocytoma) cells, dog MDCK kidney epithelial cells, *Xenopus* A6 kidney epithelial cells, zebrafish AB9 cells, and Sf9 insect epithelial cells. In embodiments, the cell is a neuronal cell, an endothelial cell, epithelial cell, germ cell, plasma cell, a muscle cell, peripheral blood mononuclear cell (PBMC), a myocardial cell, or a retina cell.

In embodiments, the cell is bound to a known antigen. In embodiments, the cell is a cell that selectively binds to a desired target, wherein the target is an antibody, or antigen binding fragment, an aptamer, affimer, non-immunoglobulin scaffold, small molecule, or genetic modifying agent. In embodiments, the cell is a leukocyte (i.e., a white-blood cell). In embodiments, leukocyte is a granulocyte (neutrophil, eosinophil, or basophil), monocyte, or lymphocyte (T cells and B cells). In embodiments, the cell is a lymphocyte. In embodiments, the cell is a T cell, an NK cell, or a B cell. In embodiments, the cell is an immune cell. In embodiments, the immune cell is a granulocyte, a mast cell, a monocyte, a neutrophil, a dendritic cell, or a natural killer (NK) cell. In embodiments, the immune cell is an adaptive cell, such as a T cell, NK cell, or a B cell. In embodiments, the cell includes a T cell receptor gene sequence, a B cell receptor gene sequence, or an immunoglobulin gene sequence. In embodiments, the plurality of target nucleic acids includes non-contiguous regions of a nucleic acid molecule. In embodiments, the non-contiguous regions include regions of a VDJ recombination of a B cell or T cell.

In embodiments, the cell is a cancer cell. In embodiments, the cancer is lung cancer, colorectal cancer, skin cancer, colon cancer, pancreatic cancer, breast cancer, cervical cancer, lymphoma, leukemia, or a cancer associated with aberrant K-Ras, aberrant APC, aberrant Smad4, aberrant p53, or aberrant TGFβ. In embodiments, the cancer cell includes a ERBB2, KRAS, TP53, PIK3CA, or FGFR2 gene. In embodiments, the cancer cell includes a HER2 gene (see for example FIG. 6). In embodiments, the cancer cell includes a cancer-associated gene (e.g., an oncogene associated with kinases and genes involved in DNA repair) or a cancer-associated biomarker. A "biomarker" is a substance that is associated with a particular characteristic, such as a disease or condition. A change in the levels of a biomarker may correlate with the risk or progression of a disease or with the susceptibility of the disease to a given treatment. In embodiments, the cancer is Acute Myeloid Leukemia, Adrenocortical Carcinoma, Bladder Urothelial Carcinoma, Breast Ductal Carcinoma, Breast Lobular Carcinoma, Cervical Carcinoma, Cholangiocarcinoma, Colorectal Adenocarcinoma, Esophageal Carcinoma, Gastric Adenocarcinoma, Glioblastoma Multiforme, Head and Neck Squamous Cell Carcinoma, Hepatocellular Carcinoma, Kidney Chromophobe Carcinoma, Kidney Clear Cell Carcinoma, Kidney Papillary Cell Carcinoma, Lower Grade Glioma, Lung Adenocarcinoma, Lung Squamous Cell Carcinoma, Mesothelioma, Ovarian Serous Adenocarcinoma, Pancreatic Ductal Adenocarcinoma, Paraganglioma & Pheochromocytoma, Prostate Adenocarcinoma, Sarcoma, Skin Cutaneous Melanoma, Testicular Germ Cell Cancer, Thymoma, Thyroid Papillary Carcinoma, Uterine Carcinosarcoma, Uterine Corpus Endometrioid Carcinoma, or Uveal Melanoma. In embodiments, the cancer-associated gene is a nucleic acid sequence identified within The Cancer Genome Atlas Program, accessible at www.cancer.gov/tcga.

In embodiments, the cell in situ is obtained from a subject (e.g., human or animal tissue). Once obtained, the cell is placed in an artificial environment in plastic or glass containers supported with specialized medium containing essential nutrients and growth factors to support proliferation. In embodiments, the cell is permeabilized and immobilized to a solid support surface (e.g., a microplate). In embodiments, the cell is permeabilized and immobilized within a well of the microplate. In embodiments, the cell is immobilized to a solid support surface (e.g., a well or a slide). In embodiments, the surface includes a patterned surface (e.g., suitable for immobilization of a plurality of cells in an ordered pattern. In embodiments, a plurality of cells are immobilized in wells of a microplate that have a mean or median separation from one another of about 10-20 µm. In embodiments, a plurality of cells are immobilized in wells of a microplate that have a mean or median separation from one another of about 10-20; 10-50; or 100 µm. In embodiments, a plurality of cells are arrayed on a substrate.

In embodiments, the cell is attached to the substrate via a bioconjugate reactive linker. In embodiments, the cell is attached to the substrate via a specific binding reagent. In embodiments, the specific binding reagent includes an antibody, single-chain Fv fragment (scFv), antibody fragment-antigen binding (Fab), or an aptamer. In embodiments, the specific binding reagent includes an antibody, or antigen binding fragment, an aptamer, affimer, or non-immunoglobulin scaffold. In embodiments, the specific binding reagent is a peptide, a cell penetrating peptide, an aptamer, a DNA aptamer, an RNA aptamer, an antibody, an antibody fragment, a light chain antibody fragment, a single-chain variable fragment (scFv), a lipid, a lipid derivative, a phospholipid, a fatty acid, a triglyceride, a glycerolipid, a glycerophospholipid, a sphingolipid, a saccharolipid, a polyketide, a polylysine, polyethyleneimine, diethylaminoethyl (DEAE)-dextran, cholesterol, or a sterol moiety. Substrates may be prepared for selective capture of particular cells. For example, a substrate containing a plurality of bioconjugate reactive moieties or a plurality of specific binding reagents, optionally in an ordered pattern, contacts a plurality of cells. Only cells containing complementary bioconjugate reactive moieties or complementary specific binding reagents are capable of reacting, and thus adhering, to the substrate. In embodiments, the cell is immobilized to a substrate. Substrates can be two- or three-dimensional and can comprise a planar surface (e.g., a glass slide). A substrate can include glass (e.g., controlled pore glass (CPG)), quartz, plastic (such as polystyrene (low cross-linked and high cross-linked polystyrene), polycarbonate, polypropylene and poly(methylmethacrylate)), acrylic copolymer, polyamide, silicon, metal (e.g., alkanethiolate-derivatized gold), cellulose, nylon, latex, dextran, gel matrix (e.g., silica gel), polyacrolein, or composites. In embodiments, the substrate includes a polymeric coating, optionally containing bioconjugate reactive moieties capable of affixing the sample. Suitable three-dimensional substrates include, for example, spheres, microparticles, beads, membranes, slides, plates, micromachined chips, tubes (e.g., capillary tubes), microwells, microfluidic devices, channels, filters, or any other structure suitable for anchoring a sample. In embodiments, the substrate is not a flow cell. In embodiments, the substrate includes a polymer matrix material (e.g., polyacrylamide, cellulose, alginate, polyamide, cross-linked agarose, cross-linked dextran or cross-linked polyethylene glycol), which may be referred to herein as a "matrix", "synthetic matrix", "exogenous polymer" or "exogenous hydrogel". In embodiments, a matrix may refer to the various components and organelles of a cell, for example, the cytoskeleton (e.g., actin and tubulin), endoplasmic reticulum, Golgi apparatus, vesicles, etc. In embodiments, the matrix is endogenous to a cell. In embodiments, the matrix is exogenous to a cell. In embodiments, the matrix includes both the intracellular and extracellular components of a cell. In embodiments, polynucleotide primers may be immobilized on a matrix including the various components and organelles of a cell. Immobilization of polynucleotide primers on a matrix of cellular components and organelles of a cell is accomplished as described herein, for example, through the interaction/reaction of complementary bioconjugate reactive moieties. In embodiments, the exogenous polymer may be a matrix or a network of extracellular components that act as a point of attachment (e.g., act as an anchor) for the cell to a substrate.

In embodiments, the methods are performed in situ on isolated cells or in tissue sections (alternatively referred to as a sample) that have been prepared according to methodologies known in the art. Methods for permeabilization and fixation of cells and tissue samples are known in the art, as exemplified by Cremer et al., The Nucleus: Volume 1: Nuclei and Subnuclear Components, R. Hancock (ed.) 2008; and Larsson et al., Nat. Methods (2010) 7:395-397, the content of each of which is incorporated herein by reference in its entirety. In embodiments, the cell is cleared (e.g., digested) of proteins, lipids, or proteins and lipids. In embodiments, the biological sample can be permeabilized using any of the methods described herein (e.g., using any of the detergents described herein, e.g., SDS and/or N-lauroylsarcosine sodium salt solution) before or after enzymatic treatment (e.g., treatment with any of the enzymes described herein, e.g., trypin, proteases (e.g., pepsin and/or proteinase K)). In embodiments, the biological sample can be permeabilized by contacting the sample with a permeabilization solution. In some embodiments, the biological sample is permeabilized by exposing the sample to greater than about 1.0 w/v % (e.g., greater than about 2.0 w/v %, greater than about 3.0 w/v %, greater than about 4.0 w/v %, greater than about 5.0 w/v %, greater than about 6.0 w/v %, greater than about 7.0 w/v %, greater than about 8.0 w/v %, greater than about 9.0 w/v %, greater than about 10.0 w/v %, greater than about 11.0 w/v %, greater than about 12.0 w/v %, or greater than about 13.0 w/v %) sodium dodecyl sulfate (SDS) and/or N-lauroylsarcosine or N-lauroylsarcosine sodium salt. In some embodiments, the biological sample can be permeabilized by exposing the sample (e.g., for about 5 minutes to about 1 hour, about 5 minutes to about 40 minutes, about 5 minutes to about 30 minutes, about 5 minutes to about 20 minutes, or about 5 minutes to about 10 minutes) to about 1.0 w/v % to about 14.0 w/v % (e.g., about 2.0 w/v % to about 14.0 w/v %, about 2.0 w/v % to about 12.0 w/v %, about 2.0 w/v % to about 10.0 w/v %, about 4.0 w/v % to about 14.0 w/v %, about 4.0 w/v % to about 12.0 w/v %, about 4.0 w/v % to about 10.0 w/v %, about 6.0 w/v % to about 14.0 w/v %, about 6.0 w/v % to about 12.0 w/v %, about 6.0 w/v % to about 10.0 w/v %, about 8.0 w/v % to about 14.0 w/v %, about 8.0 w/v % to about 12.0 w/v %, about 8.0 w/v % to about 10.0 w/v %, about 10.0% w/v % to about 14.0 w/v %, about 10.0 w/v % to about 12.0 w/v %, or about 12.0 w/v % to about 14.0 w/v %) SDS and/or N-lauroylsarcosine salt solution and/or proteinase K (e.g., at a temperature of about 4% to about 35° C., about 4° C. to about 25° C., about 4° C. to about 20° C., about 4° C. to about 10° C., about 10° C. to about 25° C., about 10° C. to about 20° C., about 10° C. to about 15° C., about 35° C. to about 50° C., about 35° C. to about 45° C., about 35° C. to about 40° C., about 40° C. to about 50° C., about 40° C. to about 45° C., or about 45° C. to about 50° C.).

In embodiments, the cell is exposed to paraformaldehyde (i.e., by contacting the cell with paraformaldehyde). Any suitable permeabilization and fixation technologies can be used for making the cell available for the detection methods provided herein. In embodiments the method includes affixing single cells or tissues to a transparent substrate. Exemplary tissue include those from skin tissue, muscle tissue, bone tissue, organ tissue and the like. In embodiments, the method includes immobilizing the cell in situ to a substrate and permeabilized for delivering probes, enzymes, nucleotides and other components required in the reactions. In embodiments, the cell includes many cells from a tissue section in which the original spatial relationships of the cells are retained. In embodiments, the cell in situ is within a Formalin-Fixed Paraffin-Embedded (FFPE) sample. In embodiments, the cell is subjected to paraffin removal methods, such as methods involving incubation with a hydrocarbon solvent, such as xylene or hexane, followed by two or more washes with decreasing concentrations of an alcohol, such as ethanol. The cell may be rehydrated in a buffer, such as PBS, TBS or MOPs. In embodiments, the FFPE sample is incubated with xylene and washed using ethanol to remove the embedding wax, followed by treatment with Proteinase K to permeabilized the tissue. In embodiments, the cell is fixed with a chemical fixing agent. In embodiments, the chemical fixing agent is formaldehyde or glutaraldehyde. In embodiments, the chemical fixing agent is glyoxal or dioxolane. In embodiments, the chemical fixing agent includes one or more of ethanol, methanol, 2-propanol, acetone, and glyoxal. In embodiments, the chemical fixing agent includes formalin, Greenfix®, Greenfix® Plus, UPM, CyMol®, HOPE®, CytoSkelFix™, F-Solv®, FineFIX®, RCL2/KINFix, UMFIX, Glyo-Fixx®, Histochoice®, or PAXgene®. In embodiments, the cell is fixed within a synthetic three-dimensional matrix (e.g., polymeric material). In embodiments, the synthetic matrix includes polymeric-crosslinking material. In embodiments, the material comprises polyacrylamide, poly-ethylene glycol (PEG), poly(acrylate-co-acrylic acid) (PAA), or Poly(N-isopropylacrylamide) (NIPAM). In embodiments, the sample can be a biological sample selected from the group consisting of a freshly isolated sample, a fixed sample, a frozen sample, an embedded sample, a processed sample, or a combination thereof.

In embodiments the cell is lysed to release nucleic acid or other materials from the cells. For example, the cells may be lysed using reagents (e.g., a surfactant such as Triton®-X or SDS, an enzyme such as lysozyme, lysostaphin, zymolase, cellulase, mutanolysin, glycanases, proteases, mannase, proteinase K, etc.) or a physical lysing mechanism a physical condition (e.g., ultrasound, ultraviolet light, mechanical agitation, etc.). The cells may release, for instance, DNA, RNA, mRNA, proteins, or enzymes. The cells may arise from any suitable source. For instance, the cells may be any cells for which nucleic acid from the cells is desired to be studied or sequenced, etc., and may include one, or more than one, cell type. The cells may be for example, from a specific population of cells, such as from a certain organ or tissue (e.g., cardiac cells, immune cells, muscle cells, cancer cells, etc.), cells from a specific individual or species (e.g., human cells, mouse cells, bacteria, etc.), cells from different organisms, cells from a naturally-occurring sample (e.g., pond water, soil, etc.), or the like. In some cases, the cells may be dissociated from tissue. In embodiments, the method does not include dissociating the cell from the tissue or the cellular microenvironment. In embodiments, the method does not include lysing the cell.

In embodiments, a permeabilization solution can contain additional reagents or a biological sample may be treated with additional reagents in order to optimize biological sample permeabilization. In some embodiments, an additional reagent is an RNA protectant. As used herein, the term "RNA protectant" typically refers to a reagent that protects RNA from RNA nucleases (e.g., RNases). Any appropriate RNA protectant that protects RNA from degradation can be used. A non-limiting example of an RNA protectant includes organic solvents (e.g., at least 60%, 65%, 70%, 75%, 80%, 85%, 90%, or 95% v/v organic solvent), which includes ethanol, methanol, propan-2-ol, acetone, trichloroacetic acid, propanol, polyethylene glycol, acetic acid, or a combination thereof. In embodiments, the RNA protectant includes ethanol, methanol and/or propan-2-ol, or a combination thereof. In embodiments, the RNA protectant includes RNAlater ICE (ThermoFisher Scientific). In embodiments, the RNA protectant includes a salt. The salt may include ammonium sulfate, ammonium bisulfate, ammonium chloride, ammonium acetate, cesium sulfate, cadmium sulfate, cesium iron (II) sulfate, chromium (III) sulfate, cobalt (II) sulfate, copper (II) sulfate, lithium chloride, lithium acetate, lithium sulfate, magnesium sulfate, magnesium chloride, manganese sulfate, manganese chloride, potassium chloride, potassium sulfate, sodium chloride, sodium acetate, sodium sulfate, zinc chloride, zinc acetate and zinc sulfate. In some embodiments, the biological sample is treated with one or more RNA protectants before, contemporaneously with, or after permeabilization.

In embodiments, the method further includes subjecting the cell to expansion microscopy methods and techniques. Expansion allows individual targets (e.g., mRNA or RNA transcripts) which are densely packed within a cell, to be resolved spatially in a high-throughput manner. Expansion microscopy techniques are known in the art and can be performed as described in US 2016/0116384 and Chen et al., Science, 347, 543 (2015), each of which are incorporated herein by reference in their entirety.

In embodiments, the method does not include subjecting the cell to expansion microscopy. Typically, expansion microscopy techniques utilize a swellable polymer or hydrogel (e.g., a synthetic matrix-forming material) which can significantly slow diffusion of enzymes and nucleotides. Matrix forming materials (e.g., a synthetic matrix) include polyacrylamide, cellulose, alginate, polyamide, cross-linked agarose, cross-linked dextran or cross-linked polyethylene glycol. The matrix forming materials can form a matrix by polymerization and/or crosslinking of the matrix forming materials using methods specific for the matrix forming materials and methods, reagents and conditions known to those of skill in the art. Additionally, expansion microscopy techniques may render the temperature of the cell sample difficult to modulate in a uniform, controlled manner. Modulating temperature provides a useful parameter to optimize amplification and sequencing methods.

In embodiments the target is an RNA transcript. In embodiments the target is a single stranded RNA nucleic acid sequence. In embodiments, the target is an RNA nucleic acid sequence or a DNA nucleic acid sequence (e.g., cDNA). In embodiments, the target is a cDNA target nucleic acid sequence and before step i), the RNA nucleic acid sequence is reverse transcribed to generate the cDNA target nucleic acid sequence. In embodiments, the target is genomic DNA (gDNA), mitochondrial DNA, chloroplast DNA, episomal DNA, viral DNA, or copy DNA (cDNA). In embodiments, the target is coding RNA such as messenger RNA (mRNA), and non-coding RNA (ncRNA) such as transfer RNA (tRNA), microRNA (miRNA), small nuclear RNA (snRNA), or ribosomal RNA (rRNA). In embodiments, the target is a cancer-associated gene. In embodiments, to minimize amplification errors or bias, the target is not reverse transcribed to generate cDNA.

In embodiments, the target is an RNA nucleic acid sequence or DNA nucleic acid sequence. In embodiments, the target is an RNA nucleic acid sequence or DNA nucleic acid sequence from the same cell. In embodiments, the target is an RNA nucleic acid sequence. In embodiments, the RNA nucleic acid sequence is stabilized using known techniques in the art. For example, RNA degradation by RNase should be minimized using commercially available solutions, e.g., RNA Later®, RNA Lysis Buffer, or Keratinocyte serum-free medium). In embodiments, the target is messenger RNA (mRNA), transfer RNA (tRNA), micro RNA (miRNA), small interfering RNA (siRNA), small nucleolar RNA (snoRNA), small nuclear RNA (snRNA), Piwi-interacting RNA (piRNA), enhancer RNA (eRNA), or ribosomal RNA (rRNA). In embodiments, the target is pre-mRNA. In embodiments, the target is heterogeneous nuclear RNA (hnRNA). In embodiments, the target is mRNA, tRNA (transfer RNA), rRNA (ribosomal RNA), or noncoding RNA (such as lncRNA (long noncoding RNA)). In embodiments, the targets are on different regions of the same RNA nucleic acid sequence. In embodiments, the targets are cDNA target nucleic acid sequences and before step i), the RNA nucleic acid sequences are reverse transcribed to generate the cDNA target nucleic acid sequences. In embodiments, the targets are not reverse transcribed to cDNA, i.e., the oligonucleotide primer is hybridized directly to the target nucleic acid.

In embodiments, the targets are proteins. In embodiments when the target are proteins, the method includes contacting the proteins with a specific binding reagent, wherein the specific binding reagent comprises an oligonucleotide barcode. In embodiments, the specific binding reagent comprises an antibody, single-chain Fv fragment (scFv), antibody fragment-antigen binding (Fab), or an aptamer. In embodiments, the specific binding reagent is a peptide, a cell penetrating peptide, an aptamer, a DNA aptamer, an RNA aptamer, an antibody, an antibody fragment, a light chain antibody fragment, a single-chain variable fragment (scFv), a lipid, a lipid derivative, a phospholipid, a fatty acid, a triglyceride, a glycerolipid, a glycerophospholipid, a sphingolipid, a saccharolipid, a polyketide, a polylysine, polyethyleneimine, diethylaminoethyl (DEAE)-dextran, cholesterol, or a sterol moiety. In embodiments, the specific binding reagent interacts (e.g., contacts, or binds) with one or more specific binding reagents on the cell surface. Cell surface specific binding reagents corresponding to analytes can include a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, or a posttranslational modification (e.g., phosphorylation, glycosylation, ubiquitination, nitrosylation, methylation, acetylation or lipidation).

In an aspect is provided a method of detecting a plurality of targets including different proteins within an optically resolved volume of a cell in situ on a microplate, the method including: associating a different oligonucleotide barcode from a known set of barcodes with each of the plurality of targets, wherein associating an oligonucleotide barcode with each of the plurality of targets includes contacting each of the targets with a specific binding reagent, wherein the specific binding reagent includes an oligonucleotide barcode, hybridizing a padlock probe to two adjacent nucleic acid sequences of the barcode, wherein the padlock probe is a single-stranded polynucleotide having a 5' and a 3' end, and wherein the padlock probe includes a primer binding sequence from a known set of primer binding sequences; sequencing each barcode to obtain a multiplexed signal in the cell in situ; demultiplexing the multiplexed signal by comparison with the known set of barcodes; and detecting the plurality of targets by identifying the associated barcodes detected in the cell. In embodiments, the device as described herein is configured to perform the method of detecting a plurality of targets including different proteins within an optically resolved volume of a cell in situ on a microplate. In embodiments, the method includes i) associating an oligonucleotide barcode with each of the plurality of targets; ii) sequencing each barcode to obtain a multiplexed signal; and iii) demultiplexing the multiplexed signal to obtain a set of signals corresponding to barcodes with a specified Hamming distance; thereby detecting a plurality of targets within an optically resolved volume of a sample.

In an aspect is provided a method of sequencing an agent-mediated nucleic acid sequence of a cell, the method including administering a genetically modifying agent to the cell, and sequencing an agent-mediated nucleic acid sequence of the cell in situ according to any one of methods described herein. In embodiments, the device as described herein is configured to perform the method of sequencing an agent-mediated nucleic acid sequence of a cell. In embodiments, a statistically significant amount of time passes between administering and sequencing. For example, a genetically modifying agent may be administered to a cell on day 0, and sequencing may occur at least 1, 2, 3, 7, 14, 20, 30, 60, or at least 90 days from day 0.

In an aspect is provided a method of identifying a nucleic acid sequence as an agent-mediated nucleic acid sequence, the method including administering a genetically modifying agent to a cell, detecting whether an agent-mediated nucleic acid sequence is present in the cell by sequencing a plurality of target nucleic acids according to any of the methods described herein, and identifying the nucleic acid sequence as an agent-mediated nucleic acid sequence when the presence of the agent-mediated nucleic acid is detected in the cell. In embodiments, the device as described herein is configured to perform the method of identifying a nucleic acid sequence as an agent-mediated nucleic acid sequence.

In an aspect is provided a method of identifying a cell that responds to a genetically modifying agent, the method including administering a genetically modifying agent to the cell, detecting whether an agent-mediated nucleic acid sequence is present in the cell by sequencing a plurality of target nucleic acids according to any of the methods described herein, and identifying a cell that responds to a genetically modifying agent when the presence of the agent-mediated nucleic acid is detected in the cell. In embodiments, the device as described herein is configured to perform the method of identifying a cell that responds to a genetically modifying agent.

In an aspect is provided a method of identifying an agent as a genetically modifying agent, the method including administering an agent to a cell, detecting whether an agent-mediated nucleic acid sequence is present in the cell by sequencing a plurality of target nucleic acids according to any of the methods described herein, and identifying the agent as a genetically modifying agent when the presence of the agent-mediated nucleic acid is detected in the cell. In embodiments, the device as described herein is configured to perform the method of identifying an agent as a genetically modifying agent. In embodiments, the genetically modifying agent is a pathogen. In embodiments, the genetically modifying agent is a virus. In embodiments, the genetically modifying agent is a DNA virus (e.g., pox virus, herpesvirus, adenovirus, parvovirus, or warts virus). In embodiments, the genetically modifying agent is an RNA virus (e.g., influenza virus, rotavirus, mumps virus, rabies virus, eastern equine encephalitis virus, corona virus, LCM virus, polio virus, or HIV virus). In embodiments, the genetically modifying agent is a toxin. In embodiments, the genetically modifying agent is a small molecule (e.g., a pharmaceutical agent). In embodiments, the genetically modifying agent is a peptide. In embodiments, the genetically modifying agent is a prion.

In embodiments, the methods further includes imaging the cell (e.g., obtaining bright field images (i.e., transmitted light) or dark field images (i.e., scattered light). In embodiments, the method further includes identifying and/or quantifying additional targets of interest (e.g., proteins, nucleic acids, glycolipids, or cellular structures (e.g., nucleus, mitochondria, or organelles). In embodiments, the method includes obtaining cell images for analysis of cell morphology. In embodiments, a plurality of cells are immobilized in a 96-well microplate having a mean or median well-to-well spacing of about 8 mm to about 12 mm (e.g., about 9 mm). In embodiments, a plurality of cells are immobilized in a 384-well microplate having a mean or median well-to-well spacing of about 3 mm to about 6 mm (e.g., about 4.5 mm). In embodiments, the device as described herein detects scattered light from the sample. In embodiments, the device as described herein detects diffracted light from the sample. In embodiments, the device as described herein detects reflected light from the sample. In embodiments, the device as described herein detects absorbed light from the sample. In embodiments, the device as described herein detects refracted light from the sample. In embodiments, the device as described herein detects transmitted light not absorbed by the sample. In embodiments, the sample does not include a label. In embodiments, the methods and system as described herein detect scattered light from the sample. In embodiments, the methods and system as described herein detect diffracted light from the sample. In embodiments, the methods and system as described herein detect reflected light from the sample. In embodiments, the methods and system as described herein detect absorbed light from the sample. In embodiments, the methods and system as described herein detect refracted light from the sample. In embodiments, the methods and system as described herein detect transmitted light not absorbed by the sample. In embodiments, the device is configured to determine the cell morphology (e.g., the cell boundary, granularity, or cell shape). For example, to determining the cell boundary includes comparing the pixel values of an image to a single intensity threshold, which may be determined quickly using histogram-based approaches as described in Carpenter, A. et al Genome Biology 7, R100 (2006) and Arce, S., Sci Rep 3, 2266 (2013)).

In embodiments, the method includes performing an additional image processing techniques (e.g., filtering, masking, smoothing, UnSharp Mask filter (USM), deconvolution, or maximum intensity projection (MIP)). In embodiments, the method includes computationally filtering the emissions using a linear or nonlinear filter that amplifies the high-frequency components of the emission. For example, USM method applies a Gaussian blur to a duplicate of the original image and then compares it to the original. If the difference is greater than a threshold setting, the images are subtracted. In embodiments, the method includes a maximum intensity projection (MIP). A maximum intensity projection is a visualization technique that takes three-dimensional data (e.g., emissions from varying depths obtained according to the methods described herein) and turns it into a single two-dimensional image. For example, the projection takes the brightest pixel (voxel) in each depth and displays that pixel intensity value in the final two-dimensional image. Various machine learning approaches may be used, for example, the methods described in Lugagne et al. Sci Rep 8, 11455 (2018) and Pattarone, G., et al. Sci Rep 11, 10304 (2021), each of which is incorporated herein by reference. In embodiments, the method includes focus stacking (e.g., z-stacking) which combines multiple images taken at different focus distances to give a resulting image with a greater depth of field (DOF) than any of the individual source images. The devices and methods described herein provide for the detection analytes and analyte levels (e.g., gene and/or protein expression) within different cells in a tissue of a mammal or within a single cell. For example, the methods can be used to detect analytes (e.g., genes and/or proteins) within different cells in histological slide samples, the data from which can be reassembled to generate a three-dimensional map of analytes of a tissue sample.

In embodiments, the method includes determining the nucleic acid sequence of the target polynucleotide. In embodiments, the molecule further includes quantifying the target nucleic acid molecule or amplicons. Methods for quantifying a target polynucleotide or amplicon are well known to one skilled in the art. For example, during amplification of the target nucleic acid, quantitative techniques such as real-time polymerase chain reaction (RT-PCR) can be used to quantify the copy number of target nucleic acid molecules present in the clonal object as discussed in Logan et al. Real-Time PCR: Current Technology and Applications, Caister Academic Press. (2009). RT-PCR follows the general principle of polymerase chain reaction, however inclusion of detection molecules, such as non-specific fluorescent dyes that intercalate with any double-stranded DNA, or sequence-specific DNA probes consisting of oligonucleotides that are labeled with a fluorescent reporter, which permits detection only after hybridization of the probe with its complementary DNA target, allows for the detection of nucleic acid formed during amplification. The rate of detectable molecules is proportional to the copy number of target nucleic acid molecules present in the clonal object. Furthermore, quantifying the target nucleic acid molecule or amplicons can be done following amplification using standard gel electrophoresis and/or Southern blot techniques, which are well known in the art.

In embodiments, the method further includes sequencing the amplification product(s). Sequencing includes, for example, detecting a sequence of signals within the particle. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes. In embodiments, the readout is accomplished by epifluorescence imaging. A variety of sequencing chemistries are available, non-limiting examples of which are described herein.

In an aspect is provided a method of sequencing a target polynucleotide, the method including contacting a microplate (e.g., a microplate array) as described herein. In embodiments, the microplate includes a solid support including a surface, the surface comprising a plurality of wells separated from each other by interstitial regions on the surface, wherein one or more wells includes a particle, wherein the particle includes a plurality of bioconjugate reactive moieties; and wherein there is at least one particle per well. In embodiments, each oligonucleotide moiety includes a bioconjugate reactive moiety that reacts and forms a bioconjugate linker that covalently links the oligonucleotide moiety to the particle. In embodiments, the method includes contacting the microplate with a sample including a target polynucleotide; and amplifying the target polynucleotide to produce an amplification product, wherein amplifying includes extension of the oligonucleotide moiety hybridized to the target polynucleotide. In embodiments, the method includes sequencing the amplification product. The initiation point for a sequencing reaction may be provided by annealing of a sequencing primer to a target polynucleotide present at a feature of the microplate. In embodiments, a known adapter sequence region that is present on a target nucleic acid, for example, as a result of an amplification reaction described previously herein, can be used as a priming site for annealing of a sequencing primer. In embodiments, a sequencing reaction includes steps of hybridizing a sequencing primer to a single-stranded region of a linearized amplification product, sequentially incorporating one or more nucleotides into a nucleic acid strand complementary to the region of amplified template strand to be sequenced, identifying the base present in one or more of the incorporated nucleotide(s) and thereby determining the sequence of a region of the template strand.

In an aspect is provided a method of sequencing a target polynucleotide, the method including contacting a microplate with a sample including a target polynucleotide. In embodiments, the microplate includes a solid support including a surface, the surface comprising a plurality of wells separated from each other by interstitial regions on the surface, wherein one or more wells includes a particle, wherein the particle includes a plurality of oligonucleotide moieties; and wherein there is at least one particle per well. In embodiments, the method includes amplifying the target polynucleotide to produce an amplification product, wherein amplifying includes extension of the oligonucleotide moiety hybridized to the target polynucleotide. In embodiments, the method includes sequencing the amplification product.

In embodiments, sequencing includes extending a sequencing primer to incorporate a nucleotide containing a detectable label that indicates the identity of a nucleotide in the target polynucleotide, detecting the detectable label, and repeating the extending and detecting of steps. In embodiments, the methods include sequencing one or more bases of a target nucleic acid by extending a sequencing primer hybridized to a target nucleic acid (e.g., an amplification product of a target nucleic acid). In embodiments, the sequencing includes sequencing-by-synthesis, sequencing by ligation, sequencing-by-hybridization, or pyrosequencing, and generates a sequencing read. In embodiments, generating a sequencing read includes executing a plurality of sequencing cycles, each cycle including extending the sequencing primer by incorporating a nucleotide or nucleotide analogue using a polymerase and detecting a characteristic signature indicating that the nucleotide or nucleotide analogue has been incorporated.

In embodiments, sequencing includes a plurality of sequencing cycles. In embodiments, sequencing includes 20 to 100 sequencing cycles. In embodiments, sequencing includes 50 to 100 sequencing cycles. In embodiments, sequencing includes 50 to 300 sequencing cycles. In embodiments, sequencing includes 50 to 150 sequencing cycles. In embodiments, sequencing includes at least 10, 20, 30 40, or 50 sequencing cycles. In embodiments, sequencing includes at least 10 sequencing cycles. In embodiments, sequencing includes 10 to 20 sequencing cycles. In embodiments, sequencing includes 10, 11, 12, 13, 14, or 15 sequencing cycles. In embodiments, sequencing includes (a) extending a sequencing primer by incorporating a labeled nucleotide, or labeled nucleotide analogue and (b) detecting the label to generate a signal for each incorporated nucleotide or nucleotide analogue. In embodiments, detecting includes two-dimensional (2D) or three-dimensional (3D) fluorescent microscopy. Suitable imaging technologies are known in the art, as exemplified by Larsson et al., Nat. Methods (2010) 7:395-397 and associated supplemental materials, the entire content of which is incorporated by reference herein in its entirety. In embodiments of the methods provided herein, the imaging is accomplished by confocal microscopy. Confocal fluorescence microscopy involves scanning a focused laser beam across the sample, and imaging the emission from the focal point through an appropriately-sized pinhole. This suppresses the unwanted fluorescence from sections at other depths in the sample. In embodiments, the imaging is accomplished by multi-photon microscopy (e.g., two-photon excited fluorescence or two-photon-pumped microscopy). Unlike conventional single-photon emission, multi-photon microscopy can utilize much longer excitation wavelength up to the red or near-infrared spectral region. This lower energy excitation requirement enables the implementation of semiconductor diode lasers as pump sources to significantly enhance the photostability of materials. Scanning a single focal point across the field of view is likely to be too slow for many sequencing applications. To speed up the image acquisition, an array of multiple focal points can be used. The emission from each of these focal points can be imaged onto a detector, and the time information from the scanning mirrors can be translated into image coordinates. Alternatively, the multiple focal points can be used just for the purpose of confining the fluorescence to a narrow axial section, and the emission can be imaged onto an imaging detector, such as a CCD, EMCCD, or s-CMOS detector. A scientific grade CMOS detector offers an optimal combination of sensitivity, readout speed, and low cost. One configuration used for confocal microscopy is spinning disk confocal microscopy. In 2-photon microscopy, the technique of using multiple focal points simultaneously to parallelize the readout has been called Multifocal Two-Photon Microscopy (MTPM). Several techniques for MTPM are available, with applications typically involving imaging in biological tissue. In embodiments of the methods provided herein, the imaging is accomplished by light sheet fluorescence microscopy (LSFM). In embodiments, detecting includes 3D structured illumination (3DSIM). In 3DSIM, patterned light is used for excitation, and fringes in the Moiré pattern generated by interference of the illumination pattern and the sample, are used to reconstruct the source of light in three dimensions. In order to illuminate the entire field, multiple spatial patterns are used to excite the same physical area, which are then digitally processed to reconstruct the final image. See York, Andrew G., et al. "Instant super-resolution imaging in live cells and embryos via analog image processing." *Nature methods* 10.11 (2013): 1122-1126 which is incorporated herein by reference. In embodiments, detecting includes selective planar illumination microscopy, light sheet microscopy, emission manipulation, pinhole confocal microscopy, aperture correlation confocal microscopy, volumetric reconstruction from slices, deconvolution microscopy, or aberration-corrected multifocus microscopy. In embodiments, detecting includes digital holographic microscopy (see for example Manoharan, V. N. Frontiers of Engineering: Reports on Leading-edge Engineering from the 2009 Symposium, 2010, 5-12, which is incorporated herein by reference). In embodiments, detecting includes confocal microscopy, light sheet microscopy, or multi-photon microscopy.

In embodiments, detecting includes contacting the target of interest (e.g., a nucleic acid, protein, or biomolecule) with a fluorescently labeled probe and detecting the probe following hybridization. In embodiments, detecting includes contacting the sample with an detection solution (e.g., a buffered solution including a detectable agent, such as a fluorescently labeled probe) for about 5 minutes to about 1 hour, about 5 minutes to about 50 minutes, about 5 minutes to about 40 minutes, about 5 minutes to about 30 minutes, about 5 minutes to about 20 minutes, about 5 minutes to about 10 minutes, about 10 minutes to about 1 hour, about 10 minutes to about 50 minutes, about 10 minutes to about 40 minutes, about 10 minutes to about 30 minutes, about 10 minutes to about 20 minutes, about 20 minutes to about 1 hour, about 20 minutes to about 50 minutes, about 20 minutes to about 40 minutes, about 20 minutes to about 30 minutes, about 30 minutes to about 1 hour, about 30 minutes to about 50 minutes, about 30 minutes to about 40 minutes, about 40 minutes to about 1 hour, about 40 minutes to about 50 minutes, or about 50 minutes to about 1 hour, at a temperature of about 4° C. C to about 35° C., about 4° C. to about 30° C., about 4° C. to about 25° C., about 4° C. to about 20° C., about 4° C. to about 15° C., about 4° C. to about 10° C., about 10° C. to about 35° C., about 10° C. to about 30° C., about 10° C. to about 25° C., about 10° C. to about 20° C., about 10° C. to about 15° C., about 15° C. to about 35° C., about 15° C. to about 30° C., about 15° C. to about 25° C., about 15° C. to about 20° C., about 20° C. to about 35° C., about 20° C. to about 30° C., about 20° C. to about 25° C., about 25° C. to about 35° C., about 25° C. to about 30° C., or about 30° C. to about 35° C., and detecting the detectable agent of the detection solution.

In embodiments, the method includes sequencing the first and/or the second strand of a amplification product by extending a sequencing primer hybridized thereto. A variety of sequencing methodologies can be used such as sequencing-by-synthesis (SBS), pyrosequencing, sequencing by ligation (SBL), or sequencing by hybridization (SBH). Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210,891; 6,258,568; and. 6,274,320, each of which is incorporated herein by reference in its entirety). In pyrosequencing, released PPi can be detected by being converted to adenosine triphosphate (ATP) by ATP sulfurylase, and the level of ATP generated can be detected via light produced by luciferase. In this manner, the sequencing reaction can be monitored via a luminescence detection system. In both SBL and SBH methods, target nucleic acids, and amplicons thereof, that are present at features of an array are subjected to repeated cycles of oligonucleotide delivery and detection. SBL methods, include those described in Shendure et al. Science 309:1728-1732 (2005); U.S. Pat. Nos. 5,599,675; and 5,750,341, each of which is incorporated herein by reference in its entirety; and the SBH methodologies are as described in Bains et al., Journal of Theoretical Biology 135(3), 303-7 (1988); Drmanac et al., Nature Biotechnology 16, 54-58 (1998); Fodor et al., Science 251(4995), 767-773 (1995); and WO 1989/10977, each of which is incorporated herein by reference in its entirety.

In SBS, extension of a nucleic acid primer along a nucleic acid template is monitored to determine the sequence of nucleotides in the template. The underlying chemical process can be catalyzed by a polymerase, wherein fluorescently labeled nucleotides are added to a primer (thereby extending the primer) in a template dependent fashion such that detection of the order and type of nucleotides added to the primer can be used to determine the sequence of the template. A plurality of different nucleic acid fragments can be subjected to an SBS technique under conditions where events occurring for different templates can be distinguished due to their location in the array. In embodiments, the sequencing step includes annealing and extending a sequencing primer to incorporate a detectable label that indicates the identity of a nucleotide in the target polynucleotide, detecting the detectable label, and repeating the extending and detecting steps. In embodiments, the methods include sequencing one or more bases of a target nucleic acid by extending a sequencing primer hybridized to a target nucleic acid (e.g., an amplification product produced by the amplification methods described herein). In embodiments, the sequencing step may be accomplished by an SBS process. In embodiments, sequencing comprises a sequencing by synthesis process, where individual nucleotides are identified iteratively, as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 10,738,072. Once such a modified nucleotide has been incorporated into the growing polynucleotide chain complementary to the region of the template being sequenced, there is no free 3'-OH group available to direct further sequence extension and therefore the polymerase cannot add further nucleotides. Once the identity of the base incorporated into the growing chain has been determined, the 3' block may be removed to allow addition of the next successive nucleotide. By ordering the products derived using these modified nucleotides it is possible to deduce the DNA sequence of the DNA template. Non-limiting examples of suitable labels are described in U.S. Pat. Nos. 8,178,360, 5,188,934 (4,7-dichlorofluorscein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthene dyes): U.S. Pat. No. 5,688,648 (energy transfer dyes); and the like.

Sequencing includes, for example, detecting a sequence of signals. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes. In embodiments, the nucleotides are labeled with at least two unique fluorescent dyes. In embodiments, the readout is accomplished by epifluorescence imaging. A variety of sequencing chemistries are available, non-limiting examples of which are described herein.

Use of the sequencing method outlined above is a non-limiting example, as essentially any sequencing methodology which relies on successive incorporation of nucleotides into a polynucleotide chain can be used. Suitable alternative techniques include, for example, pyrosequencing methods, FISSEQ (fluorescent in situ sequencing), MPSS (massively parallel signature sequencing), or sequencing by ligation-based methods.

A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may comprise cells or tissues that are normal, healthy, diseased (e.g., infected), and/or cancerous (e.g., cancer cells). A sample obtained from a subject may comprise cells or cellular material (e.g., nucleic acids) of multiple organisms (e.g., virus nucleic acid, fetal nucleic acid, bacterial nucleic acid, parasite nucleic acid). A sample may include a cell and RNA transcripts. A sample can comprise nucleic acids obtained from one or more subjects. In some embodiments a sample comprises nucleic acid obtained from a single subject. A subject can be any living or non-living organism, including but not limited to a human, non-human animal, plant, bacterium, fungus, virus, or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a plant. In some embodiments, a subject is a human subject. A subject can be a patient (e.g., a human patient). In some embodiments a subject is suspected of having a genetic variation or a disease or condition associated with a genetic variation.

It will be appreciated that any of the amplification methodologies described herein or known in the art can be utilized with universal or target-specific primers to amplify the target polynucleotide. Suitable methods for amplification include, but are not limited to, the polymerase chain reaction (PCR), strand displacement amplification (SDA), transcription mediated amplification (TMA) and nucleic acid sequence-based amplification (NASBA), for example, as described in U.S. Pat. No. 8,003,354, which is incorporated herein by reference in its entirety. The above amplification methods can be employed to amplify one or more nucleic acids of interest. Additional examples of amplification processes include, but are not limited to, bridge-PCR, recombinase polymerase amplification (RPA), loop-mediated isothermal amplification (LAMP), rolling circle amplification (RCA), strand displacement amplification, RCA with exponential strand displacement amplification. In embodiments, amplification comprises an isothermal amplification reaction. In embodiments, amplification comprises bridge amplification. In general, bridge amplification uses repeated steps of annealing of primers to templates, primer extension, and separation of extended primers from templates. Because primers are attached within the core polymer, the extension products released upon separation from an initial template is also attached within the core. The 3' end of an amplification product is then permitted to anneal to a nearby reverse primer that is also attached within the core, forming a "bridge" structure. The reverse primer is then extended to produce a further template molecule that can form another bridge. In embodiments, forward and reverse primers hybridize to primer binding sites that are specific to a particular target nucleic acid. In embodiments, forward and reverse primers hybridize to primer binding sites that have been added to, and are common among, target polynucleotides. Adding a primer binding site to target nucleic acids can be accomplished by any suitable method, examples of which include the use of random primers having common 5' sequences and ligating adapter nucleotides that include the primer binding site. Examples of additional clonal amplification techniques include, but are not limited to, bridge PCR, solid-phase rolling circle amplification (RCA), solid-phase exponential rolling circle amplification, solid-phase recombinase polymerase amplification (RPA), solid-phase helicase dependent amplification (HDA), template walking amplification, emulsion PCR on particles (beads), or combinations of the aforementioned methods. Optionally, during clonal amplification, additional solution-phase primers can be supplemented in the microplate for enabling or accelerating amplification. In embodiments, the amplifying includes rolling circle amplification (RCA) or rolling circle transcription (RCT) (see, e.g., Lizardi et al., Nat. Genet. 19:225-232 (1998), which is incorporated herein by reference in its entirety). Several suitable rolling circle amplification methods are known in the art. For example, RCA amplifies a circular polynucleotide (e.g., DNA) by polymerase extension of an amplification primer complementary to a portion of the template polynucleotide. This process generates copies of the circular polynucleotide template such that multiple complements of the template sequence arranged end to end in tandem are generated (i.e., a concatemer) locally preserved at the site of the circle formation. In embodiments, the amplifying occurs at isothermal conditions. In embodiments, the amplifying includes hybridization chain reaction (HCR). HCR uses a pair of complementary, kinetically trapped hairpin oligomers to propagate a chain reaction of hybridization events, as described in Dirks, R. M., & Pierce, N. A. (2004) PNAS USA, 101(43), 15275-15278, which is incorporated herein by reference for all purposes. In embodiments, the amplifying includes branched rolling circle amplification (BRCA); e.g., as described in Fan T, Mao Y, Sun Q, et al. Cancer Sci. 2018; 109:2897-2906, which is incorporated herein by reference in its entirety. In embodiments, the amplifying includes hyberbranched rolling circle amplification (HRCA). Hyperbranched RCA uses a second primer complementary to the first amplification product. This allows products to be replicated by a strand-displacement mechanism, which yields drastic amplification within an isothermal reaction (Lage et al., Genome Research 13:294-307 (2003), which is incorporated herein by reference in its entirety). In embodiments, amplifying includes polymerase extension of an amplification primer. In embodiments, the polymerase is T4, T7, Sequenase, Taq, Klenow, and Pol I DNA polymerases. SD polymerase, Bst large fragment polymerase, or a phi29 polymerase or mutant thereof.

In embodiments, amplifying includes contacting the microplate with one or more reagents for amplifying the target polynucleotide. Examples of reagents include but are not limited to polymerase, buffer, and nucleotides (e.g., an amplification reaction mixture). In certain embodiments the term "amplifying" refers to a method that includes a polymerase chain reaction (PCR). Conditions conducive to amplification (i.e., amplification conditions) are known and often comprise at least a suitable polymerase, a suitable template, a suitable primer or set of primers, suitable nucleotides (e.g., dNTPs), a suitable buffer, and application of suitable annealing, hybridization and/or extension times and temperatures. In embodiments, amplifying generates an amplicon. In embodiments, an amplicon contains multiple, tandem copies of the circularized nucleic acid molecule of the corresponding sample nucleic acid. The number of copies can be varied by appropriate modification of the amplification reaction including, for example, varying the number of amplification cycles run, using polymerases of varying processivity in the amplification reaction and/or varying the length of time that the amplification reaction is run, as well as modification of other conditions known in the art to influence amplification yield. Generally, the number of copies of a nucleic acid in an amplicon is at least 100, 200, 500, 1000, 2000, 3000, 4000, 5000, 6000, 7000, 8000, 9000 and 10,000 copies, and can be varied depending on the application. As disclosed herein, one form of an amplicon is as a nucleic acid "ball" localized to the particle and/or well of the array. The number of copies of the nucleic acid can therefore provide a desired size of a nucleic acid "ball" or a sufficient number of copies for subsequent analysis of the amplicon, e.g., sequencing.

In embodiments, amplifying includes bridge polymerase chain reaction (bPCR) amplification, solid-phase rolling circle amplification (RCA), solid-phase exponential rolling circle amplification (eRCA), solid-phase recombinase polymerase amplification (RPA), solid-phase helicase dependent amplification (HDA), template walking amplification, or emulsion PCR on particles, or combinations of the methods. In embodiments, amplifying includes a bridge polymerase chain reaction amplification. In embodiments, amplifying includes a thermal bridge polymerase chain reaction (t-bPCR) amplification. In embodiments, amplifying includes a chemical bridge polymerase chain reaction (c-bPCR) amplification. Chemical bridge polymerase chain reactions include fluidically cycling a denaturant (e.g., formamide) and one or more additives (e.g., ethylene glycol) and maintaining the temperature within a narrow temperature range (e.g., +/−5° C.) or isothermally. In embodiments, c-bPCR does not include isothermal amplification, rather it requires minor (e.g., +/−5° C.) thermal oscillations. In contrast, thermal bridge polymerase chain reactions include thermally cycling between high temperatures (e.g., 85° C.-95° C.) and low temperatures (e.g., 60° C.-70° C.). Thermal bridge polymerase chain reactions may also include a denaturant, typically at a much lower concentration than traditional chemical bridge polymerase chain reactions. In embodiments, amplifying includes generating a double-stranded amplification product.

In embodiments, the optically resolved volume has an axial resolution (i.e., depth, or z) that is greater than the lateral resolution (i.e., xy plane). In embodiments, the optically resolved volume has an axial resolution that is greater than twice the lateral resolution. In embodiments, the dimensions (i.e., the x, y, and z dimensions) of the optically resolved volume are about 0.5 µm×0.5 µm×0.5 µm; 1 µm×1 µm×1 µm; 2 µm×2 µm×2 µm; 0.5 µm×0.5 µm×1 µm; 0.5 µm×0.5 µm×2 µm; 2 µm×2 µm×1 µm; or 1 µm×1 µm×2 µm.

In embodiments, the method further includes an additional imaging modality or histochemistry modality (e.g., immunostaining). Immunohistochemistry (IHC) is a powerful technique that exploits the specific binding between an antibody and antigen to detect and localize specific antigens in cells and tissue, commonly detected and examined with the light microscope. Known IHC modalities may be used, such as the protocols described in Magaki, S., Hojat, S. A., Wei, B., So, A., & Yong, W. H. (2019). *Methods in molecular biology* (Clifton, N.J.), 1897, 289-298, which is incorporated herein by reference. In embodiments, the additional imaging modality includes bright field microscopy, phase contrast microscopy, Nomarski differential-interference-contrast microscopy, or dark field microscopy. In embodiments, the method further includes determining the cell morphology (e.g., the cell boundary or cell shape) using known methods in the art. For example, to determining the cell boundary includes comparing the pixel values of an image to a single intensity threshold, which may be determined quickly using histogram-based approaches as described in Carpenter, A. et al Genome Biology 7, R100 (2006) and Arce, S., Sci Rep 3, 2266 (2013)). In embodiments, the method further includes an additional imaging modality or histochemistry modality (e.g., Hematoxylin and eosin stain (or haematoxylin and eosin stain or hematoxylin-eosin stain; often abbreviated as H&E stain or HE stain)).

In embodiments, the method includes fixing and/or staining the sample. In embodiments of any of the methods described herein, the non-permeabilized biological sample is fixed and/or stained prior. In embodiments, the step of fixing the sample includes the use of a fixative (e.g., contacting and/or incubating with the sample) such as ethanol, methanol, acetone, formaldehyde, paraformaldehyde-Triton®, glutaraldehyde, and combinations thereof. In embodiments, the staining the sample includes contacting and/or incubating with the sample acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, safranin, and combinations thereof. In embodiments, staining includes contacting the sample with eosin and hematoxylin. In embodiments, staining includes contacting the sample with a detectable label selected from the group consisting of a radioisotope, a fluorophore, a chemiluminescent compound, a bioluminescent compound, or a combination thereof.

The biological targets or molecules to be detected can be any biological molecules including but not limited to proteins, nucleic acids, lipids, carbohydrates, ions, or multi-component complexes containing any of the above. Examples of subcellular targets include organelles, e.g., mitochondria, Golgi apparatus, endoplasmic reticulum, chloroplasts, endocytic vesicles, exocytic vesicles, vacuoles, lysosomes, etc. Exemplary nucleic acid targets can include genomic DNA of various conformations (e.g., A-DNA, B-DNA, Z-DNA), mitochondria DNA (mtDNA), mRNA, tRNA, rRNA, hRNA, miRNA, and piRNA.

In embodiments, the collection of information (e.g., sequencing information and cell morphology) is referred to as a signature. The term "signature" may encompass any gene or genes, protein or proteins, or epigenetic element(s) whose expression profile or whose occurrence is associated with a specific cell type, subtype, or cell state of a specific cell type or subtype within a population of cells. It is to be understood that also when referring to proteins (e.g., differentially expressed proteins), such may fall within the definition of "gene" signature. Levels of expression or activity or prevalence may be compared between different cells in order to characterize or identify for instance signatures specific for cell (sub)populations. Increased or decreased expression or activity of signature genes may be compared between different cells in order to characterize or identify for instance specific cell (sub)populations.

In embodiments, the methods described herein may further include constructing a 3-dimensional pattern of abundance, expression, and/or activity of each target from spatial patterns of abundance, expression, and/or activity of each target of multiple samples. In embodiments, the multiple samples can be consecutive tissue sections of a 3-dimensional tissue sample.

In embodiments, the method further includes digesting the tissue section by contacting the sample-carrier construct with an endopeptidase. In embodiments, the endopeptidase is pepsin.

In embodiments, the method further includes removing the embedding material from the sample. For example, if the embedding material is paraffin wax, the embedding material is removed by contacting the sample-carrier construct with a hydrocarbon solvent, such as xylene or hexane, followed by two or more washes with decreasing concentrations of an alcohol, such as ethanol.

The methods can be used to characterize a cancer or metastasis thereof, including without limitation, a carcinoma, a sarcoma, a lymphoma or leukemia, a germ cell tumor, a blastoma, or other cancers. Carcinomas include without limitation epithelial neoplasms, squamous cell neoplasms squamous cell carcinoma, basal cell neoplasms basal cell carcinoma, transitional cell papillomas and carcinomas, adenomas and adenocarcinomas (glands), adenoma, adenocarcinoma, linitis plastica insulinoma, glucagonoma, gastrinoma, vipoma, cholangiocarcinoma, hepatocellular carcinoma, adenoid cystic carcinoma, carcinoid tumor of appendix, prolactinoma, oncocytoma, hurthle cell adenoma, renal cell carcinoma, grawitz tumor, multiple endocrine adenomas, endometrioid adenoma, adnexal and skin appendage neoplasms, mucoepidermoid neoplasms, cystic, mucinous and serous neoplasms, cystadenoma, pseudomyxoma peritonei, ductal, lobular and medullary neoplasms, acinar cell neoplasms, complex epithelial neoplasms, warthin's tumor, thymoma, specialized gonadal neoplasms, sex cord stromal tumor, thecoma, granulosa cell tumor, arrhenoblastoma, sertoli leydig cell tumor, glomus tumors, paraganglioma, pheochromocytoma, glomus tumor, nevi and melanomas, melanocytic nevus, malignant melanoma, melanoma, nodular melanoma, dysplastic nevus, lentigo maligna melanoma, superficial spreading melanoma, and malignant acral lentiginous melanoma. Sarcoma includes without limitation Askin's tumor, botryodies, chondrosarcoma, Ewing's sarcoma, malignant hemangio endothelioma, malignant schwannoma, osteosarcoma, soft tissue sarcomas including: alveolar soft part sarcoma, angiosarcoma, cystosarcoma phyllodes, dermatofibrosarcoma, desmoid tumor, desmoplastic small round cell tumor, epithelioid sarcoma, extraskeletal chondrosarcoma, extraskeletal osteosarcoma, fibrosarcoma, hemangiopericytoma, hemangiosarcoma, kaposi's sarcoma, leiomyosarcoma, liposarcoma, lymphangiosarcoma, lymphosarcoma, malignant fibrous histiocytoma, neurofibrosarcoma, rhabdomyosarcoma, and synovialsarcoma. Lymphoma and leukemia include without limitation chronic lymphocytic leukemia/small lymphocytic lymphoma, B-cell prolymphocytic leukemia, lymphoplasmacytic lymphoma (such as waldenstrom macroglobulinemia), splenic marginal zone lymphoma, plasma cell myeloma, plasmacytoma, monoclonal immunoglobulin deposition diseases, heavy chain diseases, extranodal marginal zone B cell lymphoma, also called malt lymphoma, nodal marginal zone B cell lymphoma (nmzl), follicular lymphoma, mantle cell lymphoma, diffuse large B cell lymphoma, mediastinal (thymic) large B cell lymphoma, intravascular large B cell lymphoma, primary effusion lymphoma, burkitt lymphoma/leukemia, T cell prolymphocytic leukemia, T cell large granular lymphocytic leukemia, aggressive NK cell leukemia, adult T cell leukemia/lymphoma, extranodal NK/T cell lymphoma, nasal type, enteropathy-type T cell lymphoma, hepatosplenic T cell lymphoma, blastic NK cell lymphoma, mycosis fungoides/sezary syndrome, primary cutaneous CD30-positive T cell lymphoproliferative disorders, primary cutaneous anaplastic large cell lymphoma, lymphomatoid papulosis, angioimmunoblastic T cell lymphoma, peripheral T cell lymphoma, unspecified, anaplastic large cell lymphoma, classical hodgkin lymphomas (nodular sclerosis, mixed cellularity, lymphocyte-rich, lymphocyte depleted or not depleted), and nodular lymphocyte-predominant hodgkin lymphoma. Germ cell tumors include without limitation germinoma, dysgerminoma, seminoma, nongerminomatous germ cell tumor, embryonal carcinoma, endodermal sinus turmor, choriocarcinoma, teratoma, polyembryoma, and gonadoblastoma. Blastoma includes without limitation nephroblastoma, medulloblastoma, and retinoblastoma. Other cancers include without limitation labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma.

In embodiments, the method includes imaging the immobilized tissue section. In embodiments, the method further includes an imaging modality, immunofluorescence (IF), or immunohistochemistry modality (e.g., immunostaining). In embodiments, the method includes ER staining (e.g., contacting the tissue section with a cell-permeable dye which localizes to the endoplasmic reticula), Golgi staining (e.g., contacting the tissue section with a cell-permeable dye which localizes to the Golgi), F-actin staining (e.g., contacting the tissue section with a phalloidin-conjugated dye that binds to actin filaments), lysosomal staining (e.g., contacting the tissue section with a cell-permeable dye that accumulates in the lysosome via the lysosome pH gradient), mitochondrial staining (e.g., contacting the tissue section with a cell-permeable dye which localizes to the mitochondria), nucleolar staining, or plasma membrane staining. For example, the method includes live cell imaging (e.g., obtaining images of the tissue section) prior to or during fixing, immobilizing, and permeabilizing the tissue section. Immunohistochemistry (IHC) is a powerful technique that exploits the specific binding between an antibody and antigen to detect and localize specific antigens in cells and tissue, commonly detected and examined with the light microscope. Known IHC modalities may be used, such as the protocols described in Magaki, S., Hojat, S. A., Wei, B., So, A., & Yong, W. H. (2019). *Methods in molecular biology* (Clifton, N.J.), 1897, 289-298, which is incorporated herein by reference. In embodiments, the additional imaging modality includes bright field microscopy, phase contrast microscopy, Nomarski differential-interference-contrast microscopy, or dark field microscopy. In embodiments, the method further includes determining the cell morphology of the tissue section (e.g., the cell boundary or cell shape) using known methods in the art. For example, to determining the cell boundary includes comparing the pixel values of an image to a single intensity threshold, which may be determined quickly using histogram-based approaches as described in Carpenter, A. et al Genome Biology 7, R100 (2006) and Arce, S., Sci Rep 3, 2266 (2013)). By "microscopic analysis" is meant the analysis of a specimen using techniques that provide for the visualization of aspects of a specimen that cannot be seen with the unaided eye, i.e., that are not within the resolution range of the normal human eye. Such techniques may include, without limitation, optical microscopy, e.g., bright field, oblique illumination, dark field, phase contrast, differential interference contrast, interference reflection, epifluorescence, confocal microscopy, CLARITY-optimized light sheet microscopy (COLM), light field microscopy, tissue expansion microscopy, etc., laser microscopy, such as, two photon microscopy, electron microscopy, and scanning probe microscopy. By "preparing a biological specimen for microscopic analysis" is generally meant rendering the specimen suitable for microscopic analysis at an unlimited depth within the specimen.

In embodiments, the system is configured for measuring changes in the amount of biomaterial present in a well. As used herein, "biomaterial" refers to any biological material produced by an organism. In some embodiments, biomaterial comprises secretions, extracellular matrix, proteins, lipids, organelles, membranes, cells, portions thereof, and combinations thereof. In some embodiments, cellular material comprises secretions, extracellular matrix, proteins, lipids, organelles, membranes, cells, portions thereof, and combinations thereof. In some embodiments, biomaterial includes viruses. In some embodiments, the biomaterial is a replicating virus and thus comprises virus infected cells.

In embodiments, additional methods may be performed to further characterize the sample. For example, in addition to sequencing, the method includes protein analysis, lipid analysis, metabolite analysis (e.g., glucose analysis), or measuring the transcriptomic profile, gene expression activity, genomic profile, protein expression activity, proteomic profile, protein interaction activity, cellular receptor expression activity, lipid profile, lipid activity, carbohydrate profile, microvesicle activity, glucose activity, and combinations thereof.

EXAMPLES

Example 1. Integrated Multiomics Device

Nature has evolved an elegant solution where four nucleotides—adenine (A), cytosine (C), guanine (G), thymine (T)—form the primary code upon which all of life and biologic diversity is built. Next-generation sequencing (NGS) directly reads the four nucleotides (or DNA bases) and thus can read out a limitless number of possible sequences. This contrasts with alternative genetic detection technologies that require a priori knowledge of the DNA sequence of interest, such as DNA microarrays, targeted probe hybridization and polymerase chain reaction (PCR). These technologies require prior knowledge of the sequence of a DNA target, and in many cases are also limited by detection with a small number of fluorescent dyes. The capability of NGS to read the vast combinatorial repertoire of DNA, even without prior knowledge of the DNA target, makes it a uniquely powerful platform technology and universal detection method to read and interrogate biology. Beyond reading genomic DNA and RNA, the combination of NGS and designed DNA probes attached to antibodies introduce a wide range of multiomics applications, including imaging and measuring gene transcription and protein expression in individual cells and tissue pathology samples.

NGS has been a transformational technology for the life sciences industry and has been critical to ushering in the genomics age and accelerating our understanding of biology. Since its introduction in the mid-2000s, NGS technology has advanced greatly, which has increased the power of the technology and enabled its broad adoption by the life sciences community. The first NGS platform in the mid-2000s enabled a 50,000-fold drop in cost of sequencing the human genome as compared to the initial first genome sequenced as part of the Human Genome Project at a cost of $300 million. By 2015, the cost of sequencing a human genome reached $1,000 (at approximately 30× coverage, to achieve sufficient accuracy).

NGS can serve as an extremely versatile molecular tool in biology, extending well beyond its current applications. Today, NGS is used to sequence DNA and RNA to identify inherited and acquired mutations, measure gene expression by counting RNA transcripts, detect and identify pathogens, and when combined with certain sample preparation techniques, determine the epigenetic state of the DNA. Despite the advances that NGS has enabled in the genomics space, we believe the power of sequencing has not been fully realized and that innovation across the core elements of a sequencer can drive further improvement in the technology. Described herein are devices, compositions, and kits that enable sequencing to be extended beyond genomics and leveraged as a multiomics reader of biology. The devices, compositions, and kits described herein will transform genomics, epigenetics, transcriptomics, and proteomics (i.e., multiomics).

The device described herein leverages nucleic acid sequencing to enable multiomics analysis of single cells and tissues as both a universal detection method and in situ sequencing. Advantageously, the device is designed to provide high throughput analysis of nucleic acids and proteins, while also generating high resolution images of cellular morphology to enable computer-vision based analysis of cellular phenotype. This design reflects an appreciation of the tremendous potential for machine learning based image analysis to serve as a rich source of biomarker information for cancer and autoimmune disease translational research. The device described herein eliminates the need for customers to employ multiple systems over several day workflows, which is required by existing commercial methods. This enables researchers to perform large scale experiments that may fundamentally advance our understanding of biology, and, in turn, advance human health.

In recent years, systems have been developed for targeted gene sequencing in single cells, and for measuring levels of gene transcription in individual cells by sequencing readout. These tools have yielded new information that is not available from bulk sequencing measurements. However, current commercial methods have significant limitations. One limitation is that cells are broke open and tagged with DNA barcodes in droplets or emulsions, then pooled together into a sequencing run, thus losing information about cell morphology. Another limitation is the limited number of cells and samples that can be processed in an experiment. Finally, current methods struggle to achieve multiomics readout, with only limited ability to measure proteins along with DNA or RNA while maintaining cellular morphology.

For spatial analysis of tissue, the capabilities of current genomic technologies are even more limited. Most genomic analysis of tissue is done on a bulk basis, with no spatial resolution. Recently, several spatial analysis platforms have been developed and introduced commercially. However, these technologies currently have several limitations. First, most of these platforms currently have limited resolution and are unable to provide detailed information at the level of individual single cells. This limits information about subcellular localization and how the cells are organized in space within the tissue. Second, current commercial platforms are unable to provide high throughput. Experiments are limited to less than 20 samples per run, and in some cases just one sample per run, which limits the ability of users to conduct large scale experiments. Tissue samples have differences in cell morphology and/or function due to varied analyte and biomolecule levels (e.g., gene and/or protein expression) within the different cells. The specific position of a cell within a tissue (e.g., the cell's position relative to neighboring cells or the cell's position relative to the tissue microenvironment) can impact the cell's morphology, differentiation, fate, viability, proliferation, behavior, and signaling with other cells in the tissue.

The device described herein is designed for multiomics detection. The device may identify specific RNA and proteins (e.g., through the use of oligo-conjugated antibodies) using nucleic acid sequencing either as a universal detection method or for in situ sequencing along with cellular morphology and tissue organization. This provides significantly more information than is available today with current commercial single cell technologies. The addition of the cellular morphology along with spatial organization of biomolecules within the tissue microenvironment provides a data rich solution across many research applications to better understand cell development, maturation, and pathogenesis. The combination of these useful datasets from individual cells provides a more complete cellular picture as it will combine both phenotypic data along with detailed molecular characterization. Spatial information can provide information of biological and/or medical importance. For example, the methods, compositions, and devices described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

In embodiments, device described herein is designed for high throughput and large scale. The device is designed to be high throughput in order to enable researchers to perform large scale studies that are currently inaccessible but are needed for a more complete characterization and understanding of cells, and therefore biology. Current commercially available single cell technologies detect 10,000 to 100,000 cells in an experiment. The device described herein uses a microplate (e.g., multiwell-plate) approach (e.g., 4, 6, 12, 24, 48, 96, 384 or 1536 sample wells) designed to process 10,000 to 100,000 cells per well. For example, using a 96-multiwell-plate, the device is capable of a throughput of 1 million to 10 million cells. Current commercially available spatial analysis instruments can run an experiment involving only 4 to 20 tissue samples. With the devices described herein, it is possible to run up to 96 tissue samples per run. For tissue samples, the device is designed to retain the context of the cells within their cellular environment and to enable spatial analysis by returning both phenotypic data (cellular morphology, localization of different cell types and expression of different proteins within the context of the tissue) and molecular data at subcellular resolution and high throughput. The device can utilize fresh, fresh frozen, and FFPE samples.

The devices described herein are advantageously suited to study blood cancers. The device is designed to enable the mapping of the progression of blood cancers as they develop, pre-treatment and post-treatment, to fully characterize them across multiple molecular markers. The cellular phenotype, including morphology, could be valuable in helping to further characterize these cancer cells along with the molecular data of gene expression. The coupling of molecular data with the cellular phenotype and morphology will help to drive further understanding and identification of different types of cancer as well as provide the ability to interpret biological function.

Single cell sequencing is valuable for identifying the paired receptor data (light and heavy chains in B-cell or alpha and beta chains in T cell). By having a high throughput method that can sequence and retain the linkage of the two chains of the immune receptors, researchers are able to study in more depth the immune repertoire while also correlating each cell with its cellular phenotype. Additionally, it is possible to use a DNA conjugated antibody that recognizes the antigen to confirm the immune cell is binding to a specific antigen. This combination of data provides powerful information to interpret biological function as well as to further characterize immune cell types.

The device includes a microplate (e.g., a multiwell plate), wherein within each well is one or more polynucleotides. The device is capable of performing a plurality of SBS sequencing cycles. Briefly, an SBS sequencing cycle includes extending a primer strand with modified nucleotides (e.g., labeled, terminated nucleotides). This is followed by a wash and an optional addition of unlabeled, terminated nucleotides. The microplate is imaged, thereby detecting the incorporated modified nucleotide. A cleaving agent is introduced into each well, cleaving the terminated nucleotide, followed by a wash. The number of sequencing cycles depends on the application. For example, for reading out a barcode the number of sequencing cycles is about 5-10 cycles. In embodiments, for variable region sequencing, the number of sequencing cycles includes about 30-80 cycles.

In some embodiments, the wash includes incubating the sample with a wash buffer. In embodiments, washing includes removing the washing buffer. In embodiments, the washing buffer is 1×TE buffer, 1×TAE buffer, 1×TBE buffer, or PBS. In embodiments, the wash buffer contains a buffer (e.g., Tris, MOPS, HEPES, IVIES, or any other buffer known in the art), chelating agents (e.g., ethylenediaminetetraacetic acid (EDTA)), and/or metal ions (e.g., $Mg^{2+}$). In embodiments, the wash buffer can have a pH that is about 5.0, about 5.5, about 6.0, about 6.5, about 7.0, about 7.5, about 8.0, about 8.5, about 9.0, about 9.5, or about 10.0, or about 5.0 to 5.5, about 5.5 to 6.0, about 6.0 to 6.5, about 6.5 to 7.0, about 7.0 to 7.5, about 7.5 to 8.0, about 8.0 to 8.5, about 8.5 to 9.0, about 9.0 to 9.5, or about 9.5 to 10.0.

In an additional example, patterns of gene expression are determined by analyzing a series of tissue sections, in a manner analogous to image reconstruction in CT scanning (e.g., reconstructing three dimensional sections). Such a method can be used to measure changes in gene expression in disease pathology, e.g., in cancerous tissue and/or a tissue upon injury, inflammation, or infection. With the devices and methods as described herein, more detailed information on gene expression and protein localization in complex tissues is obtained, leading to new insights into the function and regulation both in normal and diseased states, and provides new hypotheses that can be tested.

Example 2: T-Cell and B-Cell Receptor Repertoire Sequencing

The functions of immune cells such as B- and T-cells are predicated on the recognition through specialized receptors of specific targets (antigens) in pathogens. There are approximately $10^{10}$-$10^{11}$ B-cells and $10^{11}$ T-cells in a human adult (Ganusov V V, De Boer R J. Trends Immunol. 2007; 28(12):514-8; and Bains I, Antia R, Callard R, Yates A J. Blood. 2009; 113(22):5480-5487). Immune cells are critical components of adaptive immunity in humans. Immune cells (e.g., T cells, B cells, NK cells, neutrophils, and monocytes) directly bind to pathogens through antigen-binding regions present on the cells. Within lymphoid organs (e.g., bone marrow for B cells and the thymus for T cells) the gene segments variable (V), joining (J), and diversity (D) rearrange to produce a novel amino acid sequence in the antigen-binding regions of antibodies that allow for the recognition of antigens from a range of pathogens (e.g., bacteria, viruses, parasites, and worms) as well as antigens arising from cancer cells. The large number of possible V-D-J segments, combined with additional (junctional) diversity, lead to a theoretical diversity of $>10^{14}$, which is further increased during adaptive immune responses. Overall, the result is that each B- and T-cell expresses a practically unique receptor, whose sequence is the outcome of both germline and somatic diversity. These antibodies also contain a constant (C) region, which confers the isotype to the antibody. In most mammals, there are five antibody isotypes: IgA, IgD, IgE, IgG, and IgM. For example, each antibody in the IgA isotype shares the same constant region.

While parts of the B-cell immunoglobulin receptor (BCR) can be traced back to segments encoded in the germline (i.e., the V, D and J segments), the set of segments used by each receptor is something that needs to be determined as it is coded in a highly repetitive region of the genome (Yaari G, Kleinstein S H. Practical guidelines for B-cell receptor repertoire sequencing analysis. Genome Med. 2015; 7:121. (2015)). Additionally, there are no pre-existing full-length templates to align the sequencing reads. Thus, obtaining long-range sequence data is incredibly insightful to gain insights into the adaptive immune response in healthy individuals and in those with a wide range of diseases. Utilizing the methods described herein, comprehensive in situ snapshots of the repertoire diversity for each class of antibody may be realized by using targeted oligonucleotide probes to sequence the C-V-D-J segments in intact B cells.

In situ sequencing typically involves tissue and/or cellular extraction, combined with the fixation and permeabilization of cells, followed by amplification of the target nucleic acid fragments for sequencing. Briefly, cells and their surrounding milieu are attached to a substrate surface, fixed, and permeabilized. Targeted oligonucleotide probes designed for C-V-D-J sequencing are then annealed to complementary regions which flank the nucleic acid of interest or a portion thereof. As described herein, the oligonucleotide probe hybridizes to regions which flank the target nucleic acid sequence or a portion thereof, referred to as the first and the second complementary regions. In the presence of a polymerase (e.g., a non-strand displacing polymerase), the complement to the target sequence is generated by extending from the first complementary region and is ligated to the second complementary region to form a circularized oligonucleotide. The resulting circularized oligonucleotide is primed with an amplification primer and extended with a strand-displacing polymerase to generate a concatemer containing multiple copies of the target nucleic acid sequence. This product is then primed and subjected to sequencing processes as described herein.

Optionally, one or more nucleotides within the amplification primer sequence, the sequencing primer sequence, and/or the immobilized oligonucleotide primer contains one or more functional moieties (e.g., bioconjugate reactive groups) that serve as attachment points to the matrix in which the cell is embedded (e.g., a hydrogel). In embodiments, one or more nucleotides within the amplification primer sequence, the sequencing primer sequence, and/or the immobilized oligonucleotide primer contains one or more functional moieties (e.g., bioconjugate reactive groups) that serve as attachment points to complementary bioconjugate reactive groups within the cell (e.g., a protein). In embodiments, a plurality of oligonucleotide primers are provided to the matrix in which the cell is embedded prior to amplification. In embodiments, a plurality of oligonucleotide primers are provided to the matrix in which the cell is embedded concurrently with amplification. In embodiments, the bioconjugate reactive group is located at the 5' or 3' end of the primer. In embodiments, the bioconjugate reactive group is located at an internal position of the primer e.g., the primer contains one or more modified nucleotides, such as aminoallyl deoxyuridine 5'-triphosphate (dUTP) nucleotide (s). In embodiments, the immobilized oligonucleotide primers may be used to aid in tethering the extension product to a confined area and may not be extended. In embodiments, the immobilized oligonucleotide primers may be used to aid in tethering the extension product to a confined area and may also be capable of being extended. For example, one or more immobilized oligonucleotides may be used to aid in tethering the extension product to a localized area and may be extended in an exponential RCA amplification reaction.

In embodiments, the devices and methods described herein may be utilized for B cell heavy and light chain in situ sequencing by targeting the combination of variable and constant gene segments that make up a given heavy and light chain. These methods provide unique insight into the spatial localization and recombination efforts of a cell's heavy and light chain genes. Likewise, the methods can be applied for T-cell receptor (TCR) alpha and beta chain in situ sequencing. The genes encoding alpha (TCRA) and beta (TCRB) chains are composed of multiple non-contiguous gene segments which include V, D, and J segments for TCRB and V and J for TCRA. As with B cell receptor diversity, the enormous diversity of TCR repertoires is generated by random combinatorial gene events. The devices and methods described here can be used to provide a comprehensive in situ view of TCR diversity in intact T cells.

Example 3. In Situ Transcriptomics

A wealth of information is reflected in the temporal and spatial variation of gene and protein expression among cells. Cellular macromolecules such as nucleic acids and proteins, occupy precise positions in cells and tissues, and a great deal of information is lost when these molecules are extracted. The methods available today for RNA sequence analysis (RNA-Seq) have the capacity to quantify the abundance of RNA molecules in a population of cells with great sensitivity. Current methods for single-cell RNA and protein analysis typically involve some method for "barcoding" the content of individual cells, followed by pooling the content and sequencing on a commercial DNA sequencing device (e.g., Illumina® NextSeq™ 500/550, MiSeq™, HiSeq™ 2500/3000/4000, or NovaSeq™). Illumina is a registered trademark, and NextSeq, MiSeq, HiSeq, and NovaSeq are trademarks of Illumina, Inc.

These methods have found wide application dissecting transcriptomic heterogeneity, and can handle upwards of 10,000 cells in an automated format, however they have several limitations and drawbacks. For example, if the cells of interest originate from a tissue sample, all information about the spatial distribution of the cells within the tissue is lost in the process of dissociating and isolating the cells prior to barcoding them. Often information about the intracellular distribution of analytes within the cellular microenvironment is also lost. This information is vital to designing therapeutic approaches to cancers, for example, where the tumor microenvironment often creates spatial gradients of nutrients and metabolic byproducts.

A different barcoding approach has been applied to spatial profiling of RNA & proteins in tissues. An example of this is the method developed by Spatial Transcriptomics, a Stockholm-based company purchased by 10× Genomics in 2018 and recently commercialized as "Visium Spatial" platform. This approach involves attaching a section of a frozen tissue of interest to patterned microarrays carrying spatially barcoded oligo-dT primers that capture the entire polyadenylated transcriptome contained in the tissue section. Each spot on the microarray contains a capture probe with a spatial barcode unique to that spot allowing the individual sequencing reads to be mapped to the originating spot. After cDNA synthesis on the surface via reverse transcription, the tissue is removed and the mRNA-cDNA hybrids are released from the array to be prepared for sequencing; see Vickovic, S., et al. Nat. Methods 16, 987-990 (2019) for greater detail on the approach. The current implementation of this technology includes a microarray with 100 µm spots spaced equidistant from each other, approximately 200 µm apart. The spatial resolution of this method is approximately 100 µm, which is sufficient for a coarse mapping of a pathology sample, but is insufficient to resolve individual cells, which are approximately 10-20 µm, or subcellular features (i.e., features less than 10 µm, such as the mitochondria). Wide adoption of this approach has been limited by the lack of scalability and accessible ways to automate and/or parallelize sequencing library preparation.

A number of new techniques have been described in for reading out RNA transcription levels in tissue sections directly (i.e., in-situ), without requiring spatial barcoding, based on single molecule fluorescence in situ hybridization. These include MERFISH (Multiplexed Error-Robust Fluorescence In Situ Hybridization), STARmap (Spatially-resolved Transcript Amplicon Readout mapping), DART-FISH, seq-FISH (Sequential Fluorescence In Situ Hybridization) and others (see for example Chen, K. H., et al. (2015). Science, 348(6233), aaa6090; Wang, G., Moffitt, J. R. & Zhuang, X. Sci Rep. 2018; 8, 4847; Wang X. et al; Science, 2018; 27, Vol 361, Issue 6400, eaat5691; Cai, M. *Dissertation*, (2019) UC San Diego. ProQuest ID: Cai_ucsd_0033D_18822; and Sansone, A. Nat Methods 16, 458; 2019). In all of these techniques, individual RNA transcripts are individually resolved, typically with pre-amplification or requiring multiple instances of labeled probes. Some of these techniques have been combined with super-resolution microscopy, expansion microscopy, or both, to increase the resolution and allow more transcripts to be resolved and thus counted. This increases the complexity and costs of detection, and can require laborious sample preparation and time consuming wash protocols.

Described herein are devices and methods for addressing these and other problems in the art. An aspect of the invention is to allow the readout of multiple RNA transcripts within one optically resolved volume (a voxel). The method includes targeting specific RNA sequences, and "translating" them to a DNA barcode, with a means for local amplification. The method includes selecting barcodes that are widely spaced in the combinatorial space of possible barcodes (large Hamming distance) and sequencing the barcodes on the same device. The devices and methods described herein (for example within the aspects and embodiments) reveal the distribution of specific RNA molecules in cells and tissues. In this way, patterns of differential gene expression may be observed which aids in the understanding of a particular gene's function, and ultimately the phenotype of the cell. The method includes demultiplexing the observed signal in each voxel into the set barcodes that includes the set of barcodes being used (e.g., by linear decomposition).

A method for "translating" RNA into a DNA barcode is to use a padlock probe, consisting of linear ssDNA, which is designed to have sequences complementary to 2 adjacent sequences on the target RNA. Once the padlock probes bind, the excess is washed away, and the linear strand of DNA is ligated to form a circle, using the RNA as a "splint". This only occurs if the two ends of the padlock probe are adjacent to each other. (The 5' end of the probe also has to be phosphorylated to enable ligation.) The padlock probe (and the resulting circle) contains several additional elements: a barcode for reading out the identity of the probe and its target; a complementary sequence for binding a sequencing primer. Optionally, the circle can contain multiple repeated barcodes and priming sites. The circle also needs to contain a site for RCA priming (Rolling Circle Amplification). In one embodiment, the priming site for RCA could have the same sequence as the sequencing primer, or have some degree of overlap.

Optionally, the RCA reaction can be done with modified nucleotides that contain chemical groups that serve as attachment points to the matrix in which the cell is embedded (e.g. a hydrogel). The attachment of the amplified product to the matrix can help confine & fix the amplicon to a small volume. In embodiments, amplification reactions include standard dNTPs and a modified nucleotide (e.g., amino-allyl dUTP, 5-TCO-PEG4-dUTP, C8-Alkyne-dUTP, 5-Azidomethyl-dUTP, 5-Vinyl-dUTP, or 5-Ethynyl dLTTP). For example, during amplification a mixture of standard dNTPs and aminoallyl deoxyuridine 5'-triphosphate (dUTP) nucleotides may be incorporated into the amplicon and subsequently cross-linked to the cell protein matrix by using a cross-linking reagent (e.g., an amine-reactive crosslinking agent with PEG spacers, such as (PEGylated bis(sulfosuccinimidyl)suberate) (BS(PEG)9)).

Optionally, one or more nucleotides within the amplification primer sequence, the sequencing primer sequence, and/or the immobilized oligonucleotide primer contains one or more functional moieties (e.g., bioconjugate reactive groups) that serve as attachment points to the matrix in which the cell is embedded (e.g. a hydrogel). In embodiments, one or more nucleotides within the amplification primer sequence, the sequencing primer sequence, and/or the immobilized oligonucleotide primer contains one or more functional moieties (e.g., bioconjugate reactive groups) that serve as attachment points to complementary bioconjugate reactive groups within the cell (e.g., a protein).

In embodiments, a plurality of oligonucleotide primers are provided to the matrix in which the cell is embedded prior to amplification. In embodiments, a plurality of oligonucleotide primers are provided to the matrix in which the cell is embedded concurrently with amplification. In embodiments, the bioconjugate reactive group is located at the 5' or 3' end of the primer. In embodiments, the bioconjugate reactive group is located at an internal position of the primer e.g., the primer contains one or more modified nucleotides, such as aminoallyl deoxyuridine 5'-triphosphate (dUTP) nucleotide(s). In embodiments, the immobilized oligonucleotide primers may be used to aid in tethering the extension product to a confined area and may not be extended. In embodiments, the immobilized oligonucleotide primers may be used to aid in tethering the extension product to a confined area and may also be capable of being extended. For example, one or more immobilized oligonucleotides may be used to aid in tethering the extension product to a localized area and may be extended in an exponential RCA amplification reaction.

An alternative method is to start with a reverse transcription step to convert the RNA to cDNA. The cDNA would then act as the target for the padlock probe. In embodiments, the cDNA could serve as a splint for ligation. Yet another method would be to simply bind a large probe directly to the RNA, without doing ligation or RCA. The large probe (e.g., branched DNA or a long concatemer) would carry multiple sites for binding sequencing primers & reading identical barcodes. The drawbacks to this method include higher non-specific background and less efficient binding kinetics of a large probe.

Probes can be designed to target multiple regions on the RNA of interest. This could be done to enhance the signal, and/or to provide a level of redundancy of targeting in case of mutations in a particular region. The probes that target 2 or more regions of the same RNA transcript could carry identical barcodes (for redundancy), or could carry distinct barcodes (to independently identify the region that is being detected).

Imaging. To read out the barcoded probes, a sequencing primer is introduced, and the barcode is read out. Preferably, the readout is done by SBS (Sequencing-By-Synthesis), with labeled and reversibly terminated nucleotides. Similar to the amplification primer sequence, and the immobilized oligonucleotide primer described supra, the sequencing primer sequence may contain one or more nucleotides containing functional moieties (e.g., bioconjugate reactive groups) that serve as attachment points to the matrix in which the cell is embedded (e.g. a hydrogel) or to a cellular component, and the SBS reactions are performed with labeled and reversibly terminated nucleotides. In embodiments, the modified sequencing primer is provided to the matrix in which the cell is embedded following amplification or concurrently with the SBS mixture. The attachment of the SBS product to the matrix via the sequencing primer can help confine and fix the amplicon to a small, localized volume.

Because the identity of all the barcodes is known a priori, the resulting signal can be deconstructed (demultiplexed) into the constituent components. Each sequencing cycle produces information about the magnitude of the signal in all 4 channels (a subset of 3 or 2 could also be used). The signal is then fit to a linear combination of component barcodes. For example, in embodiments when using 4-color detection (i.e., one color per nucleotides) a set of 10 sequencing cycles provides information in 40 dimensions (4 channels per cycle×10 cycles). Any of the $4^{10}$ possible barcodes would point to a unique position in this 40-dimensional space. Linear combinations of barcodes are thus easily resolvable, limited only by the accuracy of the sequencing signals. A typical example might be a set of 1,000-10,000 RNA targets, each encoded by a barcode selected from $4^N$ combinations, where N is the number of sequencing cycles or "digits" in the barcode. With 10 cycles, $4^{10}$, or approximately one million barcodes are available. This allows for the ability to select barcodes that are as far apart as possible in the available space (maximizing the Hamming distance), for more robust demultiplexing.

Practical limitations, such as noise in the sequencing signal, limits the total number of RNA transcripts that can be accurately detected in a single resolved volume (voxel). Reasonable upper limits might be 3, 10, 30, or greater than 100 targets per voxel, depending on the performance of the sequencing system.

Imaging. Either 2D or 3D fluorescent imaging modalities can be used. An advantage of 3D imaging is that a larger number of individual volumes can be resolved. 3D fluorescent imaging methods include confocal microscopy, light sheet microscopy, and multi-photon microscopy. For example, if the imaging system has a lateral resolution of 0.5 um, and a depth resolution of 1.0 um, a 10×10×10 um volume would contain 20×20×10=4,000 voxels. If each voxel can resolve 10 barcodes, then this would correspond to a capacity of 40,000 reads in a 10-um cube without pushing the limits of optical resolution. Further information can be gained by including expansion microscopy if subcellular resolution is required beyond the limits of diffraction, or if an even larger number of reads is desired.

Example 4. In Situ Proteomics

The human genome contains on the order of 25,000 genes which work in concert to produce on the order of 1,000,000 distinct proteins. A single mass spectrometry experiment can identify about 2,000 proteins or 0.2% of the total (Mirza, S. P., & Olivier, M. (2008). Physiological genomics, 33(1), 3-11), highlighting the need for novel approaches to identify more proteins. Certainly, when one considers the levels of mRNA are not proportional to the expression level of the proteins they code for, it is beneficial to determine the proteome of a sample (e.g., a cell). The methods described in Example 3, for spatial RNA transcriptomics can also be applied to spatial proteomics. For example, the proteins of interest are targeted by specific binding reagents, such as antibodies, fragments thereof (e.g., Fabs), aptamers, and the like, which carry a barcoded nucleic acid strand. That barcode can be used as splint for a padlock probe, as described above.

If higher specificity is required, RCA-PLA (proximity ligation) methods can be used; see for example the methods, complexes, and kits described in US 2002/0064779, US 2005/0287526, and US 2014/0170654, each of which are incorporated herein by reference. A "proximity ligation" is a method of ligating two (or more) nucleic acid sequences that are in proximity with each other through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929). For example, with these methods, an amplified product is produced only if two specific antibodies bind to the same protein (or within ~5 nm distance). One antibody provides the DNA oligo that acts as a splint for a padlock probe, while the other antibody carries the primer for RCA. Thus, RCA reaction only occurs if both antibodies bind to their respective epitopes on the target protein (or protein complex). The term "epitope" as used herein is defined as a small chemical group on the antigen molecule that is bound to by an antibody or aptamer. An antigen can have one or more epitopes. In many cases, an epitope is approximately five amino acids or sugars in size.

P-EMBODIMENTS

The present disclosure provides the following illustrative embodiments.

Embodiment P1. A device comprising: a sample stage configured to be coupled to a microplate receiver; a microplate receiver configured to be coupled to a microplate; at least one heating element thermally coupled to the microplate receiver; a fluidics dispenser configured to dispense one or more reagents into the microplate; and an imaging system configured to detect one or more features in the microplate; and a structure physically coupled to the sample stage, the heating element, the fluidics dispenser, and the imaging system.

Embodiment P2. The device of Embodiment P1, wherein the structure comprises a support structure formed of a base platform or a table.

Embodiment P3. The device of Embodiment P1, wherein the structure further comprises a containment structure having a lid.

Embodiment P4. The device of Embodiment P3, wherein the containment structure defines an enclosed, temperature-controlled region.

Embodiment P5. The device of Embodiment P4, wherein the sample stage is positioned inside the temperature-controlled region.

Embodiment P6. The device of Embodiment P1, wherein the imaging system comprises at least one of a kinematic mount and an auto-leveler mechanism.

Embodiment P7. The device of Embodiment P1, wherein the imaging system comprises at least one of a three-dimensional imager, a TDI scanner, a laser, a camera, an autofocus, and a transilluminator.

Embodiment P8. The device of Embodiment P1, wherein the imaging system is configured to detect one or more fluorescent features in the microplate.

Embodiment P9. The device of Embodiment P1, wherein imaging system is configured to detect one or more fluorescent features in each of the reaction chambers of the microplate.

Embodiment P10. The device of Embodiment P1, further comprising at least one reservoir physically coupled to the structure.

Embodiment P11. The device of Embodiment P10, wherein the at least one reservoir comprises at least one of a waste reservoir, a sequencing reagent reservoir, a clustering reagent reservoir, and a wash solution reservoir.

Embodiment P12. The device of Embodiment P1, wherein the device is configured to effectuate temperature cycling of the microplate.

Embodiment P13. The device of Embodiment P1, wherein the device comprises at least one manifold coupled to the structure.

Embodiment P14. The device of Embodiment P13, wherein the at least one manifold comprises at least one of a reagent aspiration manifold and a reagent dispense manifold.

Embodiment P15. The device of Embodiment P1, wherein the device comprises an integrated system of one or more interconnected chambers, ports, and channels in fluid communication and configured for carrying out an analytical reaction or process, either alone or in cooperation with an appliance or instrument that provides support functions.

Embodiment P16. The device of Embodiment P15, wherein the support functions comprise at least one of sample introduction, fluid and/or reagent driving means, temperature control, detection systems, data collection and integration systems, and are configured to determine the nucleic acid sequence of a template polynucleotide.

Embodiment P17. A device, the device configured to perform at least: a) in situ single cell analysis; b) in situ tissue analysis; and c) sequencing.

Embodiment P18. The device of Embodiment P17, wherein sequencing comprising at least one of RNA-sequencing and immune repertoire sequencing.

Embodiment P19. The device of Embodiment P17, wherein the device comprises a unitary structure.

Embodiment P20. The device of Embodiment P17, wherein the unitary structure includes a base platform or table.

Embodiment P21. The device of Embodiment P17, wherein the device is further configured to provide RNA transcription analysis (e.g., counting RNA) for targeted panels.

Embodiment P22. The device of Embodiment P17, wherein the device is further configured to perform protein expression analysis (e.g., counting of proteins) for targeted panels.

Embodiment P23. The device of Embodiment P17, wherein the device is further configured to perform sequencing of variable regions in immune cells (e.g., B-cells or T-cells) or cancer cells.

Embodiment P24. The device of Embodiment P17, wherein the device comprises at least one microplate.

Embodiment P25. The device of Embodiment P24, wherein the microplate includes 4, 6, 12, 24, 48, 96, 384 or 1536 sample wells.

Embodiment P26. The device of Embodiment P17, wherein the device comprises a sample stage configured to be coupled to a microplate receiver.

Embodiment P27. The device of Embodiment P17, wherein the device comprises an imaging system.

Embodiment P28. The device of Embodiment P27, wherein the imaging system comprises at least one of a kinematic mount and an auto leveler.

Embodiment P29. The device of Embodiment P27, wherein the imaging system comprises at least one of a three-dimensional imager, a TDI scanner, a laser, a camera, an autofocus, and a transilluminator.

Embodiment P30. The device of Embodiment P17, wherein the device comprises at least one structure configured to enclose a region and control temperature within the region.

Embodiment P31. The device of Embodiment P17, wherein the device is configured to perform temperature cycling of a microplate.

Embodiment P32. The device of Embodiment P17, wherein the device comprises at least one of a waste reservoir, a sequencing reagent reservoir, a clustering reagent reservoir, and a wash solution reservoir.

Embodiment P33. The device of Embodiment P17, wherein the device comprises at least one of a reagent aspiration manifold and a reagent dispense manifold.

Embodiment P34. A method of amplifying a target polynucleotide, the method comprising: contacting a microplate with a sample comprising a target polynucleotide; and amplifying the target polynucleotide to produce an amplification product, wherein amplifying comprises extension of an amplification primer hybridized to the target polynucleotide.

Embodiment P35. The method of Embodiment P34, wherein amplifying comprises a plurality of cycles of strand denaturation, primer hybridization, and primer extension.

Embodiment P36. The method of Embodiment P34, wherein the plurality of cycles comprises thermally cycling between about 35° C. and 65° C.

Embodiment P37. The method of Embodiment P34, wherein the plurality of cycles comprises thermally cycling between about 40° C. and 60° C.

Embodiment P38. The method of Embodiment P34, wherein the plurality of cycles comprises thermally cycling between (i) about 80-95° C. for about 15-30 sec for denaturation, and (ii) about 50-75° C. for about 1 minute for annealing/extension of the primer; or (i) about 72-80° C. for about 5 seconds to about 30 seconds for denaturation; and (ii) about 60-70° C. for about 30 to 90 seconds for annealing/extension of the primer; or (i) about 67-80° C. for about 5 seconds to about 30 seconds for denaturation; and (ii) about 60-70° C. for about 30 to 90 seconds for annealing/extension of the primer.

Embodiment P39. The method of any one of Embodiment P34 to Embodiment P38, wherein amplifying is performed by the device of any one of Embodiment P1 to Embodiment P16 or the device of any one of Embodiment P17 to Embodiment P33.

Embodiment P40. A method of sequencing a plurality of target nucleic acids of a cell in situ, said method comprising the following steps in situ for each of the plurality of target nucleic acids: hybridizing an oligonucleotide primer to the target nucleic acid, wherein said target nucleic acid is on a microplate, circularizing the oligonucleotide primer to generate a circular oligonucleotide, amplifying the circular oligonucleotide by extending an amplification primer hybridized to the circular oligonucleotide with a strand-displacing polymerase, wherein the amplification primer extension generates an extension product comprising multiple complements of the circular oligonucleotide; and sequencing the extension product.

Embodiment P41. The method of Embodiment P40, wherein circularizing comprises extending the 3' end of the oligonucleotide primer along the target nucleic acid to generate a complementary sequence, and ligating the complementary sequence to the 5' end of the oligonucleotide primer.

Embodiment P42. A method of detecting a plurality of different targets within an optically resolved volume of a cell in situ, wherein the targets are nucleic acid sequences or proteins on a microplate; said method comprising: associating a different oligonucleotide barcode from a known set of barcodes with each of the plurality of targets; sequencing each barcode to obtain a multiplexed signal in the cell in situ; demultiplexing the multiplexed signal by comparison with the known set of barcodes; and detecting the plurality of targets by identifying the associated barcodes detected in the cell.

Embodiment P43. A method of detecting a plurality of targets comprising different nucleic acid sequences within an optically resolved volume of a cell in situ on a microplate; said method comprising: associating a different oligonucleotide barcode from a known set of barcodes with each of the plurality of targets, wherein associating an oligonucleotide barcode with each of the plurality of targets comprises hybridizing a padlock probe to two adjacent nucleic acid sequences of the target, wherein the padlock probe is a single-stranded polynucleotide having a 5' and a 3' end, the padlock probe comprises at least one oligonucleotide barcode, and wherein the padlock probe comprises a primer binding sequence from a known set of primer binding sequences; sequencing each barcode to obtain a multiplexed signal in the cell in situ; demultiplexing the multiplexed signal by comparison with the known set of barcodes; and detecting the plurality of targets by identifying the associated barcodes detected in the cell.

Embodiment P44. A method of detecting a plurality of targets comprising different proteins within an optically resolved volume of a cell in situ on a microplate, said method comprising: associating a different oligonucleotide barcode from a known set of barcodes with each of the plurality of targets, wherein associating an oligonucleotide barcode with each of the plurality of targets comprises contacting each of the targets with a specific binding reagent, wherein the specific binding reagent comprises an oligonucleotide barcode, hybridizing a padlock probe to two adjacent nucleic acid sequences of the barcode, wherein the padlock probe is a single-stranded polynucleotide having a 5' and a 3' end, and wherein the padlock probe comprises a primer binding sequence from a known set of primer binding sequences; sequencing each barcode to obtain a multiplexed signal in the cell in situ; demultiplexing the multiplexed signal by comparison with the known set of barcodes; and detecting the plurality of targets by identifying the associated barcodes detected in the cell.

Embodiment P45. A method of sequencing an agent-mediated nucleic acid sequence of a cell, said method comprising administering a genetically modifying agent to the cell, and sequencing an agent-mediated nucleic acid sequence of the cell in situ according to any one of Embodiment P40 to Embodiment P44.

Embodiment P46. A method of identifying a nucleic acid sequence as an agent-mediated nucleic acid sequence, said method comprising administering a genetically modifying agent to a cell, detecting whether an agent-mediated nucleic acid sequence is present in the cell by sequencing a plurality of target nucleic acids according to any one of Embodiment P40 to Embodiment P44, and identifying the nucleic acid sequence as an agent-mediated nucleic acid sequence when the presence of the agent-mediated nucleic acid is detected in the cell.

Embodiment P47. A method of identifying a cell that responds to a genetically modifying agent, said method comprising administering a genetically modifying agent to the cell, detecting whether an agent-mediated nucleic acid sequence is present in the cell by sequencing a plurality of target nucleic acids according to any one of Embodiment P40 to Embodiment P44, and identifying a cell that responds to a genetically modifying agent when the presence of the agent-mediated nucleic acid is detected in the cell.

Embodiment P48. A method of identifying an agent as a genetically modifying agent, said method comprising administering an agent to a cell, detecting whether an agent-mediated nucleic acid sequence is present in the cell by sequencing a plurality of target nucleic acids according to any one of Embodiment P40 to Embodiment P44, and identifying the agent as a genetically modifying agent when the presence of the agent-mediated nucleic acid is detected in the cell.

Embodiment P49. The method of any one of Embodiment P40 to Embodiment P48, wherein the method is performed by the device of any one of Embodiment P1 to Embodiment P16 or the device of any one of Embodiment P17 to Embodiment P33.

What is claimed is:

1. A method of detecting polynucleotides with a microfluidic device, said method comprising:

positioning a first solid support in the microfluidic device, wherein the first solid support comprises a plurality of immobilized oligonucleotides, contacting the first solid support with a plurality of target nucleic acid molecules, amplifying the target nucleic acid molecules to generate a plurality of first amplification products immobilized to the first solid support, and sequencing the first amplification products; and positioning a second solid support in the microfluidic device, wherein the second solid support comprises a tissue or cell, contacting a second solid support with a plurality of polynucleotide probes, amplifying the polynucleotide probes to generate a plurality of second amplification products in the cell or tissue, and sequencing the second amplification products.

2. The method of claim 1, wherein sequencing comprises detecting a sequence of fluorescent signals.

3. The method of claim 1, wherein sequencing comprises sequencing-by-synthesis, sequencing by ligation, sequencing-by-hybridization, or pyrosequencing, and sequencing generates a sequencing read.

4. The method of claim 1, further comprising contacting the second solid support with eosin and/or 4', 6-diamidino-2-phenylindole (DAPI) sand detecting the eosin or DAPI.

5. The method of claim 1, wherein the second solid support comprises a tissue, wherein the tissue is about 5 µm to about 12 µm.

6. The method of claim 1, wherein the first solid support comprises 2 to 12 fluidic channels and wherein the second solid support comprises 2 to 12 fluidic channels.

7. The method of claim 1, wherein the immobilized oligonucleotides are covalently attached to a polymer, and the polymer is attached to the solid support.

8. The method of claim 1, wherein the polynucleotide probes comprise a barcode sequence.

9. The method of claim 1, wherein a polynucleotide probe binds to an RNA molecule.

10. The method of claim 1, wherein a polynucleotide probe binds to an oligonucleotide attached to a protein.

11. The method of claim 1, wherein a polynucleotide probe binds to an oligonucleotide attached to a cellular component.

12. The method of claim 1, wherein the first solid support comprises glass, and the second solid support comprises glass.

13. The method of claim 1, wherein the second solid support comprises a plurality of discrete regions, wherein each discrete region comprises a plurality of cells, wherein each discrete region is each other by about 1 mm to 5 mm.

14. The method of claim 13, wherein the second solid support comprises a coating for enhanced cell adhesion.

15. The method of claim 1, wherein sequencing the second amplification products occurs after sequencing the first amplification products.

16. The method of claim 1, amplifying the target nucleic acid molecules comprises bridge-PCR or rolling circle amplification.

17. The method of claim 1, amplifying the target nucleic acid molecules comprises rolling circle amplification.

18. The method of claim 1, wherein the second solid support is contacted with a plurality of polynucleotide probes, each polynucleotide probe comprising a different sequencing primer.

19. The method of claim 18, wherein sequencing the amplification products comprises hybridizing a first sequencing primer to an amplification product comprising a first sequencing primer binding sequence, followed by hybridizing a second sequencing primer to an amplification product comprising a second sequencing primer binding sequence.

20. The method of claim 1, wherein the second solid support comprises a plurality of discrete regions, wherein each discrete region comprises a plurality of tissues, wherein each discrete region is each other by about 1 mm to 5 mm.

* * * * *

UNITED STATES PATENT AND TRADEMARK OFFICE
CERTIFICATE OF CORRECTION

| | | |
|---|---|---|
| PATENT NO. | : 12,421,541 B2 | Page 1 of 1 |
| APPLICATION NO. | : 19/048060 | |
| DATED | : September 23, 2025 | |
| INVENTOR(S) | : Sandor Kovacs et al. | |

It is certified that error appears in the above-identified patent and that said Letters Patent is hereby corrected as shown below:

In the Claims

At Column 105, Claim number 1, Line number 20, delete "a" before the word "second" and insert the word --the--.

At Column 105, Claim number 4, Line number 33, delete "sand", and insert --and-- before the word "detecting".

At Column 105, Claim number 5, Line number 35, insert the phrase --a width of-- between the word "wherein" and the phrase "the tissue".

At Column 106, Claim number 13, Line number 16, insert the phrase --separated from-- after the word "is" and before the word "each".

At Column 106, Claim number 16, Line number 22, insert the word --wherein-- before the word "amplifying".

At Column 106, Claim number 17, Line number 25, insert the word --wherein-- before the word "amplifying".

At Column 106, Claim number 20, Line number 41, insert the phrase --separated from-- between the word "is" and "each".

Signed and Sealed this
Twenty-eighth Day of October, 2025

John A. Squires
*Director of the United States Patent and Trademark Office*